(12) United States Patent
Silbert

(10) Patent No.: US 10,094,847 B2
(45) Date of Patent: Oct. 9, 2018

(54) AUTOMATED SAMPLE PROCESSING INSTRUMENTS, SYSTEMS, PROCESSES, AND METHODS

(71) Applicant: Gen-Probe Incorporated, San Diego, CA (US)

(72) Inventor: Rolf Silbert, Del Mar, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 71 days.

(21) Appl. No.: 15/222,173

(22) Filed: Jul. 28, 2016

(65) Prior Publication Data

US 2017/0052205 A1 Feb. 23, 2017

Related U.S. Application Data

(60) Provisional application No. 62/199,690, filed on Jul. 31, 2015.

(51) Int. Cl.
*G01N 35/00* (2006.01)
*G01N 35/02* (2006.01)
*G01N 35/04* (2006.01)
*G01N 35/10* (2006.01)

(52) U.S. Cl.
CPC ......... *G01N 35/04* (2013.01); *G01N 35/0099* (2013.01); *G01N 35/026* (2013.01); *G01N 35/10* (2013.01); *G01N 35/109* (2013.01); *G01N 2035/0412* (2013.01); *G01N 2035/0491* (2013.01); *G01N 2035/0496* (2013.01)

(58) Field of Classification Search
None
See application file for complete search history.

(56) References Cited

U.S. PATENT DOCUMENTS

| | | | |
|---|---|---|---|
| 2005/0244887 A1* | 11/2005 | Kluttz | B01L 3/502 435/6.11 |
| 2010/0288061 A1 | 11/2010 | Hagen | |
| 2013/0130369 A1* | 5/2013 | Wilson | B01L 3/50825 435/289.1 |
| 2016/0176212 A1 | 6/2016 | Silbert et al. | |

* cited by examiner

*Primary Examiner* — Benjamin R Whatley
(74) *Attorney, Agent, or Firm* — Charles B. Cappellari; Kyle E. Conklin

(57) ABSTRACT

An automated instrument for processing a sample includes a first lock configured to move between a locked configuration and an unlocked configuration. The first lock is configured to be engaged with a first movable holding structure in the locked configuration to secure the first holding structure within the automated instrument. The first lock is configured to be disengaged from the first holding structure in the unlocked configuration to allow movement of the first holding structure within the automated instrument. The automated instrument also includes a robotic arm movable within the automated instrument and configured to move the first lock between the locked configuration and the unlocked configuration. The first holding structure is configured to hold a sample processing device and configured to move within the automated instrument when the first lock is in the unlocked configuration. The robotic arm can also be configured to move the sample processing device within the system.

20 Claims, 34 Drawing Sheets

AUTOMATED SAMPLE PROCESSING INSTRUMENTS, SYSTEMS, PROCESSES, AND METHODS

BACKGROUND

Field

Embodiments of this disclosure relate to automated sample processing instruments, systems, processes, and methods.

Background

Clinical laboratory work often involves a number of repetitive tasks that should be performed quickly and precisely. To provide more rapid and accurate laboratory results, many laboratory procedures and assays are being automated. Taking repetitive tasks out of the hands of laboratory technicians and having them performed by a machine may provide ergonomic and throughput benefits, but the task of automating intricate biological procedures has been fraught with difficulties. One source of these difficulties is the fact that biological materials are often complicated materials to work with. Contamination, accuracy, and completeness of an assay or sample processing procedure are ever-present concerns when the instrument is doing the work of a skilled laboratory technician. Nevertheless, automated instruments can reduce human error and offer a more consistent and repeatable series of sample manipulations and assays.

Accordingly there exists a need in the art to minimize laboratory technician handling time of biological, chemical, and biochemical specimens before assaying a sample, while ensuring that sample processing is completed accurately without the risk of contamination. Embodiments of this disclosure address these and other needs.

SUMMARY

In some embodiments, an automated instrument for processing a sample includes a first lock configured to move between a locked configuration and an unlocked configuration. The first lock is configured to be engaged with a movable first rack in the locked configuration of the first lock to secure the first rack within the automated instrument. The first rack is configured to hold a sample containing receptacle. The first lock is configured to be disengaged from the first rack in the unlocked configuration of the first lock to allow movement of the first rack within the automated instrument. The automated instrument also includes a second lock configured to move between a locked configuration and an unlocked configuration. The second lock is configured to be engaged with a movable second rack in the locked configuration of the second lock to secure the second rack within the automated instrument. The second rack is configured to hold a processing receptacle. The second lock is configured to be disengaged from the second rack in the unlocked configuration of the second lock to allow movement of the second rack within the automated instrument. The automated instrument also includes a robotic arm (i) movable within the automated instrument, (ii) configured to move the first lock between the locked configuration and the unlocked configuration of the first lock, (iii) configured to move the second lock between the locked configuration and the unlocked configuration of the second lock, and (iv) configured to move at least one of the sample containing receptacle and the processing receptacle within the automated instrument. The first rack is configured to move within the automated instrument when the first lock is in the unlocked configuration, and the second rack is configured to move within the automated instrument when the second lock is in the unlocked configuration.

In some embodiments, an automated instrument for processing a sample includes a first lock configured to move between a locked configuration and an unlocked configuration. The first lock is configured to be engaged with a first movable holding structure in the locked configuration to secure the first holding structure within the automated instrument. The first lock is configured to be disengaged from the first holding structure in the unlocked configuration to allow movement of the first holding structure within the automated instrument. The automated instrument also includes a robotic arm movable within the automated instrument and configured to move the first lock between the locked configuration and the unlocked configuration. The first holding structure is configured to hold a sample processing device and configured to move within the automated instrument when the first lock is in the unlocked configuration. In some embodiments, the robotic arm is configured to move the sample processing device within the system.

In some embodiments, a method of processing a sample using an automated instrument includes inserting a first structure holding a sample processing device into the automated instrument. The method also includes using a robotic arm of the automated instrument to move a first lock within the automated instrument to a locked configuration that engages the first structure to secure the first structure within the automated instrument. In some embodiments, the method also includes using a robotic arm of the automated instrument to move the sample processing device within the automated instrument.

In some embodiments, a method of processing a sample using an automated instrument includes inserting a first rack holding a sample containing receptacle into the automated instrument and inserting a second rack configured to hold a processing receptacle into the automated instrument. The method also includes using a robotic arm of the automated instrument to perform the following steps: (i) move a first lock within the automated instrument to a locked configuration that engages the first rack to secure the first rack within the automated instrument, (ii) move a second lock within automated instrument to a locked configuration that engages the second rack to secure the second rack within the automated instrument; and (iii) move at least one of the sample containing receptacle and the processing receptacle within the automated instrument.

Further features and advantages of the embodiments, as well as the structure and operational of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

DESCRIPTION OF THE DRAWINGS

The accompanying drawings, which are incorporated herein and form a part of the specification, illustrate the embodiments and, together with the description, further serve to explain the principles of the embodiments and to enable a person skilled in the relevant art(s) to make and use the embodiments.

FIGS. 11-1 and 11-2 illustrate a process flow for liquid based cytology (LBC) specimen processing, according to an embodiment.

The features and advantages of the embodiments will become more apparent from the detailed description set forth below when taken in conjunction with the drawings, in which like reference characters identify corresponding elements throughout.

DETAILED DESCRIPTION

Figure 1:
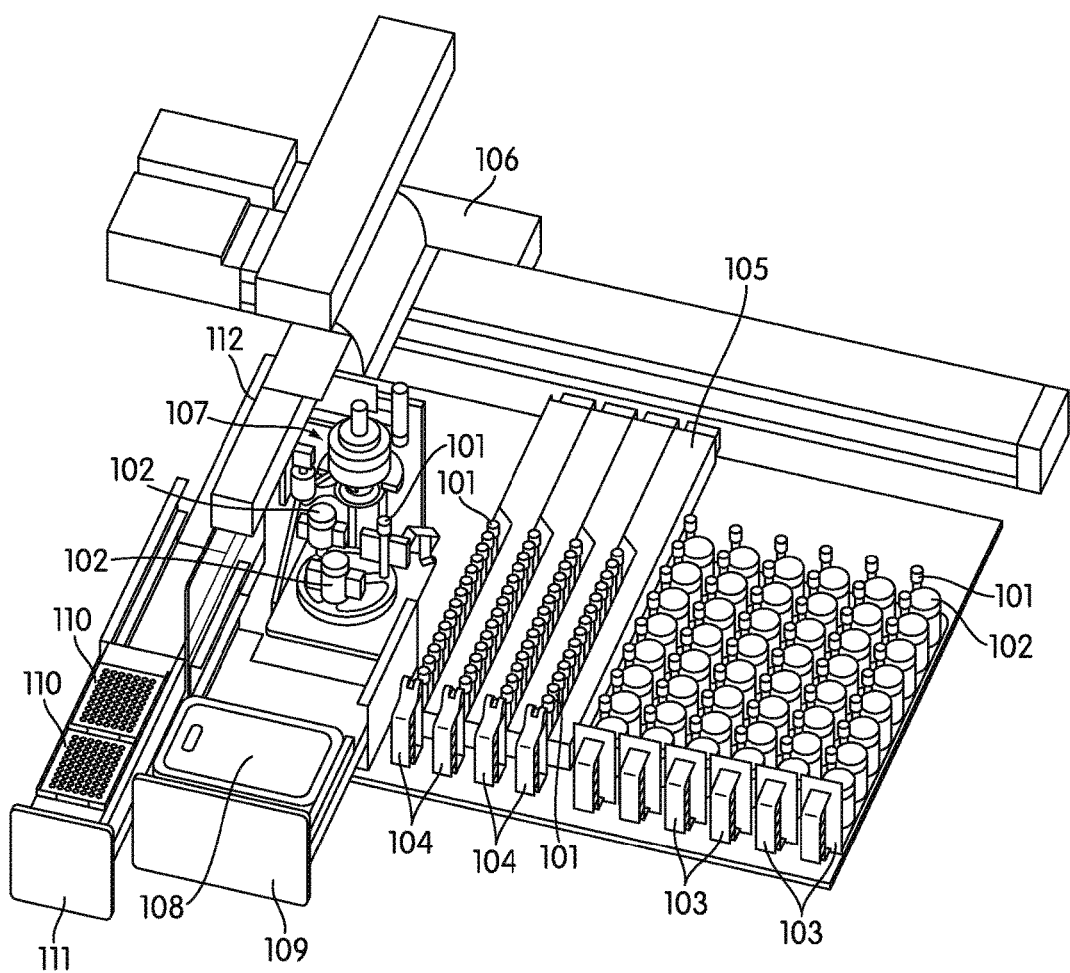
FIG. 1 illustrates one embodiment of a sample processing instrument.

The present disclosure will now be described in detail with reference to embodiments thereof as illustrated in the accompanying drawings. References to "one embodiment," "an embodiment," "some embodiments," "an exemplary embodiment," "for example," "an example," "exemplary," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "a" or "an" means "at least one" or "one or more."

As used herein, a "sample" refers to any material to be analyzed, regardless of the source. The material may be in its native form or any stage of processing (e.g., the material may be chemically altered or it may be one or more components of a sample that have been separated and/or purified from one or more other components of the sample). A sample may be obtained from any source, including, but not limited to, an animal, environmental, food, industrial or water source. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample.

As used herein, a "sample containing receptacle" refers to any type of fluid container, including, for example, a tube, vial, cuvette, cartridge, microtiter plate, etc., that contains a sample in its native form or at any stage of processing.

As used herein, a "processing receptacle" refers to any type of fluid container, including, for example, a tube, vial, cuvette, cartridge, microtiter plate, etc., that is configured to contain a sample at a point during processing. In some embodiments, a processing receptacle is formed with a material that can tolerate high temperatures (e.g., between 35° C.-90° C.) without deforming or leaching chemicals into a contained sample. Exemplary processing receptacles include Aptima® collection and transport tubes (Gen-Probe Incorporated, San Diego, Calif.).

As used herein, "assay instrument," "automated assay instrument," and "molecular assay instrument" all refer to an instrument capable of analyzing a sample and rendering a result. Any instrument capable of performing a hybridization assay, an amplification assay, a sequencing assay, or an immunoassay on a sample is included in this definition of an assay instrument. Exemplary assay instruments include the Tigris® and Panther® systems (Gen-Probe Incorporated, San Diego, Calif.).

As used herein, "machine vision" refers to a branch of engineering that uses computer vision in the analysis of images to extract data for controlling a process or activity. A machine vision process is targeted at recognizing the actual objects in an image and assigning properties to those objects—understanding what they mean.

As used herein, "orbital mixing" refers to a motion that induces a stirring effect in a liquid-filled reservoir without requiring a mixing utensil such as a spoon, magnetic particle, or similar device. In an exemplary embodiment of orbital mixing, the reservoir is subjected to extraneous forces, such as centripetal force and/or centrifugal force, which induce a stirring effect in the liquid contained therein. In some embodiments, sample processing instrument orbital mixing of sample containing receptacles and processing receptacles occurs in the sample processing station where, for example, one or more sample containing receptacle(s) and/or one or more reaction receptacle(s) are positioned on the periphery of the rotatable platform. In some embodiments, orbital mixing is achieved by rotating the platform in one direction around a central axis and by rotating the sample containing receptacle(s) and/or reaction receptacle(s) concurrently in an opposite direction than the rotatable platform, each about an individual axis that is different than the central axis of the rotatable platform as well as the axis of each other sample containing receptacle or processing receptacle.

As used herein, "robotic arm" refers to an electromechanical device that translates a payload (e.g., a pipettor, a receptacle gripper (such as a pick-and-place claw), a camera, a sensor, a capper/decapper, etc.) in the X, Y, and/or Z directions. In an embodiment, a robotic arm can move in the X, Y, and Z directions.

As used herein, "sample processing device" refers to a device used to process a sample. Exemplary sample processing devices include, for example, sample containing receptacles, processing receptacles, reagent containing receptacles, and pipette tips.

As used herein, "mucoid" refers to any viscous material, such as a viscous colloid or a viscous fluid.

As used herein, "power line communication," "power line communication system," or "PLC" refers to use of power lines in the instrument to transmit data signals throughout the instrument. Power line communications systems operate, for example, by imposing a modulated carrier signal on the wiring system.

In some embodiments, an assay can be carried out directly on a sample without any sample processing, but other samples require processing before carrying out an assay. Samples requiring some form of sample processing before subjecting the samples to the steps of an assay include, in some embodiments, cell samples, tissue samples, stool samples, mucus samples, semen samples, cerebrospinal fluid samples, blood samples, bone marrow samples, serum samples, urine samples, bile samples, respiratory samples, sputum samples, and exosome samples, among others.

FIG. 1 illustrates a portion of an automated instrument configured to process biological, chemical, or biochemical samples according to an embodiment. In some embodiments, the automated instrument includes a sample processing station 107, one or more input racks 103, one or more output racks 104, one or more robotic arms 112 (see also, for example, robotic arms 407 and 408 in FIG. 9), one or more sample pipettors (not shown in FIG. 1, but see, for example, pipettor 406 in FIGS. 9 and 14-16), one or more incubators 105, and an embedded controller (not shown in FIG. 1). In some embodiments, a robotic arm (for example, robotic arm 112 in FIG. 1 or robotic arm 408 in FIG. 9) is configured to move sample containing receptacles 102 and processing receptacles 101 within the automate instrument, for example, between input racks 103, sample processing station 107, and output racks 104. Each of these components of the automated instrument can be enclosed by an instrument housing. Sample containing receptacles 102 contain a sample, for example, an animal sample such as a liquid based cytology (LBC) specimen.

In some embodiments, processing receptacles 101 are configured differently than sample containing receptacles 102. For example, processing receptacles 101 can be sized and shaped differently than sample containing receptacles. For example, processing receptacles 101 can be narrower than sample containing receptacles in some embodiments. In other embodiments, processing receptacles 101 can be wider than sample containing receptacles 101. In other embodiments (not shown), processing receptacles 101 are configured similar to sample containing receptacles 102.

In some embodiments, one subset of sample containing receptacles 102 can be configured differently than other subsets of sample containing receptacles 102. For example, different subsets of sample containing receptacles 102, e.g., sample containing receptacles 210, can have different shapes and sizes from other subsets of sample containing receptacles 102, for example, sample containing receptacles 211, in some embodiments. In some embodiments, one subset of sample containing receptacles 102 can be capped, and another subset of sample containing receptacles 102 can be uncapped (not shown). Yet in other embodiments, all sample containing receptacles 102 are configured similarly.

In some embodiments, one subset of processing receptacles 101 can be configured differently than other subsets of processing receptacles 101. For example, referencing FIG. 30, different subsets of processing receptacles 101 can have different shapes and sizes from other subsets of processing receptacles 101 in some embodiments. In some embodiments, again referencing FIG. 30, one subset of processing receptacles 101 can be capped, and another subset of processing receptacles 101 can be uncapped. Yet in other embodiments, all processing receptacles 101 are configured similarly.

In some embodiments, processing receptacles 101 can be configured to be used in an assay instrument.

In some embodiments, sample pipettor 406 is configured to transfer samples from sample containing receptacles 102 (e.g., liquid based cytology (LBC) specimen collection containers), to processing receptacles 101 (e.g., Aptima® collection and transport tubes available from Gen-Probe Incorporated, San Diego, Calif.). In some embodiments, pipettor 406 is also configured to perform liquid level detection and reagent dispensing.

Figure 2:
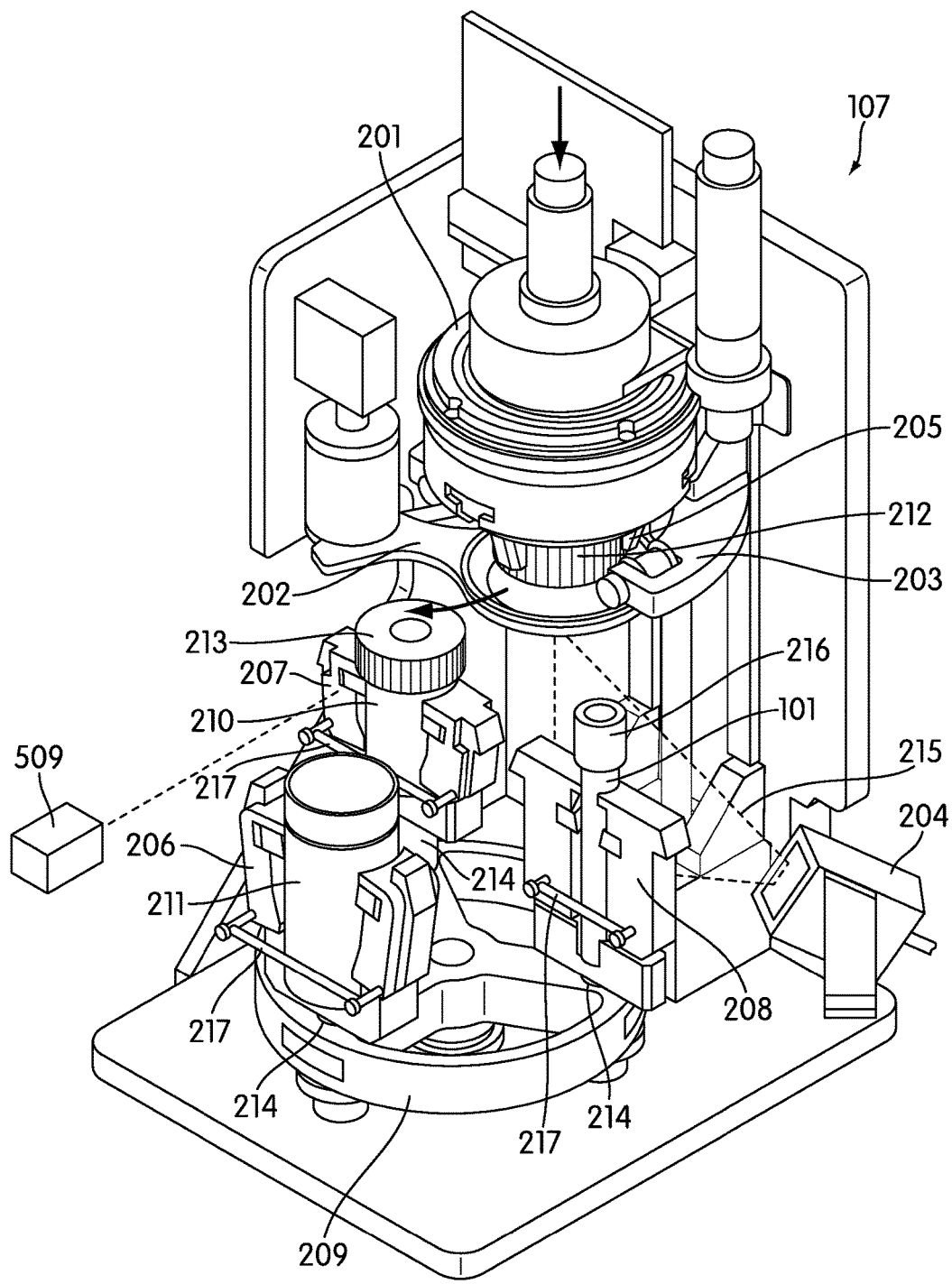
FIG. 2 illustrates a perspective view of one embodiment of a sample processing station of the sample processing instrument.
Figure 3:
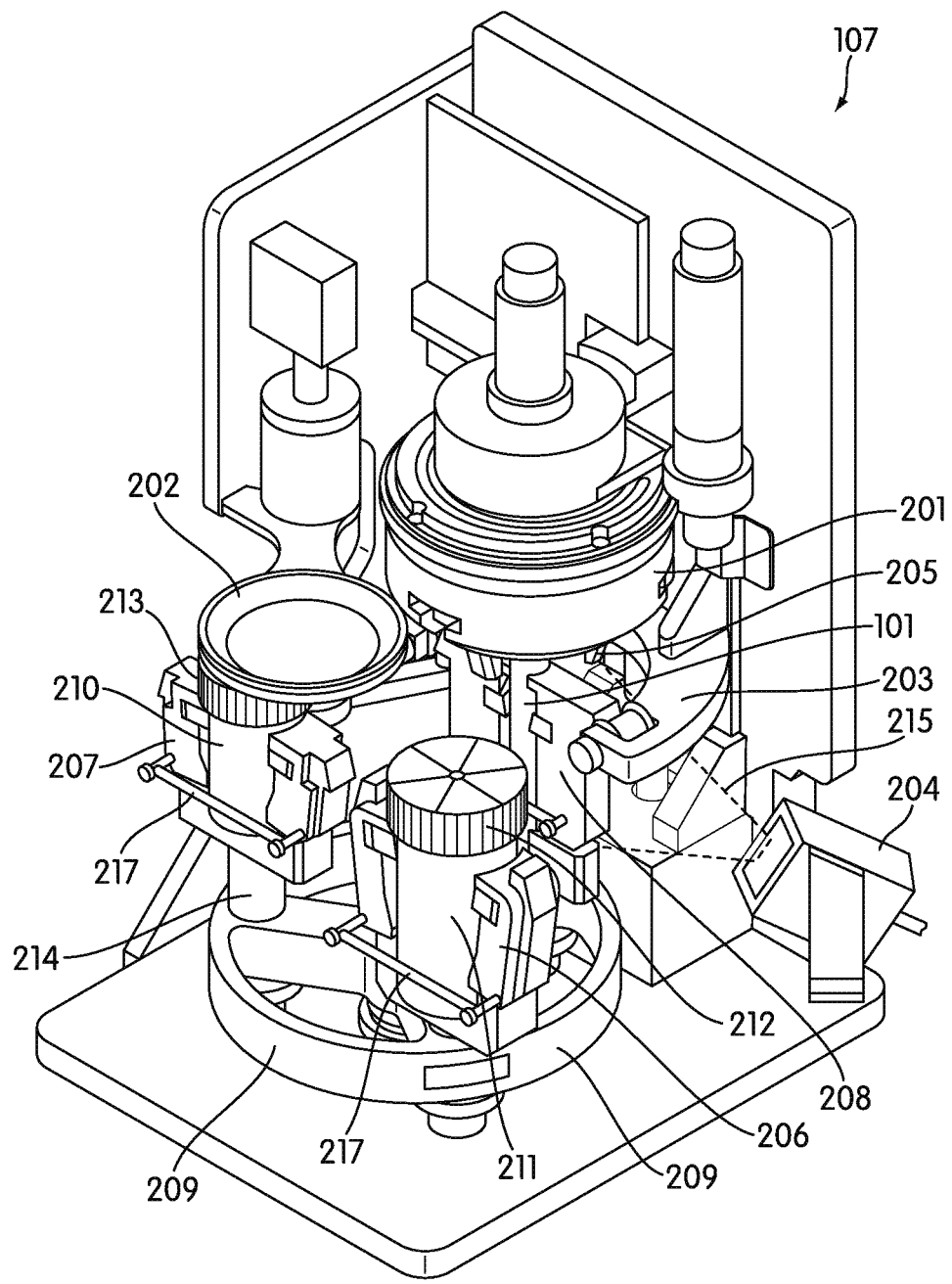
FIG. 3 illustrates another perspective view of one embodiment of the sample processing station of the sample processing instrument.

In some embodiments, sample processing station 107 is configured to hold sample containing receptacles 102 and processing receptacles 101, perform barcode reading (see, for example, barcode reader 204 in FIG. 2), barcode positioning, sample mixing, and capping/uncapping of the sample containing receptacles 102 and processing receptacles 101.

In some embodiments, the automated instrument includes one or more incubators 105. In some embodiments, incubators 105 are configured to hold one or more sample output racks 104 and to incubate the sample directly within processing receptacles 101. For example, LBC samples such as biological samples collected in a SurePath® (Becton Dickinson, Inc., Franklin Lakes, N.J.) sample containing receptacle 210 shown in FIGS. 2, 3, and 14-17, often require processing, such as reagent addition and heated incubation, before conducting a molecular assay. In other embodiments, LBC sample types such as those collected in a ThinPrep® (Hologic, Inc., Bedford, Mass.) sample containing receptacle 211 shown in FIGS. 2, 3, 5, 6, 10, and 14-17, may not require further process such as incubation. When the sample processing does not include heated incubation (in some embodiments), the one or more incubators 105 in the automated instrument, if configured to hold an output rack 104, can act as an output queue with temperature control turned off.

In some embodiments, the automated instrument also includes embedded controller that is configured to manage and process system-wide activities by delegating specific tasks to instrument sub-components or modules. Exemplary system activities include capping/decapping collection and processing receptacles, vortexing, moving collection and processing receptacles, pipetting, waste reservoir monitoring, monitoring consumable inventory, monitoring sample queues, maintaining run logs, monitoring process controls, monitoring system alarms, etc.

In some embodiments, the automated instrument is self-contained. In some self-contained embodiments, accessories can be used outside the instrument housing for the convenience of the operator and sample processing efficiency. Accessories of this type include, for example, handheld barcode readers, uninterruptible power supplies, and communication port (e.g., Ethernet, USB, eSATA, Firewire®, Wi-Fi, Bluetooth®, Thunderbolt®, RS-232, RS-485, etc.) compatible instrumentation, for example, for updating system configuration files, transferring systems logs, transferring sample information, etc.

In some embodiments, the automated instrument includes a software user interface. In one embodiment, the user interface incorporates an integrated touch screen for operator input, instrument control, status monitoring, and displaying sample tracking information. In some embodiments, the automated instrument includes data input devices. For example, the automated instrument can include USB ports, for example, for updating system configuration file, downloading sample tracking data and run logs, and connecting additional user interface devices such as a mouse or keyboard.

In some embodiments, the automated instrument includes a hardware user interface that a user can access various areas of the automated instrument, for example, the sample input bay, the sample output bay, and the consumable areas. In one embodiment, the automated instrument includes two or more cabinets or drawers on the front of the automated instrument to access these areas.

Figure 9:
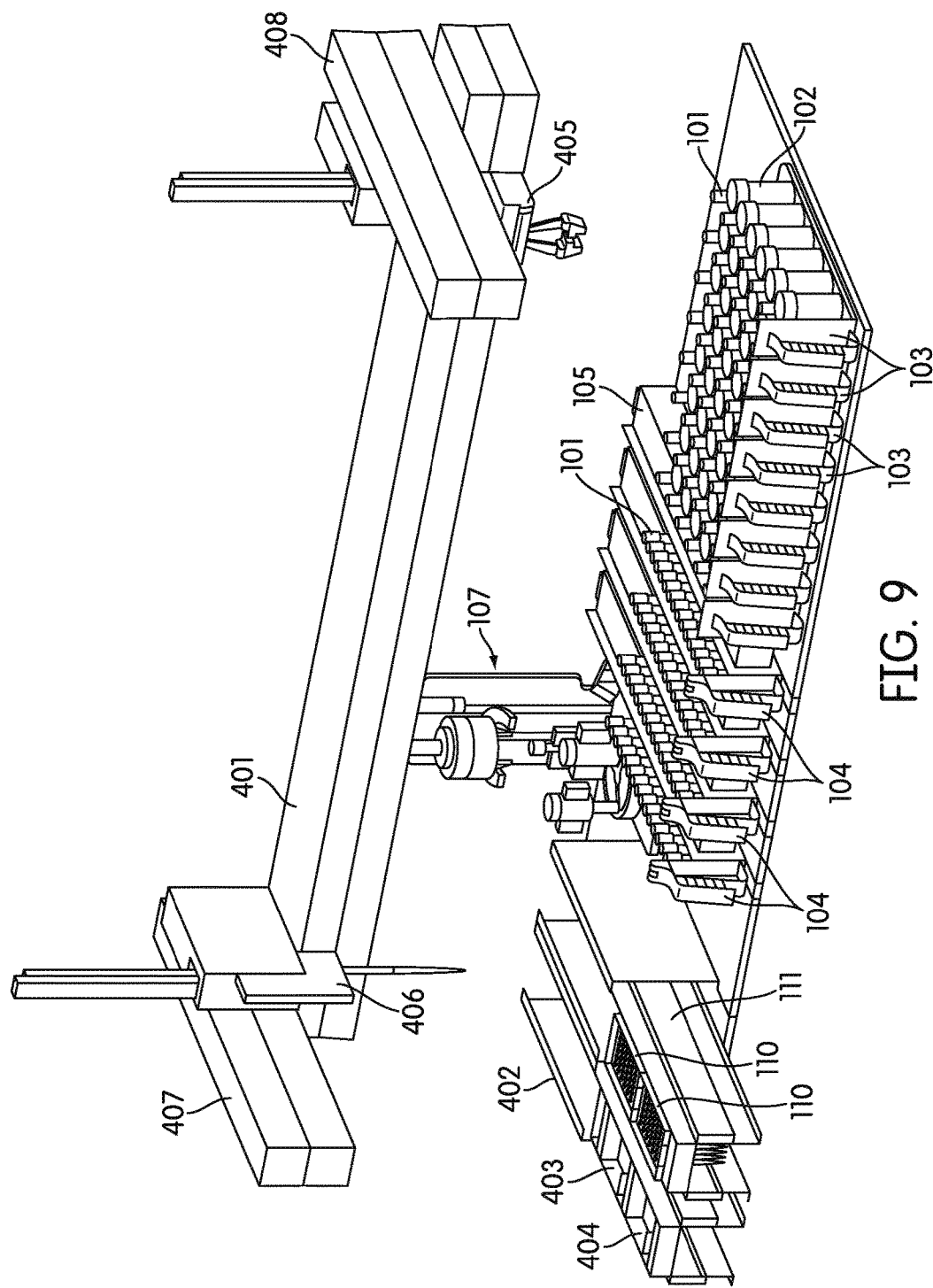
FIG. 9 illustrates another embodiment of a sample processing instrument.
Figure 10:
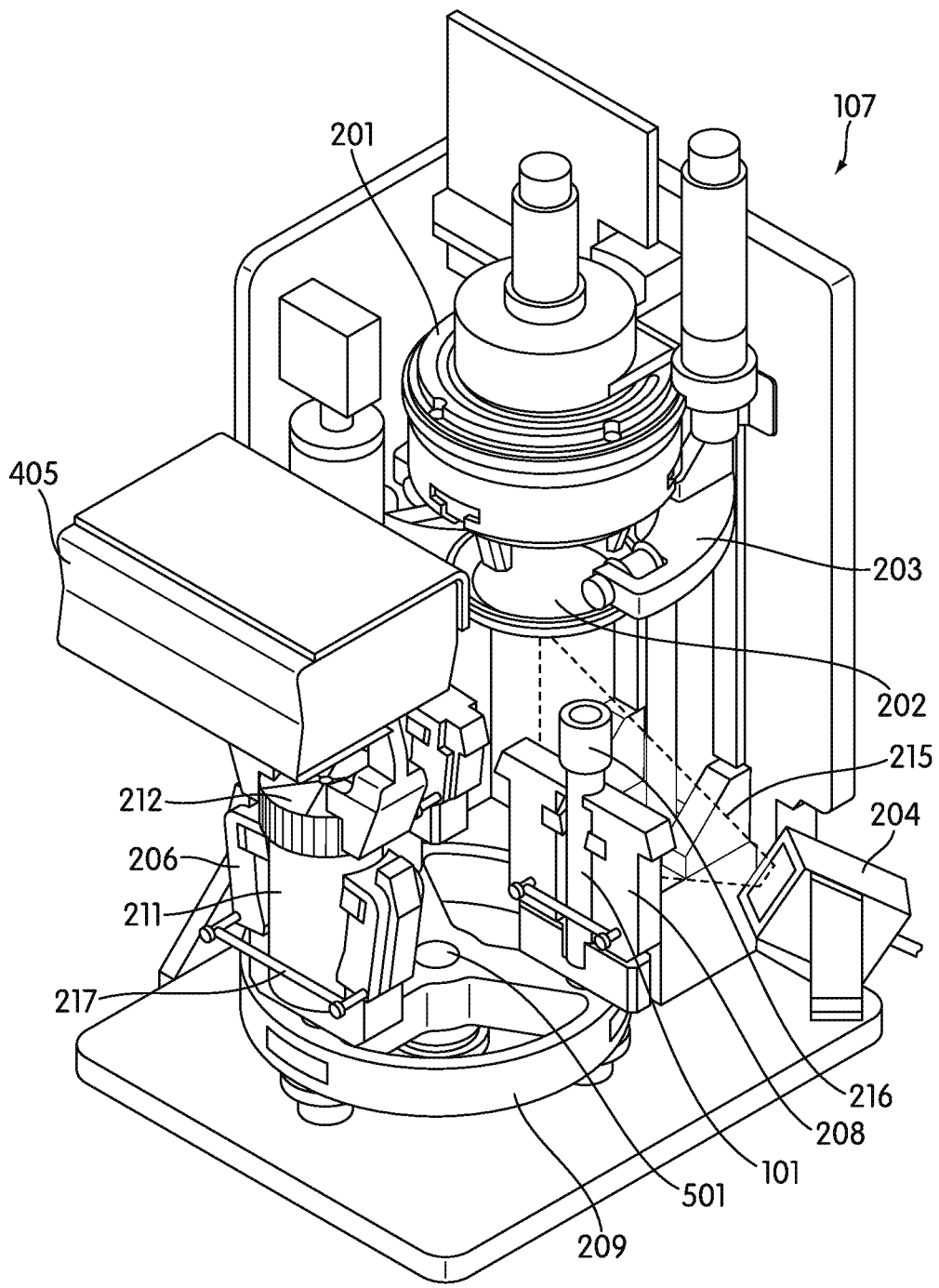
FIG. 10 illustrates a perspective view of a sample processing station that includes a robotic arm grasping a sample containing receptacle positioned in the service position, according to an embodiment.

In some embodiments as shown in FIG. 1, the automated instrument includes two doors and two drawers movable within the automated instrument. One drawer 111 is configured to contain a sample processing device, for example, instrument consumables such as pipette tips stored on trays 110 and sample processing reagents contained within reagent containing receptacles. The other drawer 109 is configured to contain a solid and/or liquid waste bin 108 that stores used instrument consumables, for example, used pipette tips, or discarded samples. Although FIG. 1 depicts only pipette tip trays 110 in consumable drawer 111, drawer 111 can also hold receptacles, such as reagent containing receptacles that contain sample processing reagents in some embodiments. Additionally, although waste bin 108 is depicted as a single container, waste bin 108 can be partitioned or separated into two independent waste storage areas, for example, one for solid waste (e.g., used pipette tips) and the other for liquid waste (e.g., discarded sample), in some embodiments. For example, FIG. 9 illustrates such an arrangement that includes a waste container drawer 402, a liquid waste bin 403, and a solid waste container (404).

Turning back to FIG. 1, the automated instrument includes an output bay configured to movably receive, for example, slidably receive, and hold one or more output racks 104. Output racks 104 can act as output queues for the automated instrument. The automated instrument also includes an input bay that can be configured to movably receive, for example, slidably receive, and hold one or more input racks 103 (also referred to herein as sample racks).

In some embodiments, the automated instrument is configured to handle a variety of sample types, including samples collected in different shaped collection receptacles (for example, sample containing receptacles 210 and 211—collectively sample containing receptacles 102). In one such embodiment, the input bay is configured to hold multiple types of sample input racks 103. For example, in one embodiment, the input bay is configured to hold sample input racks 103 containing ThinPrep® and/or SurePath® sample containing receptacles 211 and 210, respectively. In another embodiment, each sample input rack 103 is configured to hold a single type of specimen such that if two input racks 103 are in the input bay, one input rack 103 may contain only ThinPrep® sample containing receptacles 211, and the other input rack 103 may contain only SurePath® sample containing receptacles 210.

In another embodiment, each sample rack 103 is configured to hold two or more different shaped receptacles. For example, each sample rack 103 can be configured to hold two or more different shaped sample containing receptacles, for example, ThinPrep® and SurePath® sample containing receptacles 211 and 210, respectively. In such embodiments, sample rack 103 can be configured to hold SurePath® sample containing receptacles 210 (including the corresponding processing receptacles 101 in some embodiments) on one side, and ThinPrep® sample containing receptacles 211 (including the corresponding processing receptacles 101 in some embodiments) on the opposite side. In use, such a sample rack 103 can hold SurePath® sample containing receptacles 210, and then if flipped upside down, sample rack 103 can hold ThinPrep® sample containing receptacles 211.

In some embodiments, processing receptacles 101 held by sample rack 103 do not contain a sample.

In some embodiments, each drawer or bay can include indicator lights that provide visual feedback to the user, for example, feedback about the current state of the racks, consumables, or waste containers in the automated instrument. For example, the indicator lights can indicate to the user whether a particular rack (for example, an input rack 103 or an output rack 104) is being processed, and therefore, cannot be accessed. The indicator lights can also indicate to the user when it is safe to remove a rack (for example, an input rack 103 or output rack 104) that has been processed to make room for another rack. Similar indicator lights can be included for the consumable drawers. In one embodiment, when the drawers (for example, drawers 109 or 111) are open, the indicator lights are visible to the user for visual assistance during interventions.

In some embodiments, each input rack 103 is configured to hold both a sample containing receptacle 102 and a processing receptacle 101 that is configured differently than the sample containing receptacle 102. In such embodiments, input rack 103 can be configured to hold multiple pairs of sample containing receptacles 102 and processing receptacles 101, such that sample containing receptacles 102 and processing receptacles 101 are incorporated in a one-to-one ratio and in an alternating fashion as shown in FIG. 1. In such embodiments, the user, after verifying instrument consumable levels, can begin sample processing by simply inserting input rack 103 holding pairs of sample containing receptacles 102 and processing receptacles 101 into the input bay of the automated instrument.

Figure 7:
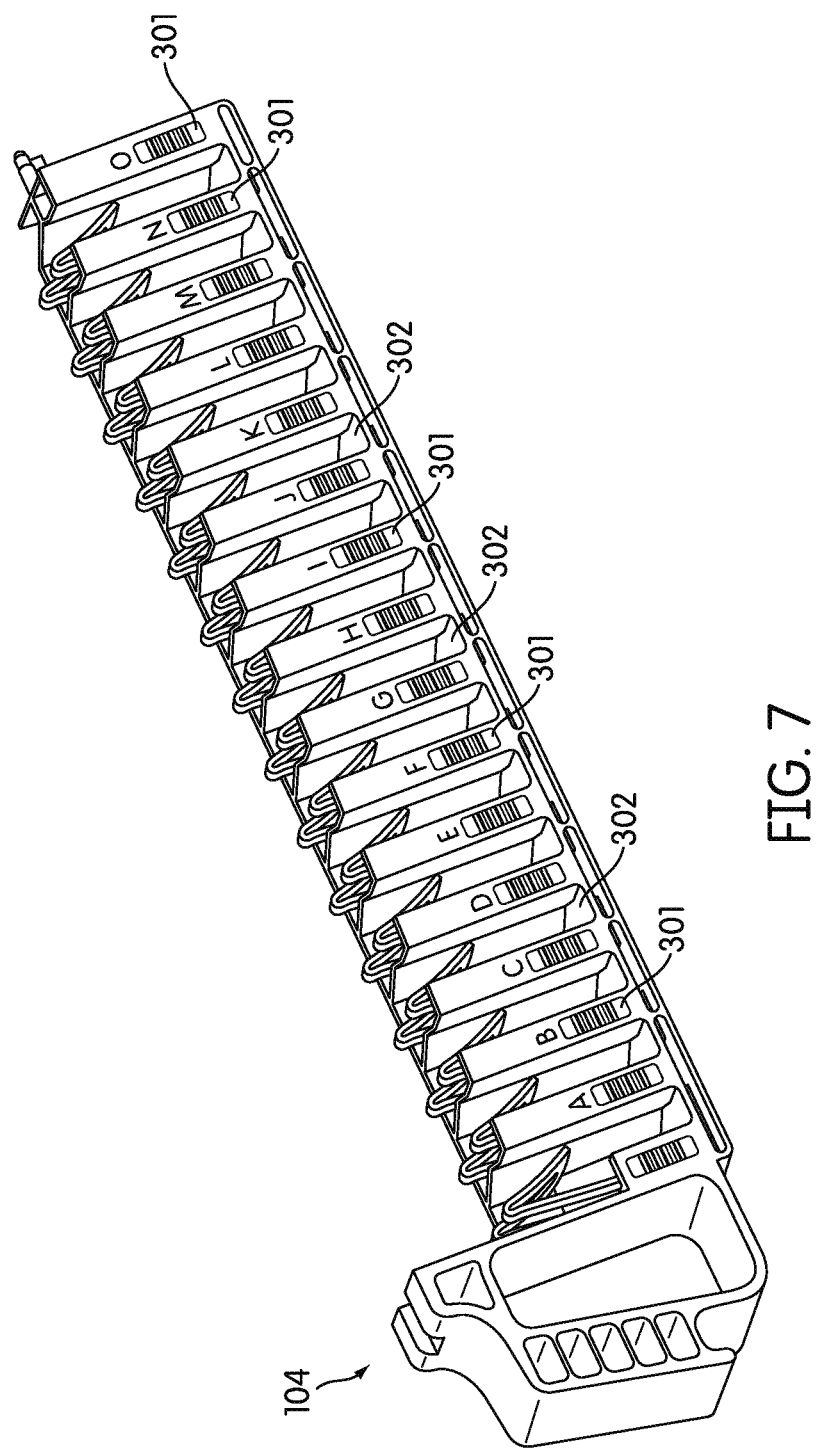
FIG. 7 illustrates a perspective view of an output rack, according to an embodiment.
Figure 8:
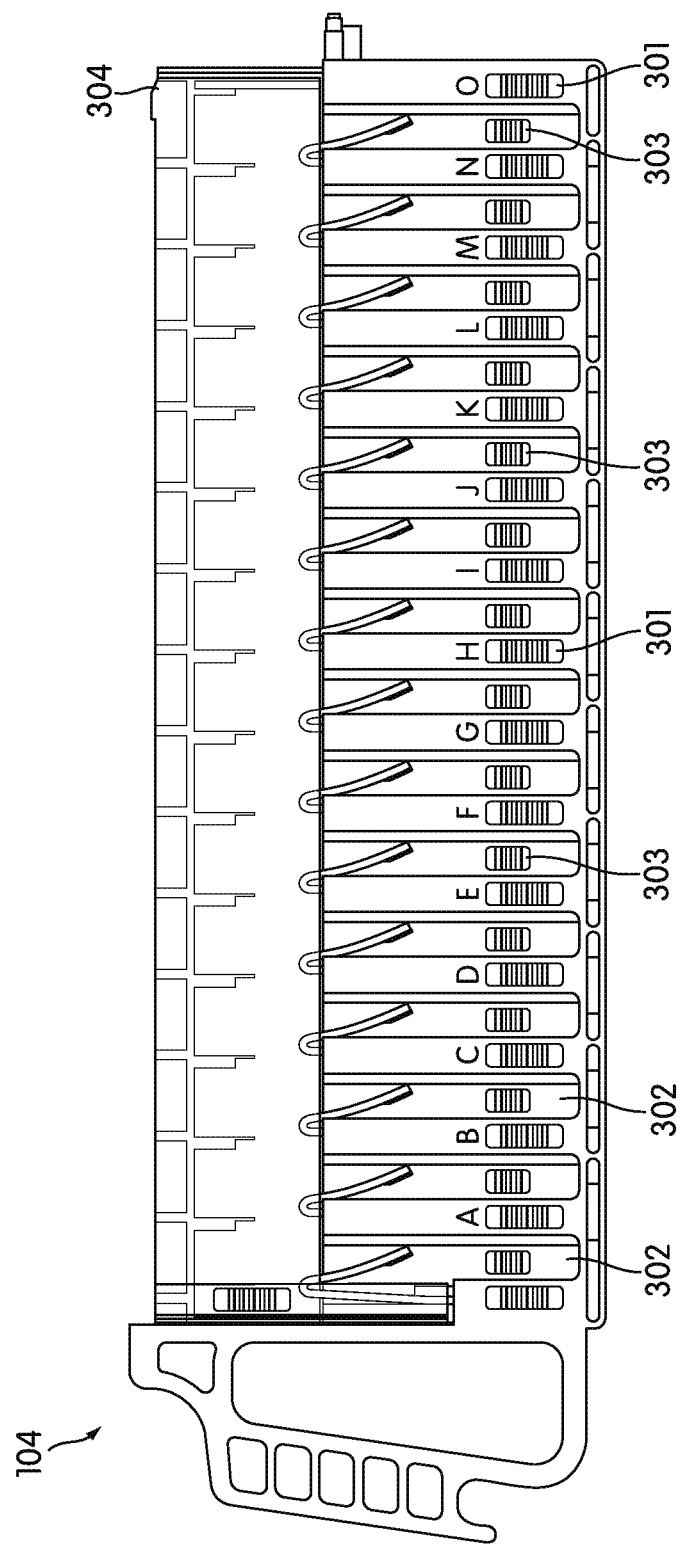
FIG. 8 illustrates another perspective view of an output rack including a cover, according to an embodiment.

FIGS. 7 and 8 illustrate an output rack 104 according to an embodiment. In some embodiments, output rack 104 is configured to hold a plurality of processing receptacles 101. In some embodiments, processing receptacles 101 held by output rack 104 are similarly configured, and in other embodiments, processing receptacles 101 held by output rack 104 can have dissimilar configurations. In some embodiments, the automated instrument automatically processes and moves processing receptacles 101 held by an input rack 103 to output rack 104. In some embodiments, processing receptacles 101 held by output rack 104 contain a sample. In other embodiments, processing receptacles 101 held by output rack 104 do not contain a sample.

In some embodiments, once processing receptacles 101 are placed on output rack 104, a user can retrieve output rack 104 to run assay(s) on the contents of the processing receptacles 101 using an assay instrument separate from the automated sample processing instrument. In some embodiments, output rack 104 is configured to be operable in an assay instrument that performs the assay, for example, an automated instrument capable of performing a molecular assay. For example, in some embodiments, output rack 104 of the processing instrument functions as an input rack for an assay instrument. In such embodiments, the user removes rack 104 holding processed samples in processing receptacles 101 from the automated processing instrument, and with or without any additional required activities such as attaching a cover to rack 104, inserts rack 104 in the input bay of an automated assay instrument, for example, a molecular assay instrument that performs a desired assay. In other embodiments, processing receptacles 101 in output rack 104 are manually transferred to an input rack configured to be operable in an automated assay instrument, for example, a molecular assay instrument that performs a desired assay.

In some embodiments, output rack 104 is configured to receive and hold a plurality of receptacles, for example, processing receptacles 101. In some embodiments, output rack 104 is configured to hold a plurality of tubular processing receptacles 101, such as test tubes or Aptima® collection and transport tubes. An exemplary output rack is described in U.S. Patent Application Publication No. 2010-0288061, published Nov. 18, 2010, which is incorporated by reference in this application. The gap between each pair of adjacent divider walls in output rack 104 defines a receptacle pocket 302, or receptacle-receiving area, for receiving an individual receptacle. In some embodiment, rack 104 includes pocket-identifying indicia, such as a machine readable label 301, for example, a barcode. Label 301 can be provided on the divider walls adjacent each pocket 302. The indicia may also include an alphanumeric identifier, e.g., "A", "B", "C", etc. The indicia uniquely identify each pocket 302. In some embodiments, rack 104 includes a machine readable label, such as "empty pocket" barcode 303, within each pocket 302 on an interior surface of each pocket 302 to uniquely identify each pocket 302 and to indicate when a receptacle, for example, processing receptacle 101, is not positioned within a pocket 302.

In some embodiments (not shown in FIGS. 7 and 8), output rack 104 includes a microtiter tray, for example, a microtiter plate having 96 wells. In such embodiments, a sample can be introduced to the microtiter tray of output rack 104 directly from a sample containing receptacle. In some processing embodiments that include incubation, an intermediate receptacle is used for incubation such that the sample is transferred from a sample containing receptacle to the intermediate receptacle and then transferred again from the intermediate receptacle to the microtiter tray of output rack 104 after incubation.

In some embodiments, the automated instrument tracks samples within the instrument. For example, matching machine readable labels such as barcodes can be placed on both a paired sample containing receptacle 102 and processing receptacle 101. In some embodiments, the automated instrument includes an onboard barcode reader 204 configured to read barcodes on once each sample containing receptacle 102 and processing receptacle 101 placed in sample processing station 107. In some embodiments, barcode reader 204 is configured to identify the position of the barcode on each sample containing receptacle 102 and processing receptacle 101 placed in sample processing station 107. For example, barcode reader 204 can identify the location of one or more edges of a label positioned on sample containing receptacle 102 and processing receptacle 101 and then deduce the location of the barcode on the label between the identified edges, or positioned a certain distance from a particular edge. In some embodiments, system process controls, receptacle barcodes, time/date stamps, user information, and system status are periodically stored in an onboard tracking system that is queryable via sample containing receptacle or processing receptacle barcode. In some embodiments, the user can manually enter an identifier associated with the barcode using user-interface touch screen or an optional handheld barcode scanner to perform a query. In some embodiments, the system software is configured to monitor the overall system status, reagent and supply inventories, processed specimen records, and maintenance. In some embodiments, samples are tracked within the system through the use of radio-frequency identification (RFID). In such an embodiment, sample-, assay-, reagent-, system status-, user-, time/date stamp-, and/or instrument-related information can be written or re-written to an RFID tag and tracked and/or updated through sample processing and beyond.

In some embodiment, the automated instrument includes one or more robotic arms configured to translate in the X, Y, and Z planes within the automated instrument and to move sample containing receptacles 102 and processing receptacles 101 within the automated instrument, for example, between positions (e.g., input racks 103, sample processing station 107, and output racks 104) in the instrument. For example, the automated processing instrument shown in FIG. 1 includes one robotic arm 112 configured to move sample containing receptacles 102 and processing receptacles 101, and the automated processing instrument shown in FIG. 14 includes one robotic arm 112 configured to move sample containing receptacles 102 and processing receptacles 101. And for example, the automated instrument shown in FIG. 9 includes robotic arm 408 configured to move sample containing receptacles 102 and processing receptacles 101, and the automated instrument shown in FIGS. 16 and 17 includes robotic arm 506 configured to move sample containing receptacles 102 and processing receptacles 101.

In some embodiments, the robotic arm configured to move sample containing receptacles 102 and processing receptacles 101 also includes a pipettor configured to aspirate and dispense a material. In some embodiments, the pipettor is an air-based pipettor configured to aspirate a sample from sample containing receptacles 102 or a reagent from a reagent containing receptacle and dispense the samples or reagents into processing receptacles 101. For example, robotic arm 112 configured to move sample containing receptacles 102 and processing receptacles 101 in FIG. 1 can include a pipettor, and robotic arm 112 configured to move sample containing receptacles 102 and processing receptacles 101 in FIGS. 14 and 15 can include a pipettor 406.

In some embodiments, the robotic arm that includes the pipettor is a separate from the robotic arm configured to move sample containing receptacles 102 and processing receptacles 101. For example, in FIG. 9, robotic arm 407 includes pipettor 406, and robotic arm 408 is configured to move sample containing receptacles 102 and processing receptacles 101. And for example, in FIGS. 16 and 17, robotic arm 112 includes pipettor 406, and robotic arm 506 configured to move sample containing receptacles 102 and processing receptacles 101.

In some embodiments, pipettor 406 and receptacle gripper 405 are incorporated on the same robotic arm (for example, robotic arm 112 in FIGS. 14 and 15), but each has an independently operable Z-axis. In such embodiments, pipettor 406 and receptacle gripper 405 have common X and Y axes, but two independent Z axes to service pipettor 406 and receptacle gripper 405. In some embodiments, robotic arm 112 includes a Cartesian system with belt driven X and Y axes and gear driven Z axes. In some embodiments, robotic arm 112 includes motors that have rotary encoders and home and limit sensors. In some embodiments, robotic arm 112 can move to any point on the instrument deck within the automated instrument in about 2 seconds or less.

One example of a pipettor 406 is a fully integrated OEM module (available from Tecan Group Ltd., Mannedorf, Switzerland) capable of dispensing volumes from 10-1000 uL with a CV of 0.75%. In such embodiments, a pipettor head of pipettor 406 is mounted a Z axis of robotic arm 112. In some embodiments, pipettor 406 is compatible with Tecan disposable pipette tips (e.g., 10 µl, 50 µl, 200 µl, 1000 µl, with or without filter), and is an air-based-pipettor that does not require tubing, valves, or syringes. In some embodiments, the pipettor head of pipettor 406 contains advanced on-board pump diagnostics, self-test, and error reporting. In some embodiments, pipettor 406 is configured to detect the level of the liquid within a receptacle, for example, using an integrated pressure sensor (pLLD) and is compatible with external capacitive liquid level detection hardware (cLLD), and configured to provide real time streaming data from one or more pressure sensor(s) for process monitoring. In some embodiments, pipettor 406 includes a DiTi presence sensor and DiTi ejection mechanism.

In some embodiments, receptacle gripper 405 is configured to pick-and-place sample containing receptacles 102 and processing receptacles 101 within the system. In one embodiment, receptacle gripper 405 is configured to move along a second Z axis of robotic arm 112. In some embodiments, gripper 405 includes a cam disk that opens and closes one or more prongs of gripper 405 when rotated CW/CCW. In such embodiments, the cam disk is optionally driven by a small high torque DC gear motor or stepper motor. A variety of additional gripper mechanisms are also contemplated and known in the art.

In another embodiment, such as that depicted in FIG. 9, the automated instrument includes two or more robotic arms, for example, robotic arms 407 and 408. Robotic arm 407 includes a dedicated pipettor 406, and robotic arm 408 includes a dedicated receptacle gripper 405.

In some embodiments, samples (e.g., an aliquot) are transferred from sample containing receptacles 102 to processing receptacles 101 in a serial fashion. For example, pipettor 406 is configured to take an aliquot of a sample from one sample containing receptacle 102 and transfer the aliquot to a processing receptacle 101. Thereafter pipettor 406 is configured to take another aliquot of a different sample from a different sample containing receptacle 102 and transfer the aliquot to another, different processing receptacle 101. An exemplary process for transferring and processing the sample, for example, at sample processing station 107, is described in detail below.

In some embodiments, the automated instrument is configured to add a reagent to a sample and/or incubate the sample as part of the sample processing. In some embodiments, the automated instrument includes onboard incubators 105 that are configured to heat output racks 104 as a final processing step before they are removed from the automated instrument. In some embodiments, each output rack 104 generally contains a single type of sample—for example, one that requires heated incubation or one that does not. Incubator 105 in these embodiments serve can serve at least two functions—sample incubation and as an output queue for the system. Each incubator 105 can be configured to contain 1, 2, or multiple slots, each capable of housing an output rack 104. In some embodiments, incubators 105 use Kapton heater foil for heating and passive convection flow for cooling. A variety of other incubator configurations are similarly contemplated for use in other embodiments, regardless of the configuration of the incubator, such as forced air convection, Peltier device heating, resistive heating, circulating heated gas or liquid, etc. In some embodiments, samples located in incubator 105 will remain at the temperature set point +/−2° C. at steady state. In some embodiments, incubators 105 are surrounded by insulating material, such as foam insulation.

In some embodiments, when samples are incubated in output racks 104, the sample are generally incubated in batches corresponding to the maximum number of positions on the output rack 104, or less. For example, 15 samples, or less, in a single output rack 104 may be incubated at one time. Of course, the number of samples in an output rack 104 can be more or less than 15 samples depending on the number of receptacle holding pockets available in rack 104 and the number of samples to be processed.

Figures 1, 11:
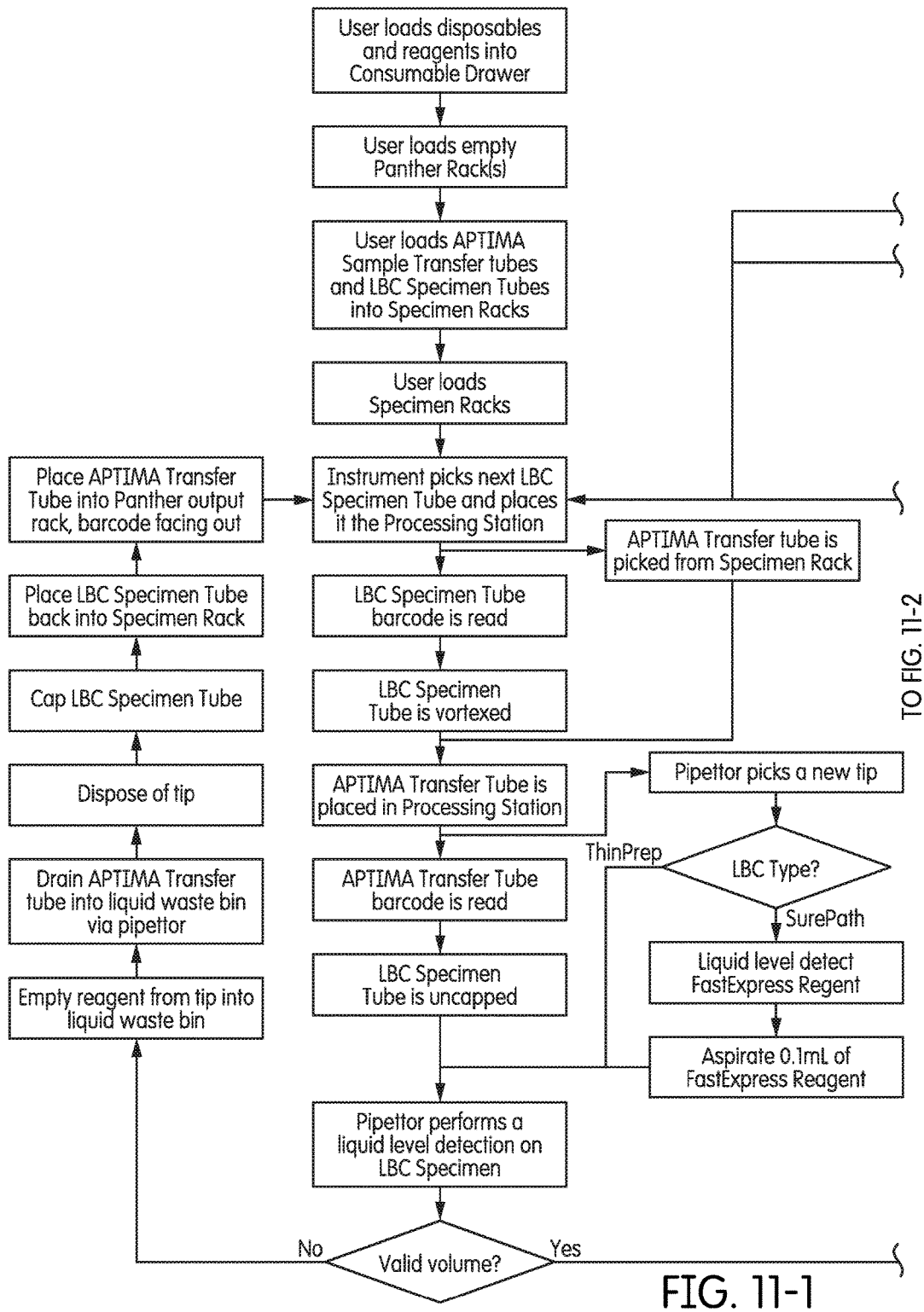
Figures 2, 11:
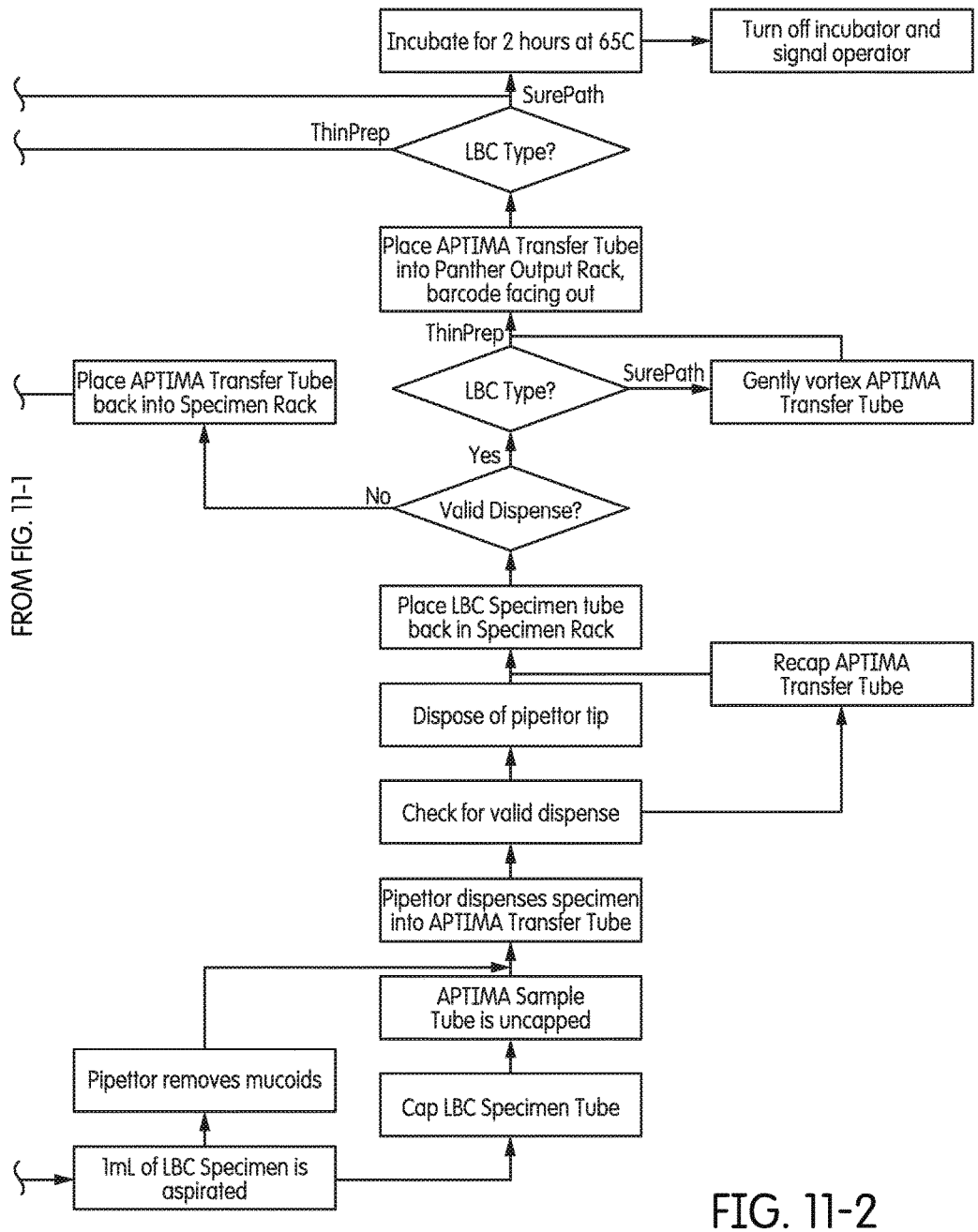

Another aspect of the automated instrument is that it permits a level of tuneability to provide automated sample processing according to protocols established by the manufacturer that established the particular assay to be run. These protocols are most frequently in accordance with regulatory guidelines and mandates. In a further aspect, the instrument permits automated sample processing according to protocols established by the manufacturer of the sample containing receptacle. For example, LBC specimens can be processed in an automated fashion on the instrument in accordance with, for example, the ThinPrep® or SurePath® protocol. In another embodiments, the sample racks 103 are tagged (such as by way of an RFID tag, a mechanical flag, a unique machine readable identifier, machine vision, barcode readers, or another means) such that the instrument will recognize the type of sample present in the sample rack 103, and will automatically run the sample processing protocol that is specific for that type of sample. When multiple different sample racks 103 are present, each containing samples requiring a processing protocol that is different from the protocol for any or each other rack 103, the instrument automatically processes the samples according to a rule set that balances throughput with time-to-next-result. For example, sample racks 103 containing samples in Thin-Prep® sample containing receptacles 211 can be loaded on the automated processing instrument for processing together with racks 103 containing samples in SurePath® sample containing receptacles 210. FIG. 11 presents an exemplary process flow for preparing a combination of ThinPrep® and SurePath® specimens in an automated instrument according to an embodiment.

Embodiments of a sample processing instrument are depicted in FIGS. 14-17. In these embodiments, the automated instrument includes a dedicated incubator 504 for heated incubation of processing receptacles 101 that require incubation. In some embodiments, a receptacle gripper of a robotic arm (for example, receptacle gripper 405 or 507) will move processing receptacles 101 to incubator 504, for example, after completion of processing in sample processing station 107. After incubation is complete, a receptacle gripper of a robotic arm (for example, receptacle gripper 405 or 507) will move processing receptacles 101 from incubator 504 to an output rack 104.

Figure 14:
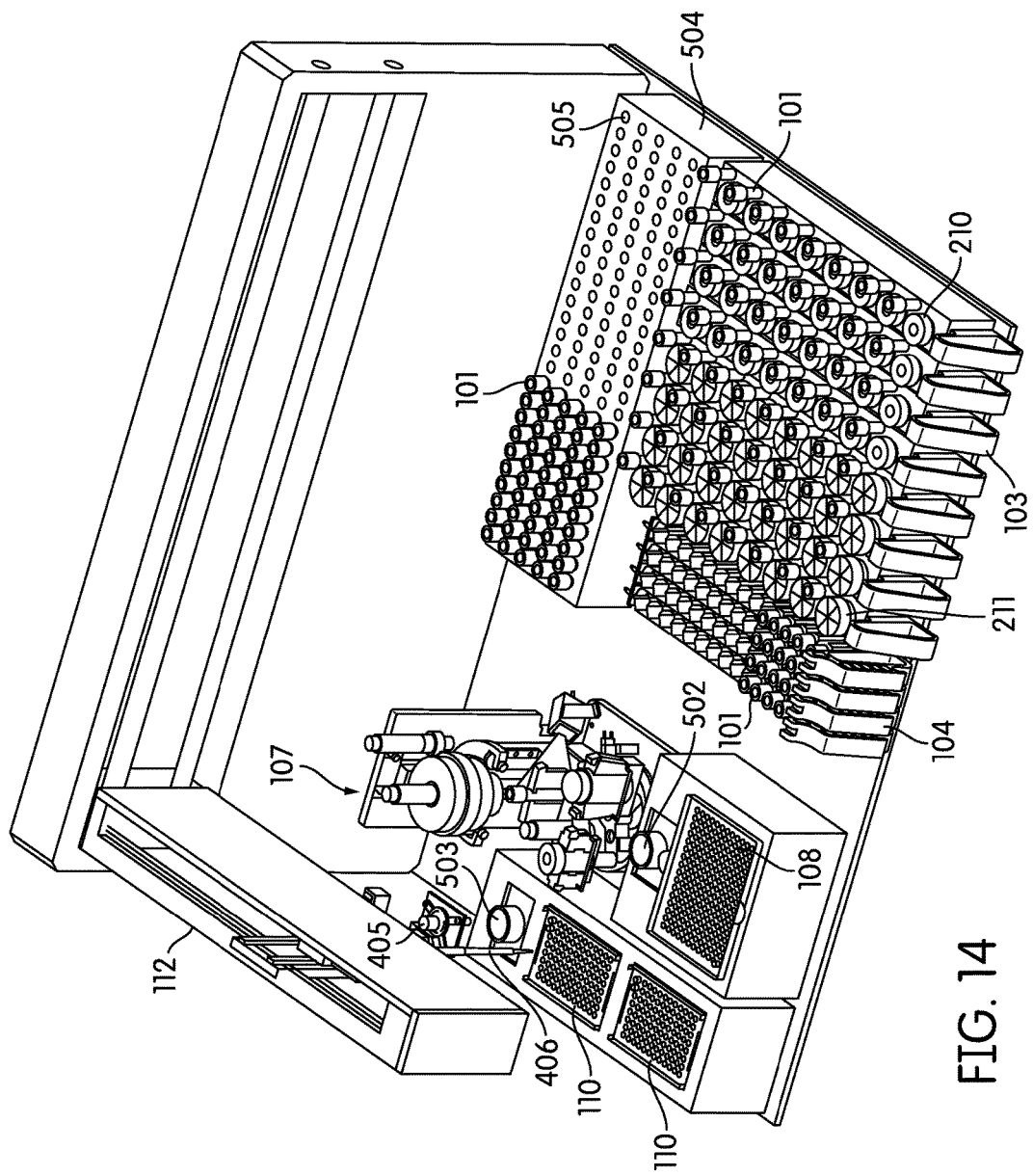
FIG. 14 illustrates an embodiment of a sample processing instrument.
Figure 15:
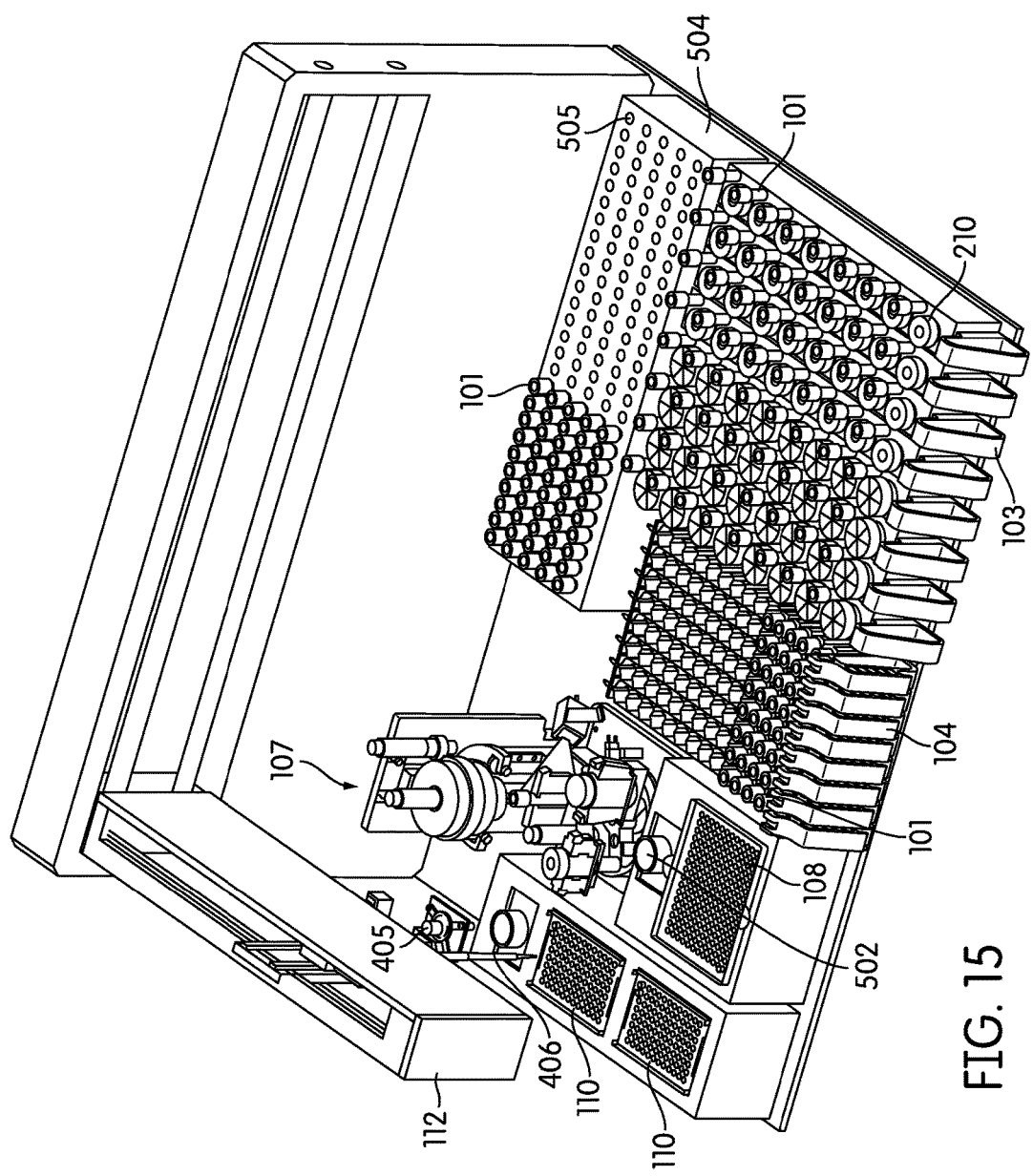
FIG. 15 illustrates another embodiment of a sample processing instrument.
Figure 16:
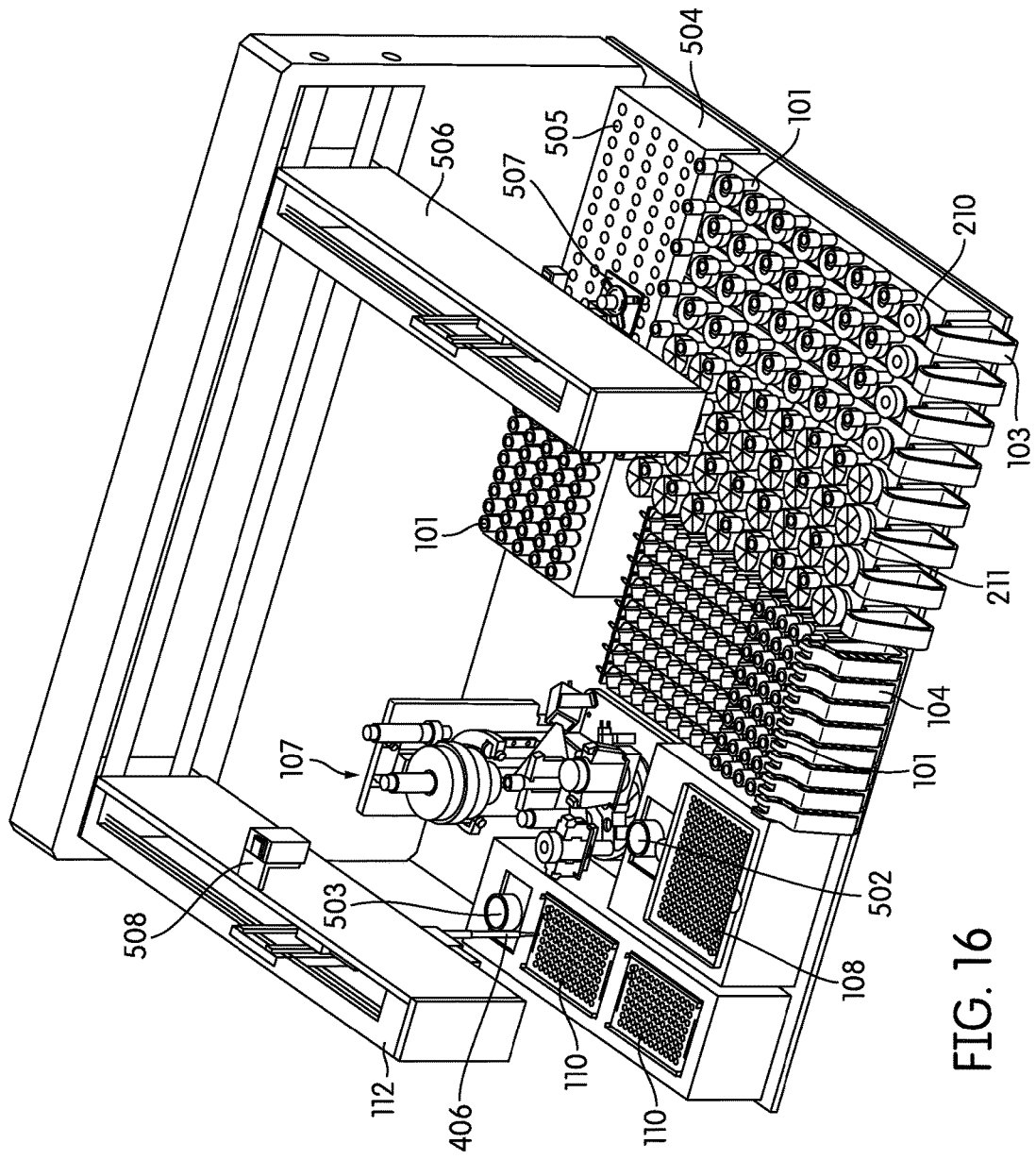
FIG. 16 illustrates another embodiment of a sample processing instrument.
Figure 17:
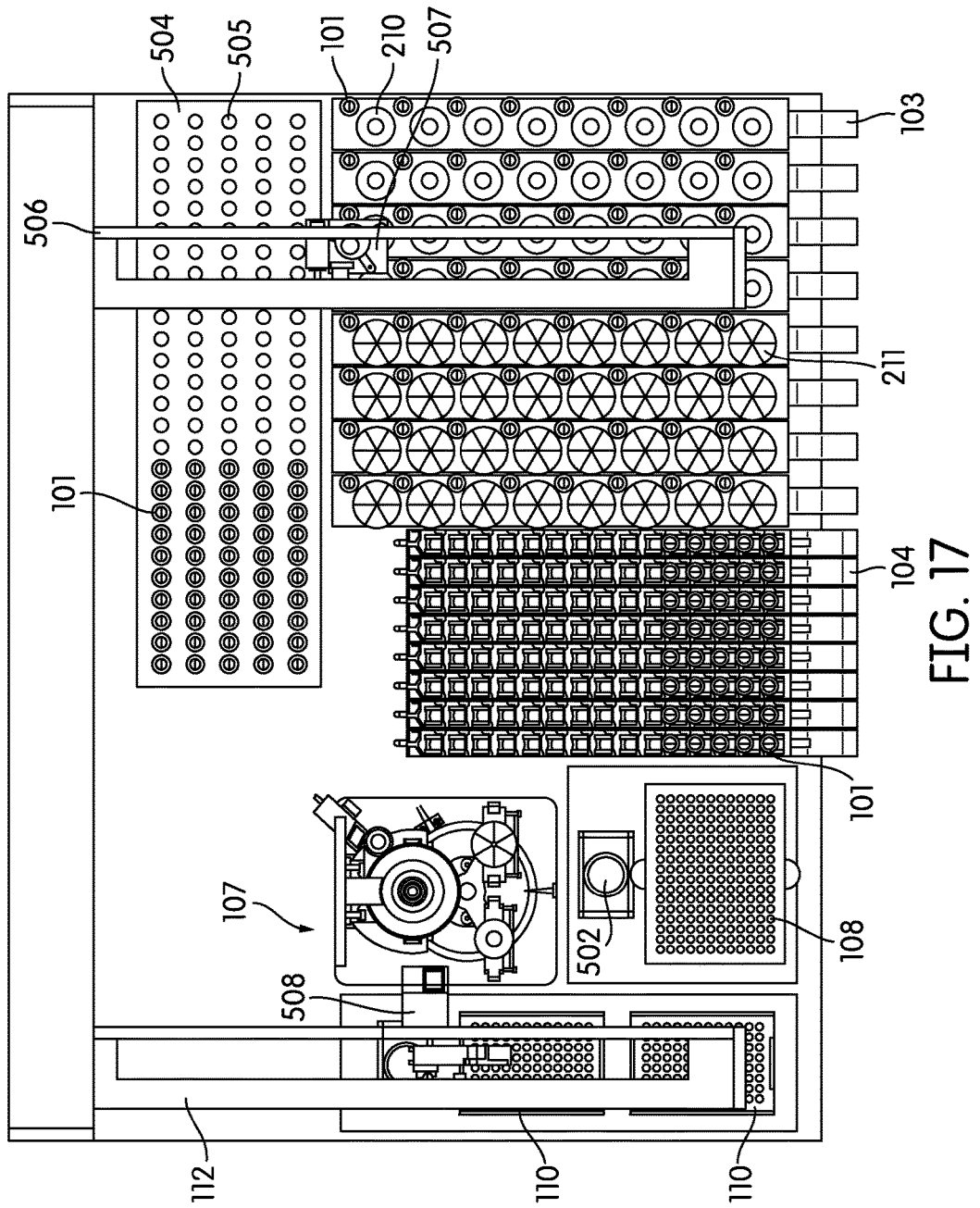
FIG. 17 illustrates a top view of the sample processing instrument of FIG. 16.

Depending on the throughput desired, the number of output racks 104 can vary, for example, between four (as shown in FIG. 14) to eight (as shown in FIGS. 15-17). But in some embodiments, the number of output racks 104 utilized and/or space dedicated to output racks 104 can be less than four output racks 104 or more than eight output racks 104. In some embodiments, output racks 104 can be randomly populated with processing receptacles 101 that have been incubated and processing receptacles 101 that have not been incubated. In some embodiments, the composition of sample types in each output rack 104 can be determined by the type and number of samples processed by the laboratory at any particular time, without requiring sample batching as utilized in output rack 104 incubating embodiments.

In some embodiments as shown in FIGS. 14-17, the automated processing instrument can utilize a steady-temperature incubator 504 such that when a processing receptacle 101 is placed in incubator 504, incubation begins immediately. In such embodiments, each processing receptacle holder 505 of incubator 504 is heated to a particular predetermined temperature and maintained at that temperature regardless of whether a processing receptacle 101 is present or not. In some alternative embodiments, incubator 504 can have cycling capability such that incubator 504 can heat to a predetermined temperature upon, or after, placement of a processing receptacle 101 in a processing receptacle holder 505 of incubator 504. In another embodiment, incubator 504 is partitioned such that portions of incubator 504 may be individually heated, while other portions of incubator 504 remain unheated. The partitions can comprise individual processing receptacle holders 505 such that each processing receptacle holder 505 is individually temperature controlled, or alternatively, the partitions can comprise blocks of processing receptacle holders 505 such that two or more processing receptacle holders 505, for example, about 5, 10, 15, 20, 25, 30, 35, 40, or more processing receptacle holders 505, are temperature controlled as a single unit. In some embodiments, the system controller monitors the incubation timing of each processing receptacle 101 to ensure optimum sample processing in a time-efficient manner without operator intervention.

In some embodiments, as shown in FIGS. 14-17, the automated processing instrument includes 130 processing receptacle holders 505 in incubator 504. In other embodiments, the number of processing receptacle holders 505 in incubator 504 can be more or less than 130, depending on the throughput desired and the incubation time required. For example, if the incubation time is two hours and an individual sample processing time is one minute, the automated processing instrument can include at least about 120 processing receptacle holders 505 in incubator 504. In such embodiments, a processing receptacle 101 can be introduced to the incubator 504 every minute over the course of two hours such that the first introduced processing receptacle 101 completes its incubation and can be removed from incubator 504 to output rack 104 at about the same time the last of the 120 processing receptacle holders 505 is filled. In such configurations, a receptacle holder 505 for a new processing receptacle 101 is always left, which maximizes throughput and minimizes the size of incubator 504. In some embodiments, the automated instrument will include additional processing receptacle holders 505 in incubator 504 in case the receptacle gripper 405 is occupied with other duties, there are no spaces available in output racks 104, or the system overall is occupied, at the time the initial incubation is completed. If the incubation time is less than two hours, the number of processing receptacle holders 505 can be correspondingly decreased to maximize throughout. Correspondingly, if sample processing time is decreased to less than one minute, additional processing receptacle holders 505 in the incubator 504 can be provided such that a processing receptacle 101 can be placed in incubator 504 at any time the initial sample processing in the sample processing station 107 is complete.

FIGS. 14-17 also depict an alternative configuration of a waste bin 108 and liquid waste bin 502, in addition to the consumable area containing pipette tip trays 110 that are configured to hold a plurality of pipette tips used with pipettor 406, and reagent containing receptacle 503, for example, a bottle, that contains a reagent that can be added to a sample.

Although FIGS. 14 and 15 show a single robotic arm 112 having both pipettor 406 and receptacle gripper 405, the automated instrument can include two or more robotic arms, for example, two robotic arms 112 and 506 as depicted in FIGS. 16 and 17. As shown in FIGS. 16 and 17, the automated instrument includes a robotic arm 506 having receptacle gripper 507, and a robotic arm 112 having pipettor 406. In alternative embodiments (not shown), robotic arm 112 includes both pipettor 406 and a receptacle gripper 405, while robotic arm 506 contains a second receptacle gripper 507.

In some embodiments, robotic arm 506 performs all pick and place duties required by the automated instrument. In some embodiments, robotic arm 506 is programmed, by way of the controller, to perform one or more of the following steps: (1) move processing receptacles 101 and sample containing receptacles 102 (for example, sample containing receptacle 210 and 211) between, for example, input racks 103 and sample processing station 107, (2) move sample containing receptacles 102 (for example, sample containing receptacle 210 and 211) from sample processing station 107 to input racks 103, (3) move processing receptacles 101 from processing station 107 to incubator 504, (4) move processing receptacles 101 from processing station 107 to output racks 104, and (5) move processing receptacles 101 from incubator 504 to output racks 104. In some embodiments, the automated instrument uses multiple robotic arms to perform the above steps, which can maximize throughput and permits uninterrupted processing in sample processing station 107.

Process Controls

Ensuring sample processing accuracy and completion is an important aspect of any sample processing process, whether it is manual or automated. In automated processing, however, it can be difficult to determine whether a particular process was carried out, or if it was carried out accurately, since processing often occurs outside the view of the user. Moreover, samples such as biological LBC samples are often complex materials to work with in an automated fashion due to, among other reasons, the frequent occurrence of mucoids, particulates, the risk of contamination between samples, and the presence of specimen collection utensils such as brooms, brushes, spatulas, etc. Mucoids can interfere with sample aspiration and dispense accuracy since they may occasionally hang off the end of a pipette tip of pipettor 406 after sample aspiration. The increased viscosity of mucoids can also occasionally provide a false indication of the true sample volume that has been aspirated. Moreover, a hanging mucoid at the end of a robotic arm operated pipettor tip poses a significant contamination risk as the pipette moves over other sample containing receptacles, processing receptacles, and/or reagent containing receptacle on its way to a waste bin or other location. Particulates can also interfere with sample aspiration and dispense accuracy. For example, particulates can clog the opening of a pipette tip of pipettor 406 and give a false indication of the true volume of an aspirated sample, or prevent aspiration altogether.

In some embodiments, the automated instrument provides a variety of process controls with each sample processing protocol to minimize the chance that an incorrectly processed sample is delivered to the user. For example, at each step in the process, encoders, electro-mechanical flags, liquid level detection, barcode reading, temperature sensors, machine vision, optical sensors, reverse cLLD, and pressure base volume verification, as described herein, are used to ensure that specimen and sample tubes, as well as reagents and the specimens themselves, have successfully completed each step in the processing protocol.

In some embodiments, if a sample processing protocol fails, and the sample cannot be recovered, there are a variety of contemplated options for dealing with such a failure. In one embodiment, if a sample processing fails, processing receptacle 101 is drained by the pipettor and placed in output rack 104. When the sample is later processed on the assay instrument, the empty processing receptacle 101 generates a liquid level or dispensing failure. Since processing receptacle 101 contains the same patient identifying information as its corresponding sample containing receptacle 102, e.g., barcode information, the sample processing failure can be automatically reported to the laboratory information system (LIS). In other embodiments, if a sample processing fails, the processing receptacle 101 is placed in output rack 104, but rotated in a manner that the barcode of receptacle 101 cannot be read. Either the user will observe the lack of barcode, or when the sample is processed on the assay instrument, the assay instrument will determine that the particular pocket of the output rack 104 is empty since the assay instrument will be unable to read identifying information about processing receptacle 101 in that pocket. This empty indication cues the user to report a processing failure to the LIS since the user will identify that a processing receptacle 101 is actually present and that processing receptacle 101 is associated with a particular sample containing receptacle 102. Another embodiment for dealing with sample processing failure is returning the processing receptacle 101 to input rack 103, which optionally leaves an empty slot in output rack 104. Similar to the second embodiment, the user then identifies processing receptacle 101 in input rack 103, and/or the user or assay instrument identifies the lack of processing receptacle 101 in the output rack and reports the sample processing failure to the LIS. As another embodiment, a printer within the sample processing instrument can black-out a barcode present in processing receptacle 101 of a failed sample to ensure that the sample cannot be accidentally processed on a down-stream instrument, for example, an assay instrument.

Ensuring sample identification accuracy is another problem encountered when automating a sample processing process. For example, as the sample is prepared it is transferred between a sample containing receptacle 102 (for example, sample containing receptacles 210 or 211) and a processing receptacle 101. Therefore, it is important to ensure that the sample in processing receptacle 101 is correlated with the sample in sample containing receptacle 102 (for example, sample containing receptacles 210 or 211) so that the sample is processed according to the proper protocol and that the correlation of that sample with the donor patient is maintained. Accordingly, in some embodiments, the automated processing instrument tracks the identification of each sample throughout processing, including following the sample as it is passed from sample containing receptacle 102 (for example, sample containing receptacles 210 or 211) to processing receptacle 101. One exemplary method of tracking this information is to utilize matching barcodes on both sample containing receptacle 102 (for example, sample containing receptacle 210 or 211) and processing receptacle 101. This process maintains sample-to-result positive identification tracking. Utilizing this tracking process can provide an advantage over existing sample processing instruments in that matching the receptacle barcodes and always passing the processing receptacle 101 directly to the assay instrument eliminates the need for an LIS interface. Moreover, this process can simplify the necessary instrument software and tracking process since the downstream assay instrument is generally connected to an LIS.

In some embodiments, the laboratory workflow required to process a sample, for example, a biological LBC samples, requires that both the sample containing receptacle 102 (for example, sample containing receptacle 210 or 211) and processing receptacle 101 have the same barcode containing patient identification. This matching enables assay instruments such as instruments capable of performing hybridization assays, amplification assays, sequencing assays, and/or immunoassays to communicate with the laboratory's LIS.

Some laboratories do not have the capability, or their process flow does not allow them to, print duplicate barcodes. Accordingly, in some embodiments, the user, for example, the laboratory, prints a barcode containing patient identification and applies it to sample containing receptacle 102 (for example, sample containing receptacle 210 or 211). Processing receptacle 101, in turn, contains a preprinted, unique barcode on the receptacle provided by, for example, the receptacle manufacturer. The automated sample processing instrument then reads both the barcode on sample containing receptacle 102 (for example, sample containing receptacle 210 or 211) and the barcode on processing receptacle 101, and the automated processing instrument then creates an association between the two receptacles. This association information is then transferred to the assay instrument via a network connection (e.g., LAN, Ethernet, WiFi, Bluetooth®, ZigBee®, RS232, USB, RF, IR, Firewire®, Thunderbolt®, eSATA, or other network connection). When the assay instrument encounters processing receptacle 101 with patient identification that has an association, the assay instrument then queries or reports patient data against the associated barcode on sample containing receptacle 102 (for example, sample containing receptacle 210 or 211), which is loaded into the LIS.

In alternative embodiments, the same scenario as above may occur, with the exception that the association information is stored in a file on a mobile storage device such as a USB drive or similar. The mobile storage device is then, for example, manually plugged into the assay instrument where the information is transferred to the assay instrument. Alternatively, the association information is occasionally stored in an RFID tag positioned, for example, on output rack 104. In such an embodiment, the RFID tag transmits the information to the assay instrument upon placement in the assay instrument.

Figure 18:
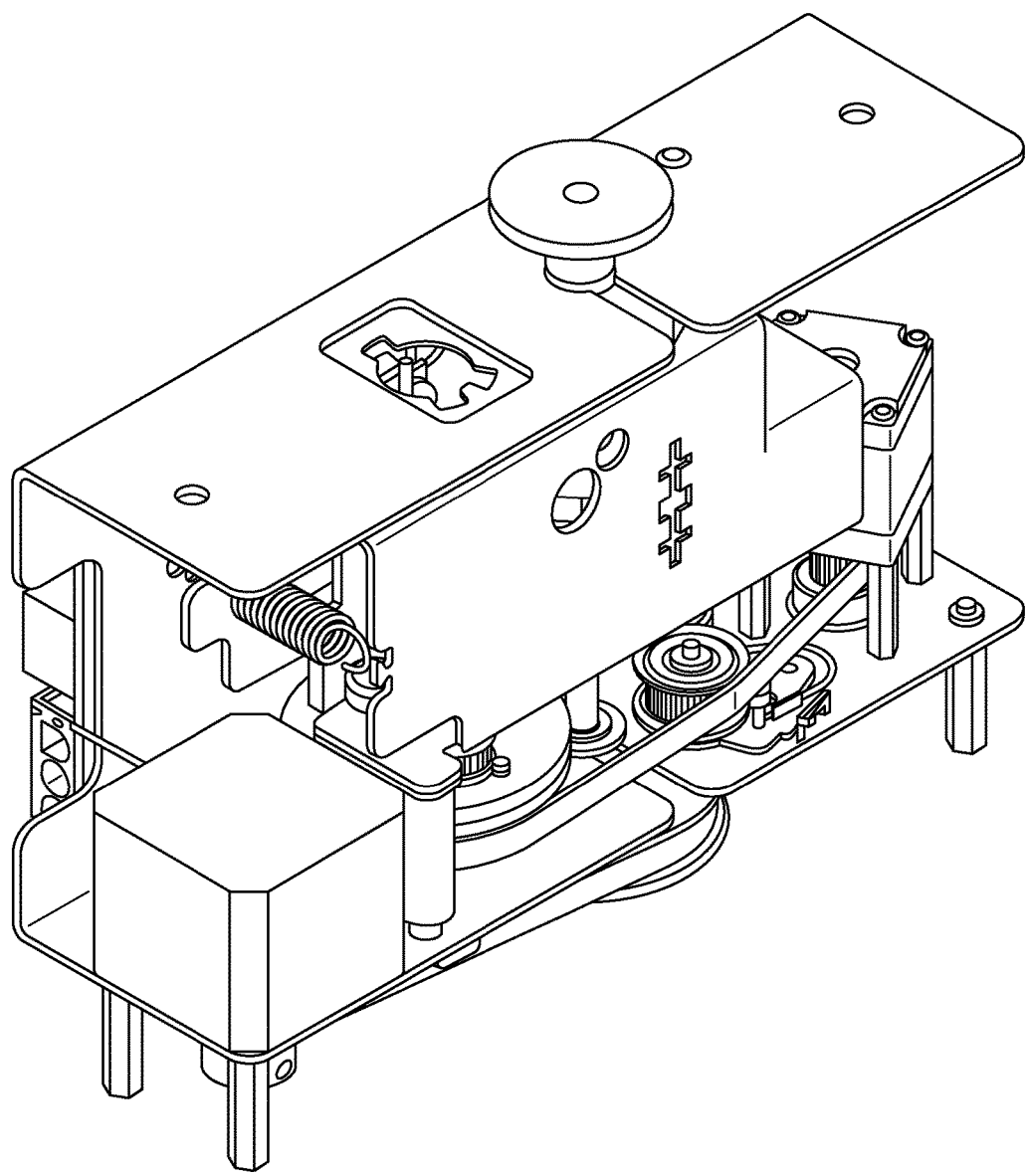
FIG. 18 illustrates an embodiment a printer.
Figure 19:
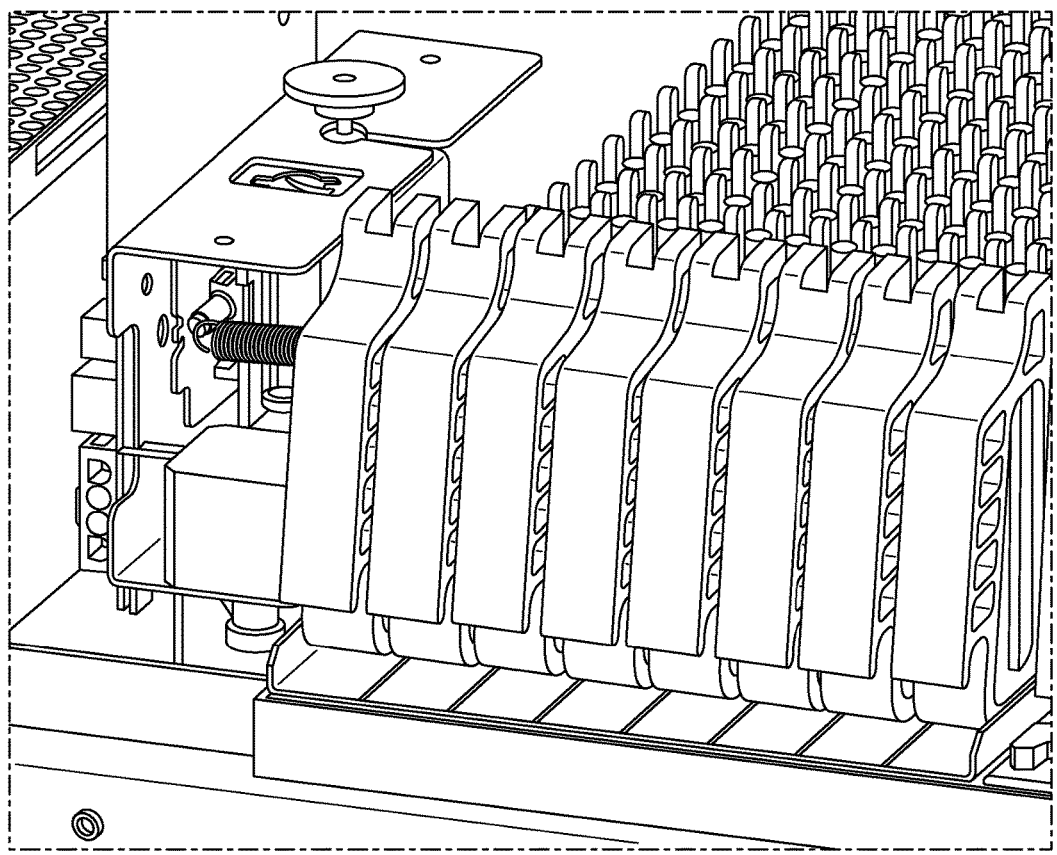
FIG. 19 illustrates an exemplary placement of the printer in a sample processing instrument adjacent to an output rack.

In other alternative embodiments, the user, for example, a laboratory, prints one barcode containing patient identification and applies it to sample containing receptacle 102 (for example, sample containing receptacle 210 or 21). Processing receptacle 101, in turn, contains no label, a blank label, or a different label. The sample processing instrument then reads the barcode of sample containing receptacle 102 (for example, sample containing receptacle 210 or 211), prints the same barcode as contained on sample containing receptacle 102 (for example, sample containing receptacle 210 or 211) (with optional additional metadata in the form of barcode prefixes, suffixes, or similar metadata) and applies the barcode to processing receptacle 101. In some embodiments, the sample processing instrument reads the barcode of sample containing receptacle 102 (for example, sample containing receptacle 210 or 211), and creates the same barcode (with optional additional metadata in the form of barcode prefixes, suffixes, or similar metadata) directly on processing receptacle 101, e.g., by way of printing, imprint, burning, thermal transfer, or another method. Also in some embodiments, a different bar code is printed on processing receptacle 101 containing additional metadata (e.g., time, volume, type, reagents, errors, etc.) related to the processing of the corresponding sample. For example, the automated processing instrument can include a printer that prints barcodes to processing receptacles 101 within the automated instrument. FIG. 18 illustrates a printer according to an embodiment, and FIG. 19 illustrates the printer positioned within an automated processing instrument according to an embodiment. In some embodiments, the printer is any one of the printer embodiments described in U.S. Provisional Application No. 62/066,468, filed Oct. 21, 2014, which is incorporated by referenced in this application.

In some printer embodiments, a sample containing receptacle 102 is moved from an input rack 103 to sample processing station 107 to be processed, for example, using any one of the above described embodiments of a robotic arm having a receptacle gripper. A corresponding processing receptacle 101 is moved from input rack 103 to the printer, for example, using any one of the above described embodiments of a robotic arm having a receptacle gripper. In some embodiments, processing receptacle 101 in input rack 103 includes a blank label or a blank area on the label where a barcode can be printed or applied by the printer. In some embodiments, the printer automatically determines the orientation of processing receptacle 101 received therein and identifies the position to print the barcode on the label. The orientation determination is performed with reference to edges of the label or other indicia contained on the label in some embodiments. The printer can use any known technique for printing a barcode, for example, inkjet, direct thermal, thermal transfer, impact, laser ablation, laser pigment change, or any other known printing methods. In some embodiments, the printer uses thermal transfer printing, which can eliminate the need for extra consumables and reduce contamination risks. After the printer prints a barcode on processing receptacle 101, or otherwise automatically applied, processing receptacle 10 it is moved from the printer to sample processing station 107 for processing, for example, using any one of the above described embodiments of a robotic arm having a receptacle gripper.

In another alternative embodiment, sample containing receptacle 102 (for example, sample containing receptacle 210 or 211) includes duplicate barcodes, or more than one barcode, and the automated sample processing instrument removes one of these barcodes and applies it directly on processing receptacle 101. The automated assay instrument can then directly query the LIS or report to the LIS against the barcode (that includes, for example, patient ID) of sample containing receptacle 102 (for example, sample containing receptacle 210 or 211).

In one embodiment, samples are processed one-at-time in the automated sample processing instrument. For example, when incubation is not required, the next sample does not start its processing until the preceding sample processing is complete. In such an embodiment, the robotic arm receptacle gripper retrieves sample containing receptacle 102 (for example, sample containing receptacle 210 or 211) and processing receptacle 101 from input rack 103. Both receptacles 101 and 102 are moved to sample processing station 107 where, for example, the barcodes of receptacles 101 and 102 passed through a field of view 215 of barcode reader 204 to be read and verified to be a corresponding pair. In an embodiment, the processing of sample containing receptacle 102 begins in sample processing station 107 before arrival of processing receptacle 101. In such an embodiment, processing receptacle 101 can be moved to the printer (see FIGS. 18 & 19) by the receptacle gripper of the robotic arm to print a barcode on processing receptacle 101 before receptacle 101 is moved to sample processing station 107. The barcode printed, or otherwise applied, on processing receptacle 101 may be identical to the barcode on corresponding sample containing receptacle 102 or it may be a different barcode. In some embodiments, a different bar code is printed on processing receptacle 101 that encodes additional metadata relevant to the processing of that particular sample.

Once processing has been completed, a robotic arm moves processing receptacle 101 to output rack 104 and sample containing receptacle 102 (for example, sample containing receptacle 210 or 211) back to input rack 103. All process controls, system status, and user status are logged and associated with the sample barcodes and saved to persistent storage. At any time, the sample processing log can be queried for a specific sample by, for example, barcode, RFID, or exported to a file via, for example, a USB drive or similar.

Figure 12:
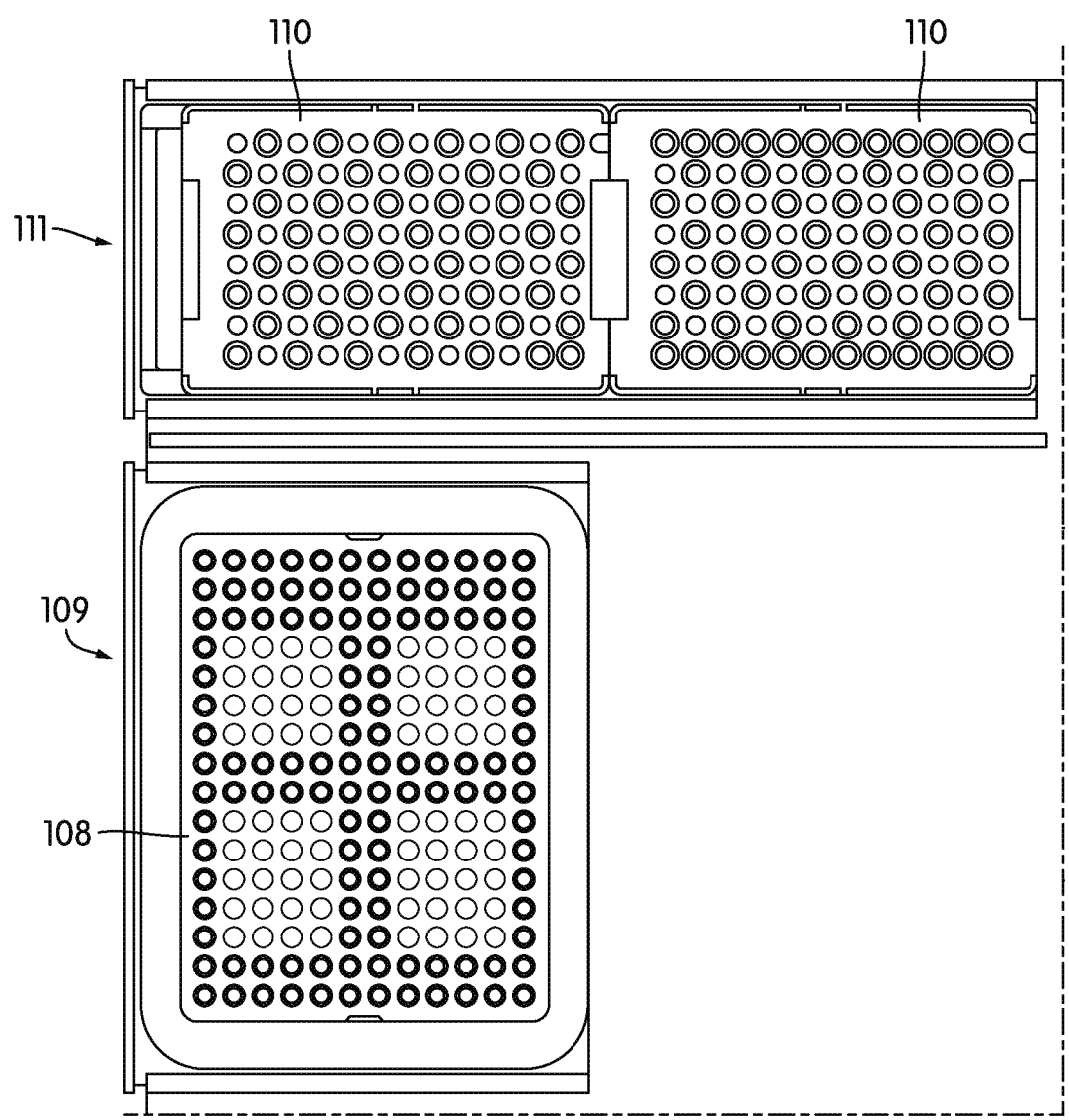
FIG. 12 illustrates a top view of a consumable inventory management system component, according to an embodiment.

In some embodiments, inventory control and monitoring of the automated processing instrument is handled by a set of assumptions, rules, and feedback mechanisms. These assumptions, rules, and feedback mechanism can be complicated, marginally accurate, and time consuming. Accordingly, in some embodiments, the automated sample processing instrument implements a fast, accurate, real-time control and monitoring of onboard inventory that uses machine vision. In some embodiments, each of the inventoried items are visibly available to a set of camera(s) that perform image processing algorithms to determine volume, capacity, or inventory of any onboard consumables, samples, receptacles, and waste materials. For example, in one embodiment, one or more cameras are statically mounted on the instrument frame to provide continuous real-time feedback. Additionally or alternatively, as shown in FIGS. 16 and 17, one or more cameras 508 are mounted on a robotic arm (for example, robotic arm 112 or 506) to provide visual feedback to multiple areas of the automated processing instrument. Although FIGS. 16 and 17 depict a single camera 508 on robotic arm 112, another camera can be positioned on second robotic arm 506. In some embodiments, the automated processing instrument uses special illumination techniques to achieve robust, fast, and accurate visual feedback. For example, the automated instrument can use machine vision inventory control for one or more of the following controls:

1. Pipette Tip & Waste Bin Inventory: A camera 508 can be mounted above the instrument looking onto the instrument deck of the automated instrument (e.g., as shown in FIG. 17). Camera 508 is in optical communication with, and images, the pipette tip trays 110 and waste bin 108. Camera 508 has, for example, onboard image processing capabilities, or is connected to computer or computing apparatus, one or more processors, to conduct image processing, and processes the image and provides a full inventory of all tips held by tip trays 110 and waste bin 108. In one embodiment, the automated processing instrument provides backlight illumination under tips trays 110 and waste bin 108 to reduce the complexity and increase the reliability and speed of the image processing algorithms (see FIG. 12). In one embodiment, tip trays 110 and/or waste bin 108 are made of a translucent material to enhance imaging.
2. Sample Containing Receptacle and Processing receptacle (e.g., LBC Specimen Receptacle Inventory): A camera 508 is mounted above within the instrument looking onto the instrument deck (e.g., FIG. 17). Camera 508 is in optical communication with, and images, the input bay containing input racks 103 holding sample containing receptacles 102 (for example, sample containing receptacles 210 or 211) and processing receptacles 101 to be processed. Camera 508, for example, has onboard image processing capabilities, processes the image, and provides a full inventory of all processing receptacles 101 and sample containing receptacles 102 (for example, sample containing receptacles 210 or 211) present within the input bay. In some embodiments, camera 508 is utilized to determine the types of sample containing receptacles 102 (for example, sample containing receptacles 210 or 211) and/or types of samples contained in the input racks 103, for example, by identifying markings on sample containing receptacles 102 (for example, sample containing receptacles 210 or 211) or sample rack 103, or by visualizing a barcode contained on sample containing receptacles 102 (for example, sample containing receptacles 210 or 211) or sample rack 103.
3. Single Camera Inventory Control: Alternatively, one or more cameras 508 are mounted to an instrument robotic arm (for example, robotic arm 112 or 506). Camera 508 is moved around the instrument deck during routine operation of the robotic arm (for example, robotic arm 112 or 506) or upon special instruction, providing a full inventory of all instrument consumables as in cases (1) and (2) above.

As mentioned above, a common problem with specimens collected from patients is the presence of mucoids. Pipette tips of pipettor 406 can get clogged or pull mucoid strands from the sample or processing receptacle 101 or 102. While clogs can usually be detected with pressure based feedback, mucoid strands may not be detectable. If mucoids are not properly removed, contamination may occur. While shearing mechanisms may work, they may not guarantee mucoid removal. Accordingly, in some embodiments, the automated sample processing instrument includes a mucoid strand detection device. For example, in some embodiments, the automated sample processing instrument has mucoid strand detection device (e.g., a camera 509 in FIG. 2) that uses machine vision to visually inspect the pipette tip of pipettor 406 immediately after a specimen aspiration and before the pipette tip has been moved away from the sample containing receptacle 102. The vision system can include a camera with onboard image processing algorithms that notify the instrument controller as to whether or not a mucoid strand is present.

In some embodiments, the automated instrument includes a second layer of mucoid detection. For example, pipettor 406 can optionally be configured to perform reverse capacitive Liquid Level Detection (cLLD). Reverse cLLD detects a change in capacitance of the pipette tip. When the pipette tip is removed from the specimen liquid, cLLD reports a step change in capacitance. This step change occurs at the liquid level of the specimen (the liquid level is accurately detected before aspiration). If the step change is delayed or there is no step change, a mucoid may be present.

When a mucoid strand is detected by either or both processes, pipettor 406 fully dispenses the sample back into sample containing receptacle 102 (for example, sample containing receptacle 210 or 211) and re-attempts the aspiration. In some embodiments, the position of pipettor 406 can be altered within the sample containing receptacle 102 to a new aspiration location to avoid mucoids. If after multiple retries, mucoid strands are still detected, sample containing receptacle 102 can be vortexed, and the aspiration process can be repeated. This process can provide a significant guard against contamination versus conventional shearing mechanisms since no mucoid strands leave the sample containing receptacle 102 (for example, sample containing receptacle 210 or 211). Furthermore, this method requires little or no maintenance, so routine instrument cleaning requirements are reduced.

In some embodiments, the automated sample processing instrument contains one or more of the following process controls to ensure accurate and complete sample processing:
1. Positive sample identification using barcode reader 204 to read sample containing receptacles 102 and processing receptacles 101 in sample processing station 107.
2. Consumable inventory control of all consumables, for example, solid waste bin 108, input racks 103, output racks 104, and incubator 504 inventory, which can identify the number and type of preparations remaining (e.g., camera-based).
3. Reagents volumes, for example, in reagent containing receptacle 503, confirmed and tracked by liquid level sense and/or LLD.
4. Liquid in waste bin (502) volume tracking by LLD or counting dispenses.
5. Detection of pipettor tip retention and ejection.
6. Confirmation of sample delivery by liquid level sense and/or Pressure Dispense Volume Verification via RDV.
7. Confirmation of reagent delivery by liquid level sense and/or Pressure Dispenser Volume Verification via RDV.
8. Mix verification by sensing mechanical motion using sensors and/or encoders.
9. Thermal monitoring of all temperature sensitive modules.
10. Encoder feedback to ensure proper robotic motion.
11. Machine vision mucoid detection.
12. Sensors to detect different sample types (e.g., input racks).
13. Positive ID verification and barcode printing for processing receptacles in the instrument.

In some embodiments, the automated sample processing instrument contains one or more of the following process controls to minimize the risk of contamination:
1. Filtered disposable pipette tips on tip trays 110.
2. Cleanable specimen input racks 103.
3. Cleanable output racks 104.
4. Cleanable consumable drawer 111.
5. Disposable waste bins or waste bin covers 108 and 502.
6. Cleanable drip tray.
7. Specimen mucoid removal track.
8. Barriers between the tip drawer 111, sample racks 103, and processing station 107.
9. Controlled airflow to keep aerosols moving from clean to less clean side of instrument.
10. Easily cleanable surfaces and tracks.
11. Instrument covers to protect from splashing the operator.
12. Machine vision and reverse cLLD confirmation of sample aspiration and mucoid detection.

Since the instrument is capable of concurrently processing multiple sample types, some requiring reagent addition and heated incubation and others not requiring incubation, it is important to ensure proper thermal management. In this regard, in one embodiment, the automated sample processing instrument often contains one or more of the following items:
1. Four or more incubators 105 servicing four or more output racks 104; alternatively a single incubator 504 is provided, servicing all processing receptacles 101 to be incubated.
2. Multiple temperature sensors that provide precision incubator temperature control and redundancy.
3. Controlled airflow.
4. Insulated incubators (105 or 504) that inhibit heat transfer to other parts of the instrument containing processing receptacles 101 that are not to be incubated, sample containing receptacles 102, and reagents (503).

Throughput

In some embodiments, the automated instrument is a high-throughput, random access sample processing instrument capable of simultaneously processing multiple different sample types. As indicated, the instrument automatically processes samples according to a rule set that balances throughput with time-to-next-result, which is particularly relevant when the instrument is processing different types of samples that require different routines and reagents. For example, in one embodiment, the instrument is designed to process up to about 540 samples that do not require incubation, or up to about 360 samples that require reagent addition and heated incubation within a single eight hour shift. Included in this time is instrument setup, run preparation, sample processing, clean up and instrument power down. For purposes of this discussion, a "run" is defined as the processing of up to about sixty samples, for example, LCB specimens, from start to finish. In other embodiments, a run can include processing more or less than sixty samples, depending on the number of available input lanes in the input bay and output lanes in the output bay of the machine. For example, a run could refer to the processing of up to about ninety-six samples, for example, LCB specimens, from start to finish. In one embodiment, a run refers to processing a collection of samples that occupy a defined portion or all of the available input lanes of the input bay or that occupy a defined portion or all of the available output lanes of the output bay.

In some embodiments, the sample processing protocol does not require incubation (e.g., processing ThinPrep® samples). In some embodiments, this protocol takes about 1 minute of processing time per specimen, and thus, the instrument can process up to 9 runs (e.g., 540 samples) in an 8 hour shift. In such embodiments, the time to first result is about 1 minute for a single specimen or approximately 15 minutes to prepare a full output rack having 15 pockets.

In another embodiment, the protocol takes about 30 seconds of processing time per sample, and thus can process up to 18 runs (e.g., 1080 samples) in an eight hour shift. In such embodiments, the time to first result is approximately 30 seconds for a single sample or approximately 7.5 minutes to prepare a full output rack having 15 pockets.

The specimen processing time can depend on the type of processing required and the sample type being prepared. The overall sample processing protocol can vary over a range of time, for example processing of a single sample may range from 30 seconds to 2.5 hours (if incubation is required). In some embodiments, the sample processing time may range between 30 seconds and 2 minutes. In another embodiment the sample processing time may range between about 1 to about 2 minutes. If an incubation is required, often sample processing time will range from about 1 hour to about 2.5 hours.

Figure 4:
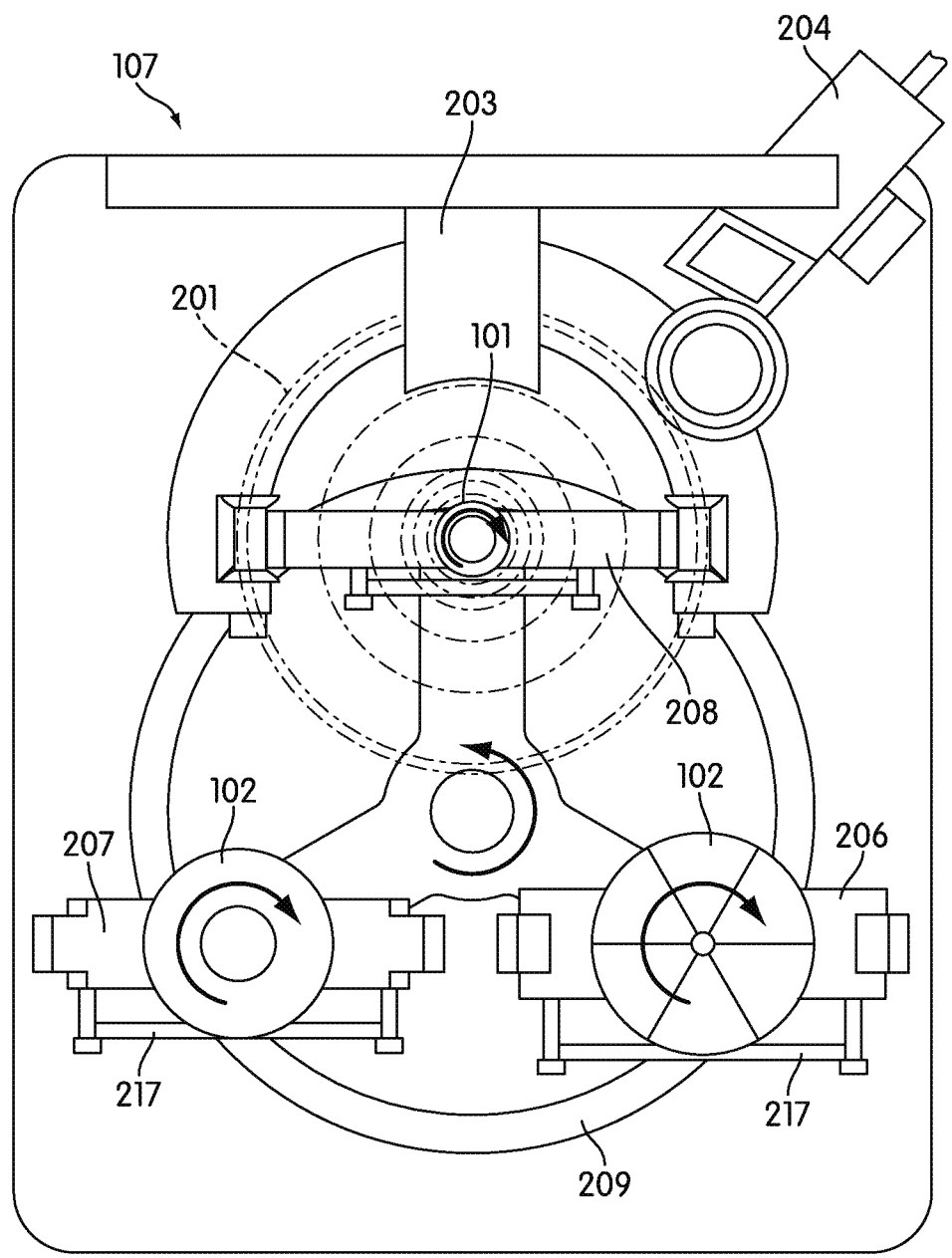
FIG. 4 illustrates a top view of the sample processing station showing exemplary rotational directions of the carousel, sample containing receptacles, and processing receptacle, according to an embodiment.
Figure 5:
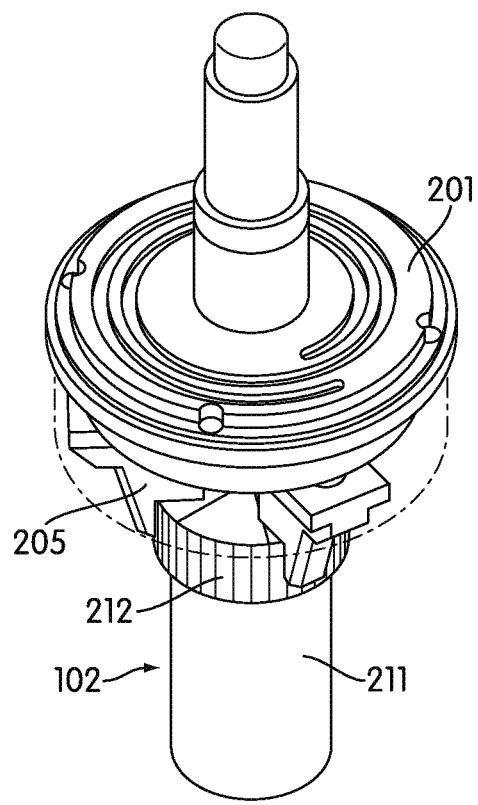
FIG. 5 illustrates a perspective view of a capping and decapping mechanism, according to an embodiment.
Figure 6:
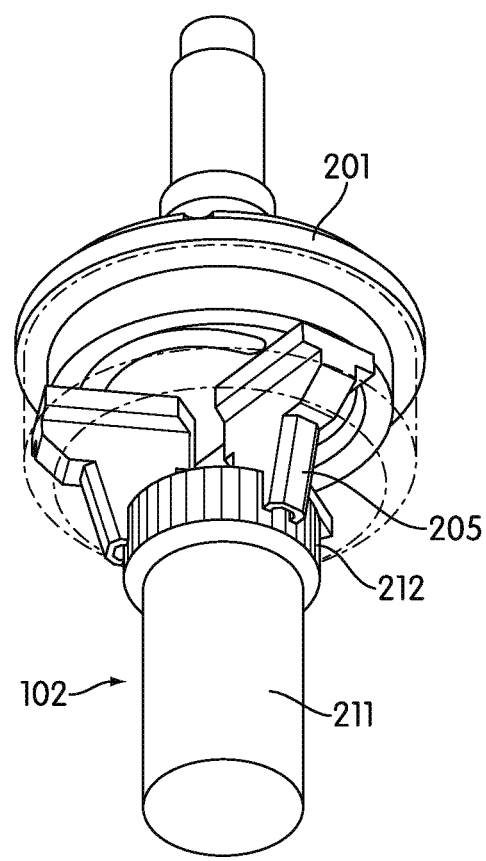
FIG. 6 illustrates another perspective view of a capping and decapping mechanism, according to an embodiment.

In some embodiments, the flow of processing of a Thin-Prep® sample contained within sample containing receptacle 211, irrespective of concurrently conducted process controls, is the following:
1. Using a robotic arm having a receptacle gripper, pick sample containing receptacle 211 from input rack 103 and place in corresponding container holster 206 on a carousel 209 in processing station 107;
2. Read a barcode on sample containing receptacle 211 using barcode reader 204;
3. Orbital mix the sample in sample containing receptacle 211 (see arrows in FIG. 4);
4. If necessary, using a robotic arm having a receptacle gripper, pick corresponding processing receptacle 101 from input rack 103 and place in the printer (see FIGS. 18 & 19) for printing a barcode (or other machine readable label) on processing receptacle 101;
5. Using a robotic arm having a receptacle gripper, pick corresponding processing receptacle 101 from the printer (see FIGS. 18 & 19) and place in processing receptacle holster 208 on carousel 209 in processing station 107;

6. Rotate sample containing receptacle 211 under elevator 203 holding a capping/decapping mechanism 201 such that a chuck 205 grasps cap 212 (see also FIGS. 5 & 6);
7. Uncap ThinPrep® receptacle 211;
8. Using elevator 203, move cap 212 and chuck 205 upward, permitting carousel 209 to rotate without hitting cap 212;
9. Swing a drip tray 202 under the chuck 205 and cap 212;
10. Rotate sample containing receptacle 211 to a service position (for example, the positioning depicted for receptacle 211 in FIG. 2);
11. Using pipettor 406, aspirate a sample from sample containing receptacle 211;
12. Move pipettor 406 over liquid waste bin 502;
13. Rotate sample containing receptacle 211 under capping/decapping mechanism 201 and chuck 205;
14. Move drip tray 202 out of way of chuck 205 and cap 212;
15. Using elevator 203, move capping/decapping mechanism 201 holding cap 212 and chuck 205 downward onto sample containing receptacle 211;
16. Withdraw drip tray 202;
17. Recap sample containing receptacle 211;
18. Move elevator 203 up to allow carousel 209 to rotate;
19. Rotate processing receptacle 101 under capping/decapping mechanism 201;
20. Lower elevator 203 such that chuck 205 grasps and removes processing receptacle cap 216;
21. Using elevator 203, move cap 216 and chuck 205 upward; 22. Swing drip tray 202 below cap 216 and chuck 205;
23. Move drip tray 202 under cap 216 and chuck 205;
24. Rotate processing receptacle 101 to the service position;
25. Using pipettor 406, dispense the sample into processing receptacle 101;
26. Rotate processing receptacle 101 under capping/decapping mechanism 201 and chuck 205;
27. Withdraw drip tray 202 as elevator 203 moves cap 216 and chuck 205 downward onto processing receptacle 101 to recap the processing receptacle 101;
28. Recap processing receptacle 101;
29. Using a robotic arm with a receptacle gripper, move sample containing receptacle 211 to input rack 103;
30. Using a robotic arm with a receptacle gripper, processing receptacle 101 is moved to output rack 104.

In one embodiment, the flow of processing of a SurePath® sample contained within sample containing receptacle 210, irrespective of concurrently conducted process controls, is the following:
1. Using a robotic arm with a receptacle gripper, pick sample containing receptacle 210 from input rack 103 and place in corresponding container holster 207 on carousel 209 in processing station 107;
2. Read a barcode on sample containing receptacle 210 using barcode reader 204;
3. Orbital mix the sample in sample containing receptacle 210 (see arrows in FIG. 4);
4. If necessary, using a robotic arm having a receptacle gripper, pick corresponding processing receptacle 101 from input rack 103 and place in the printer (see FIGS. 18 & 19) for printing a barcode (or other machine readable label) on processing receptacle 101;
5. Using a robotic arm having a receptacle gripper, pick corresponding processing receptacle 101 from the printer (see FIGS. 18 & 19) and place in processing receptacle holster 208 on carousel 209 in processing station 107;
6. Rotate sample containing receptacle 210 under elevator 203 holding capping/decapping mechanism 201 such that chuck 205 grasps cap 213 (see also FIGS. 5 & 6);
7. Uncap sample containing receptacle 210;
8. Using elevator 203, move cap 213 and chuck 205 upward, permitting the carousel 209 to rotate without hitting cap 213;
9. Swing drip tray 202 under chuck 205 and cap 213;
10. Rotate sample containing receptacle 210 to the service position (e.g., the positioning depicted for receptacle 211 in FIG. 2);
11. Using pipettor 406, aspirate predetermined amount of sample processing reagent (e.g., FASTEXPRESS® reagent, available from Gen-Probe Incorporated, San Diego, Calif.) from reagent containing receptacle 503;
12. Using the same pipette tip as step 11, or selecting a new pipette tip, on pipettor 406, aspirate a sample from sample containing receptacle 210;
13. Move pipettor 406 over liquid waste bin 502;
14. Rotate sample containing receptacle 210 under capping/decapping mechanism 201 and chuck 205;
15. Using elevator 203, move capping/decapping mechanism 201 holding cap 213 and chuck 205 downward onto sample containing receptacle 210;
16. Withdraw drip tray 202;
17. Recap sample containing receptacle 210;
18. Move elevator 203 up to allow carousel 209 to rotate;
19. Rotate processing receptacle 101 under capping/decapping mechanism 201;
20. Lower elevator 203 such that chuck 205 grasps and removes processing receptacle cap 216;
21. Using elevator 203, move cap 216 and chuck 205 upward;
22. Swing drip tray 202 below cap 216 and chuck 205;
23. Rotate processing receptacle 101 to the service position;
24. Using pipettor 406, dispense the sample into processing receptacle 101;
25. Rotate processing receptacle under capping/decapping mechanism 201 and chuck 205;
26. Withdraw drip tray 202 as elevator 203 moves cap 216 and chuck 205 downward onto processing receptacle 101 to recap the vessel;
27. Recap processing receptacle 101;
28. Using a robotic arm with a receptacle gripper, move sample containing receptacle 210 to input rack 103;
29. Optionally, mixing processing receptacle 101;
30. Using a robotic arm with a receptacle gripper, move processing receptacle 101 to output rack 104, incubator 105, or dedicated incubator 504 for incubation;
31. If processing receptacle 101 is positioned in dedicated incubator 504, using a robotic arm with a receptacle gripper, move processing receptacle 101 from incubator 504 to output rack 104 after incubation.

In some embodiments, one or more of the above processes can occur simultaneously. The above automated protocols are provided by way of example only such that modifications of the number of steps, what happens in each step, and the number of processes occurring in a particular order or simultaneously may be changed or altered without affecting the subject matter of this disclosure.

One of skill in the art would appreciate that the processing time required to process each sample has a direct effect on the number of samples that can be prepared in a given time period. Manipulation of the processing time may have a detrimental impact on processing accuracy and can increase the risk of contamination, though a variety of sample processing times are contemplated with the caveat that downtime between sample processing is kept to a minimum.

Sample processing protocols that incorporate a reagent addition and/or incubation step (e.g., processing SurePath® samples) are slightly more complicated than non-reagent or non-incubation protocols. In the case of processing Sure-Path® samples a reagent addition step and an incubation step are required to fully prepare a sample. The rate limiting step for SurePath® samples can be the incubation time for samples requiring incubation. For example, a two-hour sample incubation at 65° C. will affect the overall throughput of the automated instrument. Instrument downtime can be minimized and throughput can be maximized in batches of samples containing samples requiring incubation by reducing incubation times (e.g., down to about one hour), increasing the number of samples incubated at any given time, and/or reducing the number of pockets in the output rack 104.

The sample incubation time can vary. For example, in the case of an LBC sample, the incubation time can be about 15 minutes, about 30 minutes, about 45 minutes, about 60 minutes, about 75 minutes, about 90 minutes, about 105 minutes, or about 120 minutes. The incubation temperature can vary as well. For example, the incubation temperature can be at or about 37° C., at or about 65° C., or between about 37° C. and 65° C. In some embodiments, the incubation time may be at or about 90° C., or between about 37° C. and 90° C. In some embodiments, the incubation temperature is above or below 65° C. In some embodiments requiring incubation in output racks 104, the automated instrument will generally fully populate an output rack 104 with, e.g., fifteen samples, before the incubation process is started. In such an embodiment, the processing time can be about 1 minute and 30 seconds, or about a minute, or about less than one minute per sample before the incubation step.

In some embodiments that provide incubation of processing receptacles 101 in a dedicated incubator 504 (rather than in the sample output rack 104) having about 120 incubation processing receptacle holders 505, high throughput rates can be maintained because incubation may begin when a processing receptacle 101 is positioned in incubation processing receptacle holders 505 of incubator 504, without having to wait until an output rack 104 is fully populated. The sample processing instrument, for example, can be configured to monitor the incubation time of each processing receptacle 101 contained in dedicated incubator 504. Similarly, in such an embodiment, a large number of samples can be incubated at any particular time without commandeering output rack space 104, thus permitting a continuous flow of non-incubated samples from input racks 103 while concurrently processing samples requiring incubation. Although the processing time for any particular batch (e.g., a full output rack 104 of, for example, fifteen samples) of incubated samples occasionally does not decrease through the use of a dedicated incubator, throughput advantages are realized since output rack use flexibility is maximized. For example, any particular output rack 104 can be populated with samples contained within processing receptacles 101 that have been incubated and those that have not been incubated. In such embodiments involving an output rack 104 having, for example, fifteen pockets, these pockets can be filled with up to fifteen processing receptacles 101 that have been incubated and up to fifteen processing receptacles 101 that have not been incubated. In such circumstances, it is unnecessary to await the completion of the incubation of the fifteen processing receptacles 101 to fill an output rack 104, rather rack 104 can be populated with any number of processing receptacles 101 that have completed their incubation, while the remaining pockets in the output rack 104 are filled with non-incubated processing receptacles 101. Accordingly, in some embodiments, the sample processing instrument is capable of processing one sample per minute during the entirety of an eight-hour work day, excluding instrument startup and shutdown time, regardless of whether the samples require incubation or not.

Varying the incubation time, the number of pockets in a sample output rack 104, and/or permitting partial filling an output rack 104 will correspondingly affect the time to completion of one or more samples, including a batch of samples. For example, if the incubation time is reduced from two hours, the number of incubation processing receptacle holders 505 can be decreased while maintaining a similar throughput. Unless specifically indicated, embodiments are not limited to a specific incubation time, amount of samples in a sample input rack 103, number of sample input rack pockets in input rack 103, number of pockets in an output rack 104, number of incubators 105 or 504, number of robotic arms, number of receptacle grippers, or number of sample processing stations.

In some embodiments, the automated processing instrument is modular such that the number of incubator slots can be altered to more or fewer than one hundred and twenty. In addition, the sample processing instrument may be outfitted with additional sample input lanes in the input bay or output lanes in the output bay, for example 4, 5, 6, 7, 8, or more input or output lanes, which permits increased walk-away time by the user while increasing system throughput.

In one embodiment, the automated processing instrument is designed to process any combination of sample racks 103 containing samples requiring and not requiring incubation at any time, while minimizing dead time. This feature allows the user random access to the automated instrument in batches of 1-8 specimens (an exemplary number of specimens held in an input rack 103). The instrument software will balance time to next result and throughput based on a defined set of rules, taking into account the incubation time required for the samples in the system. In one embodiment, the sample processing rules include the following: (1) finish loading current output rack 104, (2) process all samples requiring incubation up to incubation, and (3) process all samples not requiring incubation. Often in such embodiments, output rack 104 may be populated with incubated and non-incubated samples, depending on how many samples completed their incubations while output rack 104 was being populated. For example, in one embodiment, when a sample completes incubation, it is immediately transferred to the next available pocket in output rack 104, whether it is an empty or partially filled output rack 104. The time period between incubation completion and transfer to output rack 104 may be limited by, for example, the availability of the receptacle gripper and robotic arm of the instrument to effect such a transfer.

As noted, the instrument can be designed to maximize throughput regardless of the type of sample being processed. The embodiments and examples discussed herein are provided by way of illustration only. As noted, the number of input and output lanes (including number of incubators) can be decreased or increased in a manner that will affect overall throughput, with the limiting factors comprising incubation time and processing time within sample processing station 107. Accordingly, in one embodiment, the instrument one or more sample processing stations 107 together with, optionally, a correspondingly increased number of input lanes and incubator slots and robotic arms containing a pipettor and/or receptacle gripper. In such configurations, the throughput will increase versus the examples discussed above, but at the expense of a larger bench-top footprint in some embodiments.

In some embodiments, another limiting factor to increasing throughput is the overall footprint of the instrument. Often laboratory space is very limited such that only smaller, bench-top style instruments can be accommodated. Embodiments fulfill this need by providing a fully automated sample processing solution in a compact package. As such, it is an object of embodiments to provide a compact instrument capable of automated sample processing of multiple sample types. For example, in one embodiment the instrument is a bench-top instrument.

Capacity

In some embodiments, the consumable and liquid/solid waste capacity can dictate the maximum number of processed samples the instrument can process before specimen processing is stopped and consumables are reloaded and waste is removed. In one embodiment, the consumables and waste bins (for example, tip trays 110 and bins 108 and 502) are sized for processing a maximum of ninety six samples. In another embodiment, the consumables and waste bins (for example, tip trays 110 and bins 108 and 502) are sized for processing a maximum of 192 samples. In yet another embodiment, the consumables and waste bins (for example, tip trays 110 and bins 108 and 502) are sized to accommodate the number of samples and volume of liquid and solid waste generated in a full shift of use of the instrument, such as processing up to about 540 samples.

Waste bin 502 can be used in the event that a sample processing fails, where the failed sample is discarded in waste bin 502. In addition, in one embodiment, waste bin 502 can act as a drip catch for caps removed from sample containing receptacles 102 (for example, sample containing receptacle 210 or 211) and pipette tips containing sample or reagent. In one embodiment, this drip catch can be utilized during the period of time it takes the sample processing station carousel 209 to rotate to the service position (for example, the positioning depicted for receptacle 211 in FIG. 2) for sample aspiration or dispense using pipettor 406. In another embodiment, a drip catch or drip tray 202 is included as a component of the sample processing station 107. In another embodiment, the drip catch or drip tray comprises a portion that is in fluid communication with the liquid waste bin 502 and another portion capable of positioning below (a) a cap removed from a sample containing receptacle 102, or (b) a pipette tip containing sample or reagent. In some embodiments, the liquid waste bin 502 is configured to have a capacity to hold all the liquid waste generated in a single shift or a single day of operation.

In some embodiments, input racks 103 are sized to hold up to about eight sample containing receptacles 102 (for example, sample containing receptacles 210 or 211) in addition to eight processing receptacles 101. In some embodiments, the instrument includes an input bay configured to receive up to eight input racks 103 for a total of 64 sample containing receptacles 102. To run 540 samples that do not require additional reagents or incubation, the eight sample input racks 103 are loaded nine times, for example. In embodiments where samples require additional reagent and incubation, input racks 103 are loaded six times to process 360 sample, for example. In some embodiments, the input racks 103 can be locked within the input bay so the user cannot move the input racks 103 during operation as described further below.

In some embodiments, the instrument includes an output bay sized to receive at least four or up to about eight output racks 104, each capable of holding, for example, fifteen processing receptacles 101 for a total of 120 processing receptacles 101. In some embodiments, the instrument is configured to require that output racks 104 have top covers 304, if otherwise part of output rack 104, removed while being inserted within the output bay of the instrument, which permits loading of processing receptacles 101 into racks 104. In some embodiments, processing 540 samples involves removing 36 output racks 104, and processing 360 samples involves removing 24 output racks 104 over the course of a shift. In some embodiments, the output racks 104 can be locked within the input bay so the user cannot move the input racks 103 during operation as described further below.

In some embodiments, the instrument has one or more drawers or cabinets dedicated to consumables and waste. For example, one or more drawers can be configured to hold one or more pipette tip trays 110 holding pipette tips, for example, two trays of 96 pipette tips, and one or more drawers can be configured to hold one or more receptacles 503 containing a reagent. For example, pipette tip trays 110 can be loaded onto the consumable drawer along with one or more reagent containers 503 required for samples requiring additional reagent. In some embodiments, the instrument can include a barcode reader (not shown) in optical communication with the consumable drawer such that, when the drawer is closed or consumables are placed in the cabinet, one or more of the consumables are then scanned to determine various information about the consumable, for example, lot number, expiration date, total volume, volume remaining, type of reagent, etc. In other embodiments, the consumables are scanned before closing the cabinet or drawer. In such embodiments the particular consumable, for example, the reagent containing receptacle that contains a reagent, will contain a barcode encoding the necessary or desired information.

In some embodiments, reagent containing receptacle 503 will generally have sufficient volume of reagent to process at least 96 samples, or at least about 120 samples, or at least about 190 samples, or up to about 360 samples, requiring additional reagent (e.g., SurePath® samples). Additional reagent containing receptacles, or a larger reagent containing receptacle, may alternatively be incorporated. For example, in one embodiment the reagent containing receptacle 503 will generally have sufficient volume to process at least all of the samples in a shift, or multiple shifts. In some embodiments, the consumable drawer or cabinet is often locked so the user cannot inadvertently open it during operation.

Preparing and Loading the Instrument

In some embodiments, the first step in preparing the instrument for a run is to service the consumable drawer. In one embodiment, the instrument will display the number of remaining samples that it can process before requiring replenishment of reagents (for example, reagent in receptacle 503), pipette tips (for example, tips in tip tray 110), emptying of waste bins 108 or 502, shifting processing receptacles 101 to an output rack 104, replacement of input racks 103, and/or replacement of output racks 104. If the number of remaining samples to be processed is less than the desired number of preparations to be performed, the consumable drawer will often be accessed and loaded or emptied. The instrument is then capable of tracking what pipette tips have been used and how many tips are left, for example, by use of machine vision. See FIG. 12, for example. The reagent containing receptacle 503 is, in one embodiment, monitored by a liquid level sensor to determine the number of remaining preparations that can be performed with the remaining reagent. In one embodiment, the liquid level detection functionality of the pipettor 406 is utilized to monitor the amount of reagent remaining in the reagent containing receptacle 503. With regard to solid waste, waste bin 108 can be emptied each time the waste bin drawer is opened.

The next step in one embodiment is to apply matching barcode labels to sample containing receptacles 102 (for example, sample containing receptacles 210 or 211) and processing receptacles 101 and load them into the appropriate sample input rack 103. Once all input racks 103 have been loaded, the user inserts them into the input bay of the instrument. In one embodiment, machine vision is utilized to detect the receptacle positions in each rack 103 that are populated to provide a full inventory of input racks 103 in the instrument.

In another step of an embodiment, output racks 104 are inserted into an output bay of the automated processing instrument. In some embodiments, the output racks 104 have their top cover 304 removed (if present) and also are empty. In an exemplary embodiment, machine vision is utilized to check or verify whether output racks 104 are empty. For example, if a newly inserted output rack 104 is not empty, the instrument will notify the user.

In another step of an embodiment, machine vision is utilized to track the inventory of incubator 504. Machine vision, therefore, can accurately determine, at any given time, the inventory of the instrument, including the incubator 504, input racks 103, output racks 104, solid waste bin 108, and tip trays 110 in some embodiments.

Instrument Fluidic Management

In some embodiments, the automated processing instrument incorporates a variety of measures and devices to ensure controlled fluid management. For example, in one embodiment, the instrument has a single robotic arm 112 with a pipettor 406 that utilizes both capacitive and pressure based fluid detection (LLD) and pressure based aspiration/dispense verification (RDV). In such an embodiment, a precision dry syringe pump is used to accurately aspirate and dispense volumes from, for example, 25 to 1000 µL. The syringe pump can include a rotary encoder to verify the motor has not stalled or failed. Built into the pump between the syringe and the pipette tip can be a pressure transducer that records the pressure waveform when dispensing or aspiration occurs. Characteristics of the curve are used to verify dispensing or aspiration process (RDV). A conductive pipette tip can be attached to the syringe pump through a stainless steel interface that conducts an oscillating current and used to measure changes in capacitance. When the pipette tip touches fluid, the capacitance changes and can be detected through the liquid level detection (LLD) circuitry.

The fluid levels in the reagent containing receptacles 503 can be detected with LLD, and the volume is calculated based on the known receptacle geometry. The reagent containing receptacles 503 can be keyed in such a way that it cannot be mixed up with other receptacles within the system.

In some embodiments, waste fluid is removed from failed processing receptacles 101 and placed in the liquid waste bin 502 using pipettor 406. In such embodiments, the targeted processing receptacles 101 will be liquid level detected to determine the amount of liquid to be removed. Using pipettor 406, liquid waste will be aspirated from processing receptacle 101 and dispensed into the liquid waste bin 502. The level of the liquid waste bin 502 can also be measured by LLD to notify the user when servicing is required.

Locking Movable Holding Structures within the Automated Instrument

In some embodiments as explained above, the automated sample processing instrument includes one or more movable holding structures (e.g., input racks 103, output racks 104, and drawers 109 and 111) that are configured to hold one or more sample processing devices (e.g., processing receptacles 101, sample containing receptacles 102, pipette tips on trays 110, reagent containing receptacles 503, waste bins 108 and 502) and that are movable within the automated instrument. In some embodiments, the automated instrument is configured to lock one or more of the movable holding structures within the automated instrument to prevent the structures from moving within the automated instrument at various points during sample processing. For example, an input rack 103 can be locked within the instrument when receptacle gripper 405 of robotic arm 408 is picking a sample containing receptacle 102 or processing receptacle 101 from input rack 103. And for example, an output rack 104 can be locked within the instrument when receptacle gripper 405 of robotic arm 408 is placing a processing receptacle 101 in output rack 104. And for another example, consumable drawer 111 can be locked within the automated instrument when pipettor 406 is loading a pipette tip from pipette tip tray 110 held by drawer 111, or when pipettor 406 is aspirating reagent from reagent containing receptacle 503 held by drawer 111. And for yet another example, consumable drawer 109 can be locked within the automated instrument when a pipette tip of pipettor 406 of robotic arm 112 or 407 is inserted within waste bin 108 or 502. In such locking embodiments, locking the movable holding structures within the automated processing instrument can help ensure proper positioning of the movable holding structure during sample processing and helps prevent damage to the movable components of the automated processing system.

In some embodiments, the automated processing instrument includes a lock configured to move between a locked configuration and an unlocked configuration. At the locked configuration, the lock engages the movable holding structure, securing the holding structure within the automated instrument. At the unlocked configuration, the lock disengages the movable holding structure, allowing the movable holding structure to move within the automated instrument. In some embodiments, the lock is engaged or disengaged—moved between the locked configuration and the unlocked configuration—using a robotic arm. And in some embodiments, the robotic arm that actuates the lock is the same robotic arm that moves one or more sample processing devices within the automated processing instrument, for example, robotic arm 112 or 408 having a receptacle gripper 405. Various embodiments of locks for securing movable holding structures within the automated instrument are described below.

Locking Input Racks

Figure 20:
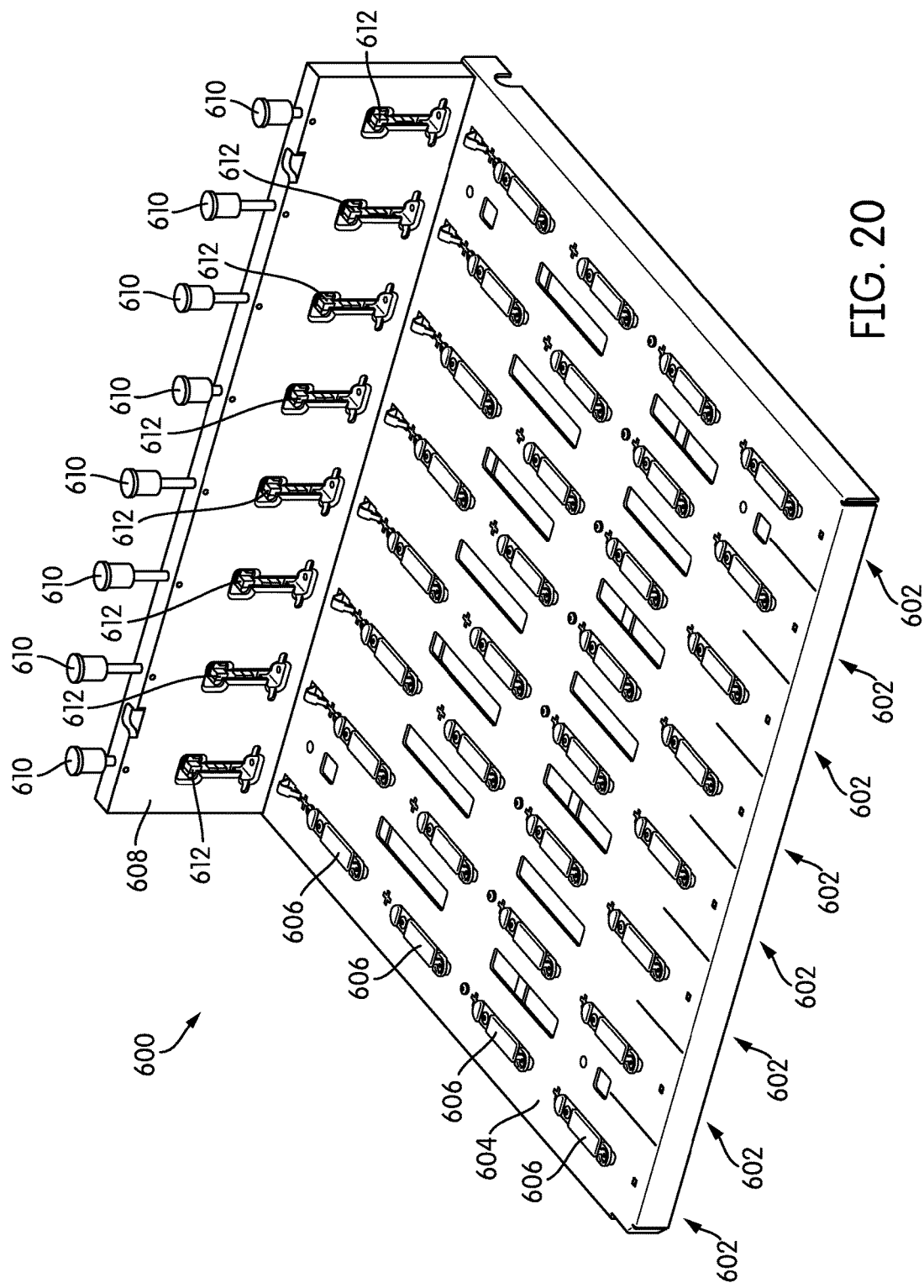
FIG. 20 illustrates a front perspective view of an input bay of a sample processing instrument, according to an embodiment.

In some embodiments, the automated instrument is configured to lock input racks, for example, input racks 103 and input racks 624 described below, within the automated instrument. FIG. 20 illustrates an input bay 600 of the automated processing instrument configured to lock input racks within the instrument according to an embodiment. Input bay 600 is configured to movably receive a plurality of input racks, for example, input racks 103 and input racks 624 described below. Input bay 600 defines a plurality of lanes 602 for slidably engaging the plurality of input racks. For example, input bay 600 can define eight lanes 602 for slidably receiving eight input racks. In other embodiments, input bay 600 defines more or less than eight lanes 602 for slidably receiving more or less than eight input racks. Each lane 602 can include one or more guides 606 extending from a panel 604 of input bay 600. In some embodiments, panel 604 is planar. Guides 606 are configured to be slidably received within a corresponding recess on an opposing surface of the input racks.

In some embodiments, input bay 600 also includes a panel 608 extending, for example, perpendicularly, from panel 604. In some embodiments, the surface of panel 608 facing lanes 602 is planar. In some embodiments, panel 608 stops the insertion of the input racks, for example, input racks 103 and input racks 624 described below, within input bay 600 and, thus, defines the fully inserted position of the input racks 103 for sample processing.

Input bay 600 can also include a plurality of locks for locking corresponding input racks, for example, input racks 103 and input racks 624 described below, within input bay 600 during sample processing. Each lock is configured to move between a locked configuration that engages and secures a corresponding input rack within the automated instrument and an unlocked configuration that disengages and allows the corresponding input rack to move within the automated instrument. For example, in some embodiments, each lock comprises a locking pin 610. In some embodiments, locking pins 610 are movably coupled to panel 608. For example, in some embodiments, locking pins 610 are slidably coupled to panel 608 such that locking pins 610 translate in a direction parallel to panel 608 and perpendicular to panel 604.

Figure 21:
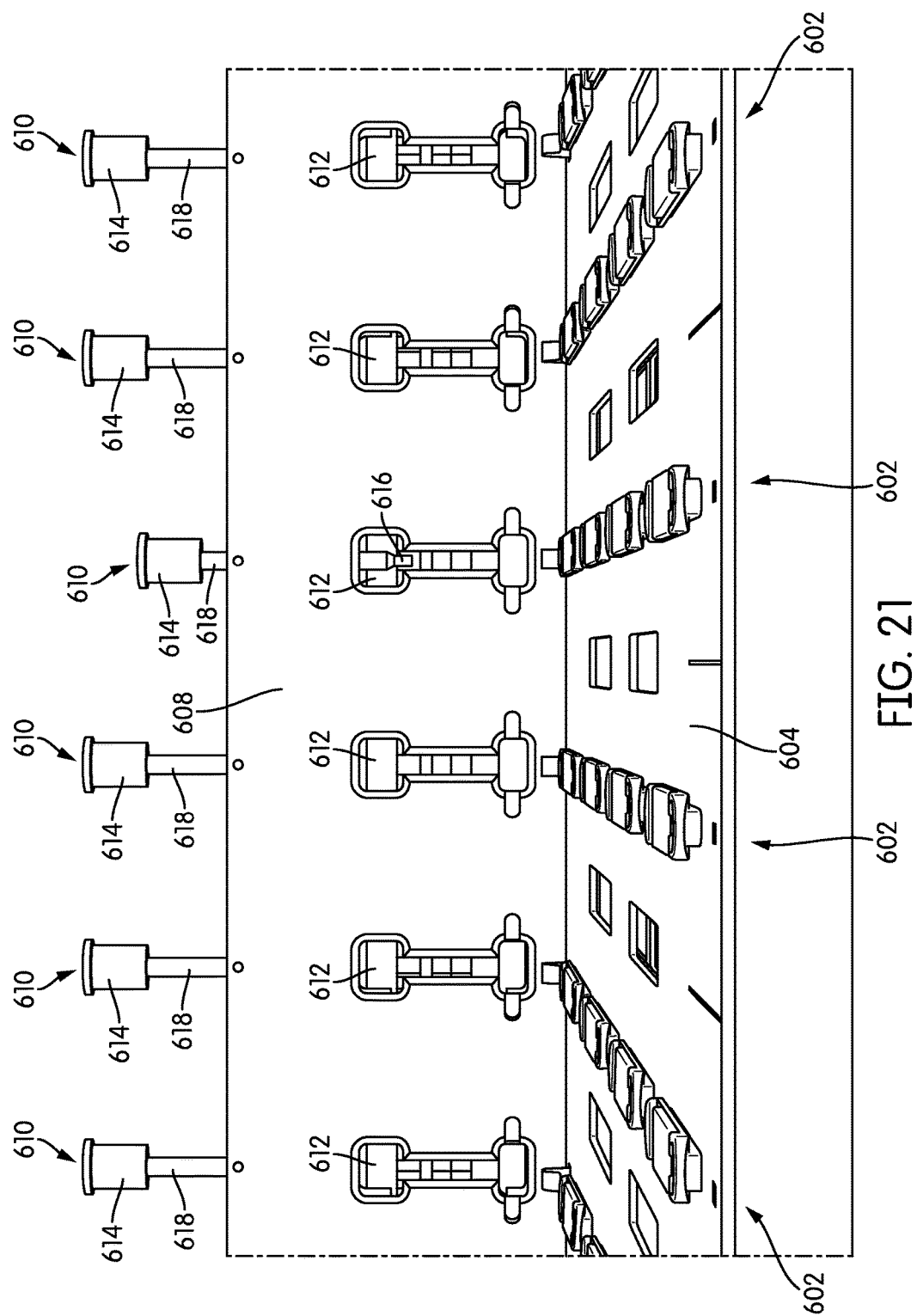
FIG. 21 illustrates a partial front view of the input bay of FIG. 20, according to an embodiment.
Figure 22:
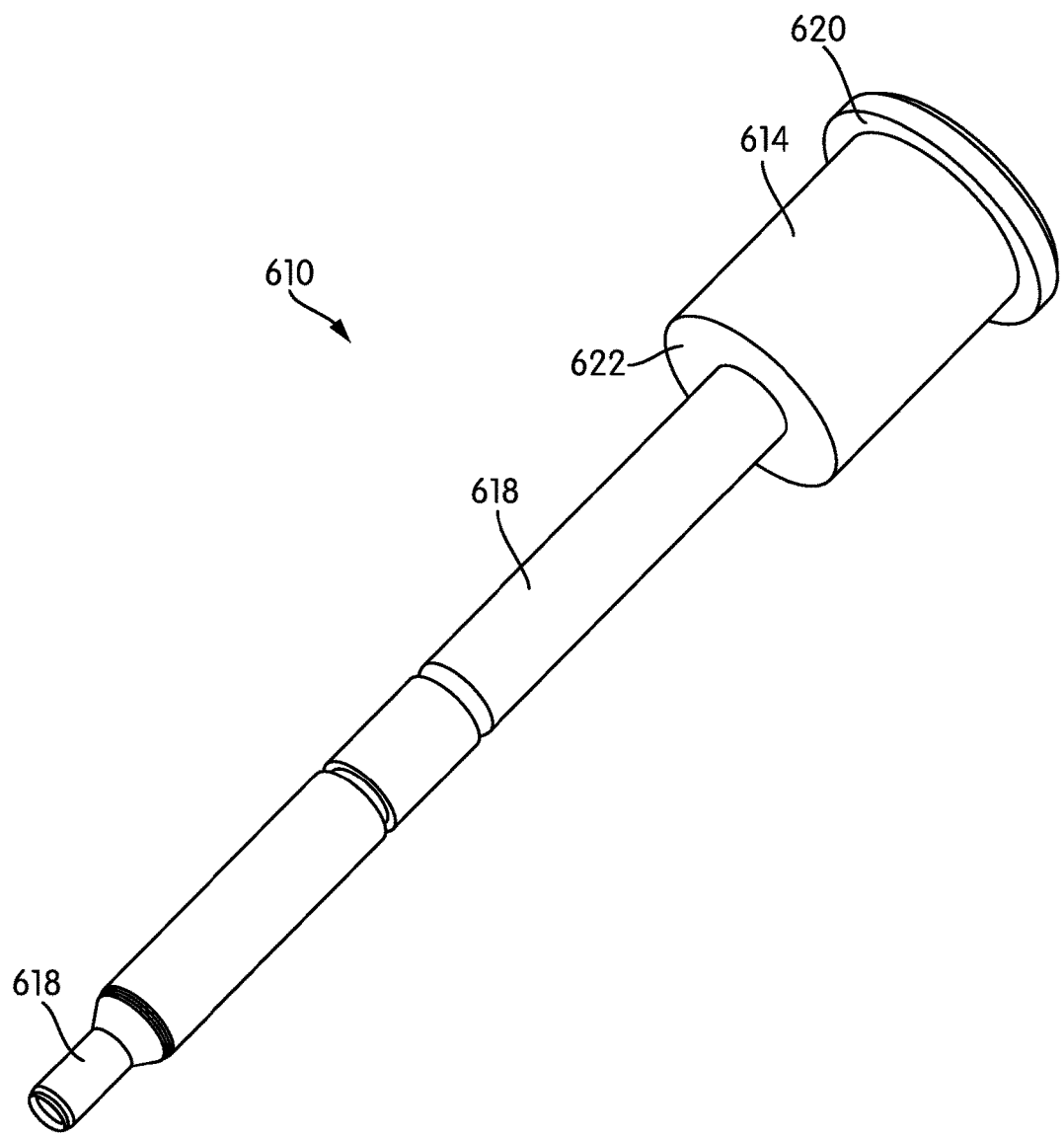
FIG. 22 illustrates a perspective view of a locking pin of an input bay of a sample processing instrument, according to an embodiment.

FIGS. 20-22 illustrate an embodiment of locking pin 610. In some embodiments, each locking pin 610 includes a first end portion 614, a second end portion 616, and an intermediate portion extending between first end portion 614 and second end portion 616. As best seen in FIGS. 20 and 21, locking pin 610 is coupled to input bay 600 such that first end portion 614 extends beyond panel 608 in a direction away from panel 604. First end portion 614 can be cylindrical as shown in FIGS. 20-22. First end portion 614 can include a flange 620 extending from the main body portion of first end portion 614, and first end portion 614 can have a width greater than a width of intermediate portion 618, defining a shoulder 622 at the interface of first end portion 614 and intermediate portion 618. In some embodiments, intermediate portion 618 is elongated and cylindrical as best seen in FIG. 22. And in some embodiments, second end portion 616 defines at least one prong. As shown in FIG. 22, second end portion 616 defines a single prong that is coaxial with intermediate portion 618 (and first end portion 614).

In other embodiments (not shown), locking pin 610 can be configured similar to locking pin 710 described below.

Referring to FIGS. 20 and 21, panel 608 of input bay 600 defines a plurality of openings 612 in some embodiments. The number of openings 612 corresponds to the number of locking pins 610 and lanes 602, in some embodiments. And in some embodiments, each lane 602 has a corresponding locking pin 610. In other embodiments (not shown), one or more lanes 602 may not have a corresponding locking pin 610 or opening 612.

Each locking pin 610 is movably coupled to panel 608 such that each locking pin 610 moves between a locked configuration (for example, in FIG. 21, the configuration of the third locking pin 610 from the right) and an unlocked configuration (for example, in FIG. 21, the configuration of all the locking pins 610 except for the third locking pin 610 from the right). At the locked configuration, the second end portion 616 of the respective locking pin 610 occludes opening 612 as shown in FIG. 21 in some embodiments. And at the unlocked configuration, the second end portion 616 of the respective locking pin 610 does not occlude opening 612 as shown in FIG. 21, in some embodiments. In some embodiments, locking pins 610 are configured such that the second end portions 616 engage input racks, for example, input racks 103 and input racks 624 described below, at the locked configuration, preventing the input racks from moving within input bay 600 of the automated instrument. This configuration secures the input racks within the automated instrument. In some embodiments, locking pins 610 are configured such that the second end portions 616 disengage the input racks, for example, input racks 103 and input racks 624 described below, at the unlocked configuration, allowing the input racks to move within input bay 600 of the automated instrument.

Figure 23:
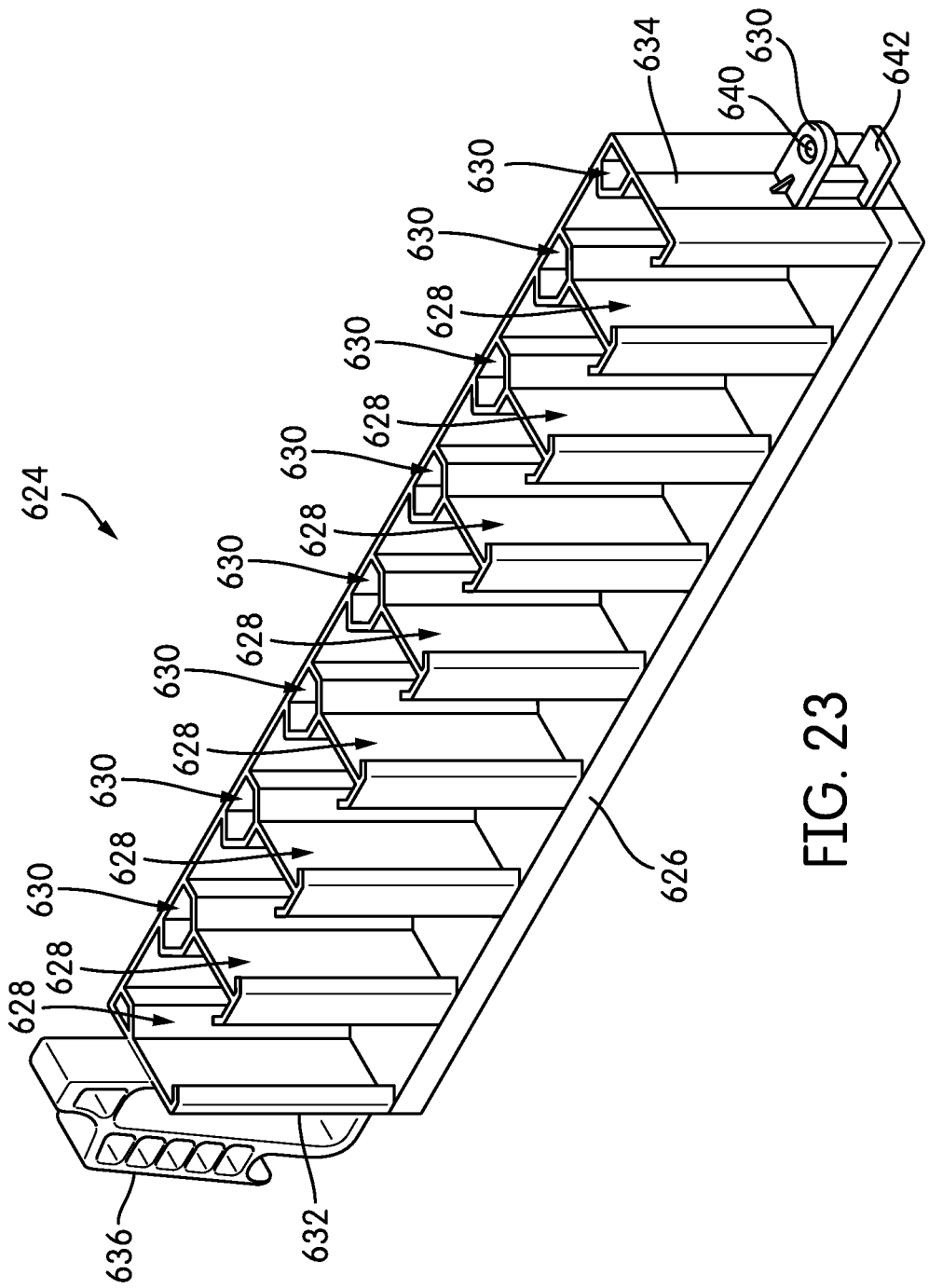
FIG. 23 illustrates a perspective view of an input rack, according to an embodiment.
Figure 24:
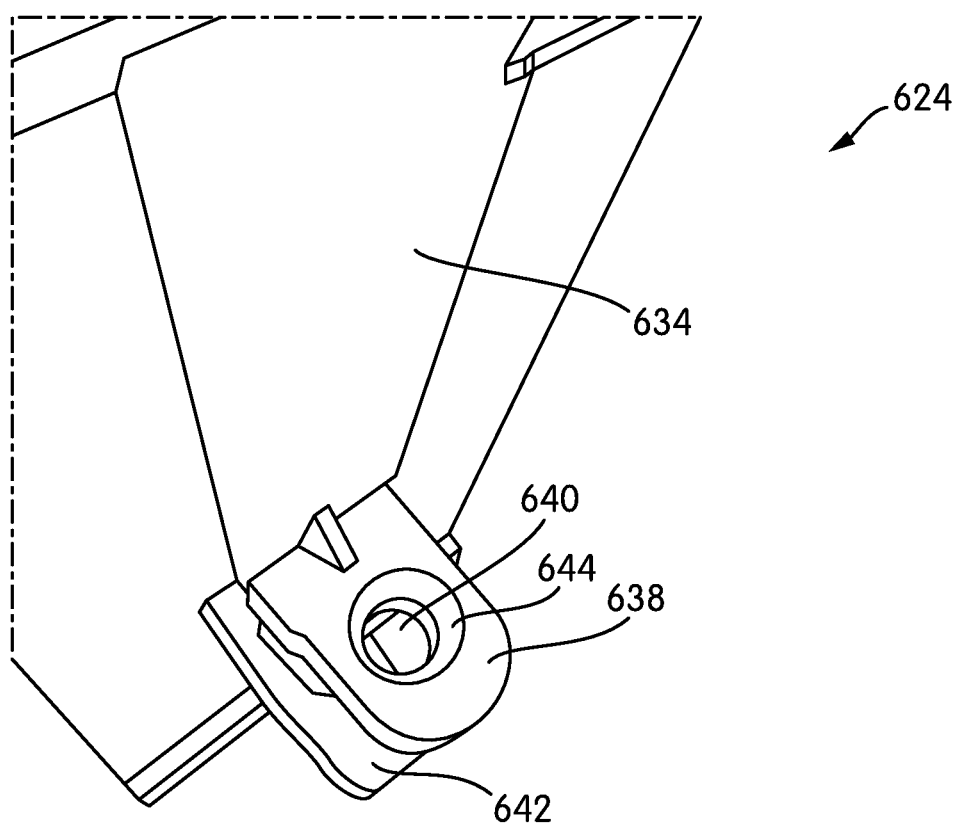
FIG. 24 illustrates a perspective view of a distal portion of an input rack, according to an embodiment.

FIGS. 23 and 24 illustrate an input rack 624 according to an embodiment. In some embodiments, input rack 624 is configured and functions as described above with reference to input racks 103. For example, input rack 624 is configured to hold a plurality of sample containing receptacles 102 and a plurality of processing receptacles 101. As shown in FIGS. 23 and 24, input rack 624 includes a main body 626 that defines a first plurality of pockets 628 configured to receive a plurality of sample containing receptacles 102 and defines a second plurality of pockets 630 configured to receive a corresponding plurality of processing receptacles 101. At a first end portion 632, input rack 624 can include a handle 636 configured to allow a user to grasp and move input rack 624. For example, a user can grasp handle 36 and move input rack 624 along a lane 602 defined by input bay 600.

In some embodiments, input rack 624 defines a recess configured to receive the prong of second end portion 616 of locking pin 610 when locking pin 610 is at the locked configuration. In some embodiments, the recess can be a recessed cavity (such as a recessed pocket) or an opening such as through hole. For example, input rack 624 includes a tab 638 that extends from a surface of rack 624 at a second end portion 634 of rack 624. Tab 638 can define the recess configured to receive the prong of second end portion 616 of locking pin 610 when locking pin 610 is at the locked configuration in some embodiments. In some embodiments, the recess of rack 624 can be a recessed pocket or a through hole. For example, as shown in FIG. 24, tab 638 defines a through hole 640. In some embodiments, a surface 644 of tab 638 defining hole 640 is tapered. In some embodiments, this tapered surface 644 can help align rack 624 within input bay 600. For example, if hole 640 is not aligned with the prong of second end portion 616 of locking pin 610, the prong will slidably engage tapered surface 644 and move rack 624 to the proper position for subsequent sample processing.

In some embodiments, input rack 624 also includes a second tab 642 that extends from a surface of rack 624 at second end portion 634 of rack 624. Second tab 642 is configured to help ensure proper alignment of input rack 624 by mating with a corresponding opening (for example, opening 612) in panel 608 of sample input bay 600.

In some embodiments, opening 612 is configured to receive both tab 638 and tab 642 of input rack 624 when second end portion 634 of input rack 624 abuts panel 608 of input bay 600. For example, as shown in FIGS. 20 and 21, opening 612 is I-shaped such that tab 638 is received in the upper crossbar of the I-shape and tab 642 is received in the lower crossbar of the I-shape. In other embodiments, opening 612 can have any other suitable shape for receiving tabs 638 and 642.

In use, the user aligns input rack 624 with the desired lane 602 and then inserts rack 624 into input bay 600 until second end portion 634 of rack 624 abuts panel 608 of input bay 600. At this point, locking pin 610 is at the unlocked configuration, and tab 638 defining hole 640 extends into opening 612 defined by panel 608. Next, in some embodiments, a robotic arm moves locking pin 610 from the unlocked configuration to the locked configuration such that the prong at end portion 616 of locking pin 610 occludes opening 612 defined by panel 608 and is received within hole 640 of tab 638 of rack 624—locking pin 610 engages rack 624. At this point, locking pin 610 secures rack 624 within input bay 600, preventing movement of rack 624 within input bay 600.

Figure 25:
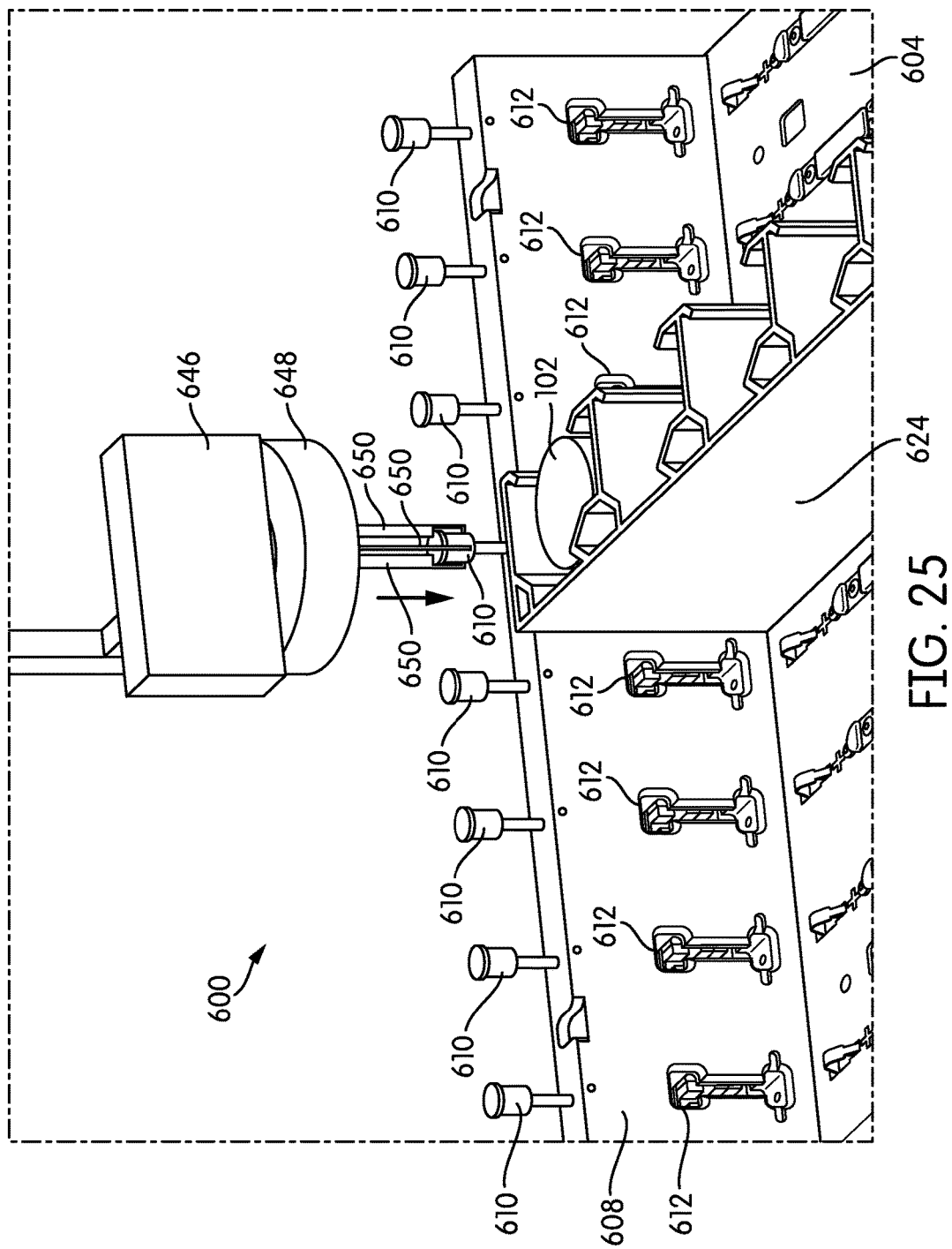
FIG. 25 illustrates a front perspective view of an input bay of a sample processing instrument with an input rack slidably received therein, according to an embodiment.

FIG. 25 illustrates this locking step according to an embodiment. A robotic arm 646 having a gripper 648 engages end portion 614 of locking pin 610 and moves in the downward direction of the annotated arrow in FIG. 25 to move locking pin 610 down to the locked configuration. In some embodiments, gripper 648 includes a plurality of prongs 650, for example, three prongs 650 as shown in FIG. 25. Each prong 650 defines a recess configured to receive a portion of end portion 614 of locking pin 610. As robotic arm 646 moves in the direction of the annotated arrow in FIG. 25, the upper surfaces defining the recesses in prongs 650 engages the terminal edge of end portion 614 of locking pin 610 so that the upper surfaces defining the recesses in prongs 650 push locking pin 610 down to the locked configuration. In some embodiments, robotic arm 646 is also configured to move sample containing receptacles 102 and processing receptacles 101 within the automated instrument, for example, from input rack 624 to sample processing station 107 or the printer (see FIGS. 18 and 19) as described in the above embodiments. In such embodiments, the recesses defined by each prong 650 are also configured to securely receive a portion (e.g., the cap) of sample containing receptacles 102 and processing receptacles 101.

Subsequently, in some embodiments, robotic arm 646 moves locking pin 610 from the locked configuration to the unlocked configuration such that the prong at end portion 616 of locking pin 610 does not occlude opening 612 defined by panel 608 and is removed from hole 640 of tab 638 of rack 624—locking pin 610 disengages rack 624. At this point, rack 624 can move within input bay 600.

Figure 26:
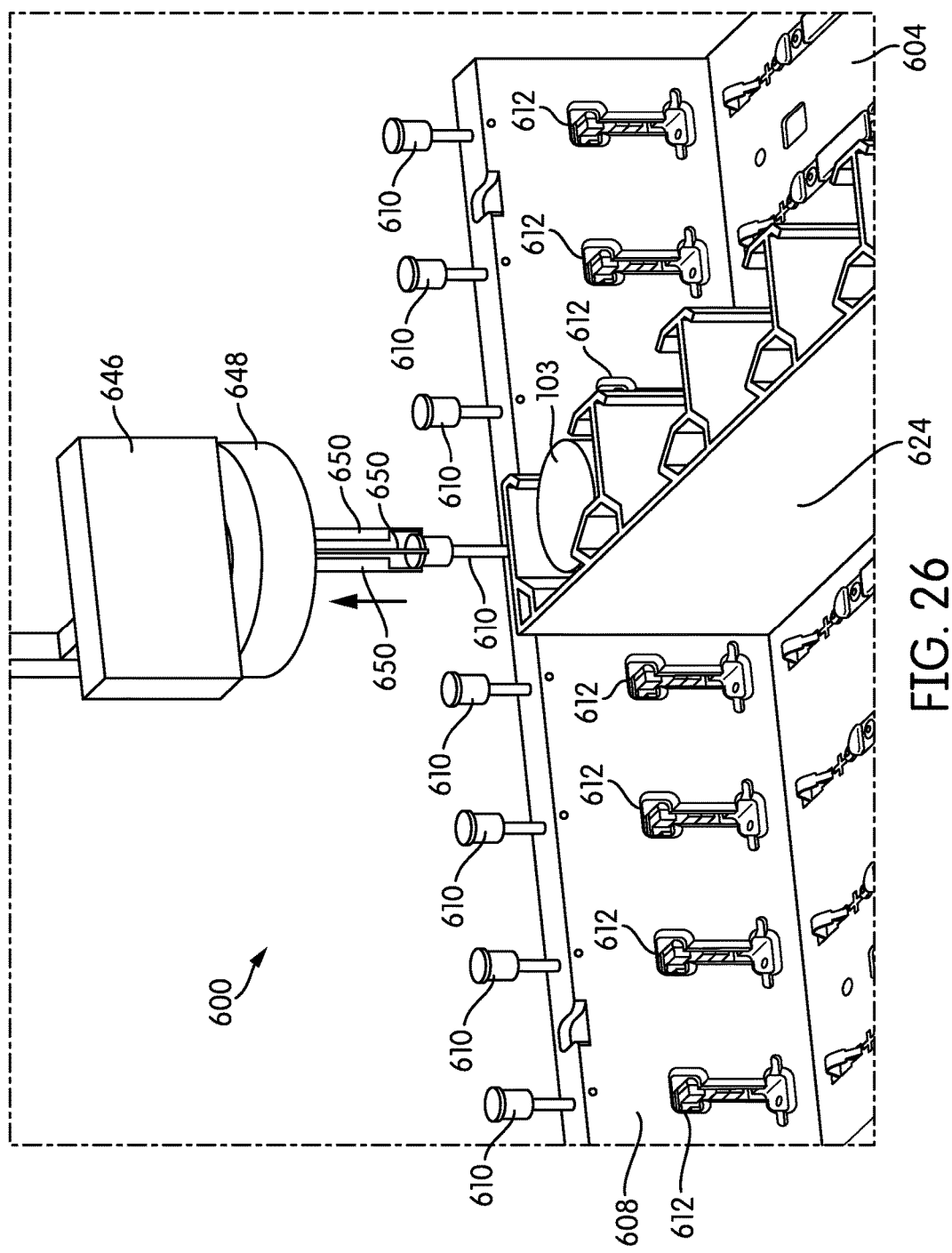
FIG. 26 illustrates another front perspective view of an input bay of a sample processing instrument with an input rack slidably received therein, according to an embodiment.

FIG. 26 illustrates this unlocking step according to an embodiment. Robotic arm 646 having gripper 648 engages end portion 614 of locking pin 610 and moves in the upward direction of the annotated arrow to move locking pin 610 up to the unlocked configuration. As robotic arm 646 moves in the direction of the annotated arrow in FIG. 26, the lower surfaces defining the recesses in prongs 650 engage flange 620 of end portion 614 of locking pin 610 so that the lower surfaces defining the recesses in prongs 650 pull locking pin 610 up to the unlocked configuration.

In some embodiments, robotic arm 646 is configured to perform any one of the sample processing steps identified above that use a robotic arm.

For example, robotic arm 646 is configured to perform any one of the sample processing steps for processing of a SurePath® sample or a ThinPrep® sample identified above that uses a robotic arm. For example, in some embodiments of processing a ThinPrep® sample, robotic arm 646 moves a locking pin 610 to the locked configuration to secure input rack 624 holding a sample containing receptacle 211 and a processing receptacle 101 within the automated processing instrument. Then robotic arm 646 having receptacle gripper 648 picks sample containing receptacle 211 from input rack 624 and places sample containing receptacle 211 in a corresponding container holster 206 on carousel 209 in processing station 107. Next, if necessary, robotic arm 646 having receptacle gripper 648 picks the corresponding processing receptacle 101 from input rack 624 and places processing receptacle 101 in the printer (see FIGS. 18 & 19) for printing a barcode (or other machine readable label) on processing receptacle 101. Then robotic arm 646 picks processing receptacle 101 from the printer (see FIGS. 18 & 19) and places processing receptacle 101 in processing receptacle holster 208 on carousel 209 in processing station 107. Robotic arm 646 with receptacle gripper 648 then picks sample containing receptacle 211 from sample processing station 107 and places sample containing receptacle 211 on input rack 624 in input bay 600, and robotic arm 646 picks processing receptacle 101 from sample processing station 107 and places processing receptacle 101 on an output rack in an output bay of the automated instrument (e.g., output rack 104 or output rack 728 described below). Robotic arm 646 moves locking pin 610 to the unlocked configuration to disengage input rack 624, allowing input rack 624 to move within input bay 600 of the automated processing instrument.

For example, in some embodiments of processing a SurePath® sample, robotic arm 646 moves a locking pin 610 to the locked configuration to secure input rack 624 holding a sample containing receptacle 210 and a processing receptacle 101 within the automated processing instrument. Then robotic arm 646 having receptacle gripper 648 picks sample containing receptacle 210 from input rack 624 and places sample containing receptacle 210 in a corresponding container holster 207 on carousel 209 in processing station 107. Next, if necessary, robotic arm 646 picks the corresponding processing receptacle 101 from input rack 624 and places processing receptacle 101 in the printer (see FIGS. 18 & 19) for printing a barcode (or other machine readable label) on processing receptacle 101. Then robotic arm 646 picks processing receptacle 101 from the printer (see FIGS. 18 & 19) and places processing receptacle 101 in processing receptacle holster 208 on carousel 209 in processing station 107. Robotic arm 646 picks sample containing receptacle 210 from processing station 107 and places sample containing receptacle 210 on input rack 624 in input bay 600. Robotic arm 646 picks processing receptacle 101 from processing station 107 and places processing receptacle 101 (i) on an output rack (for example, output rack 104 or output rack 728 described below) in an output bay of the automated instrument, (ii) in incubator 105 for incubation, or (iii) in dedicated incubator 504 for incubation. And if processing receptacle 101 is positioned in dedicated incubator 504, robotic arm 646 moves processing receptacle 101 from incubator 504 to an output rack (for example, output rack 104 or output rack 728 described below) in an output bay of the automated instrument after incubation. Robotic arm 646 also moves locking pin 610 to the unlocked configuration to disengage input rack 624, allowing input rack 624 to move within input bay 600 of the automated processing instrument.

Locking Output Racks

Figure 27:
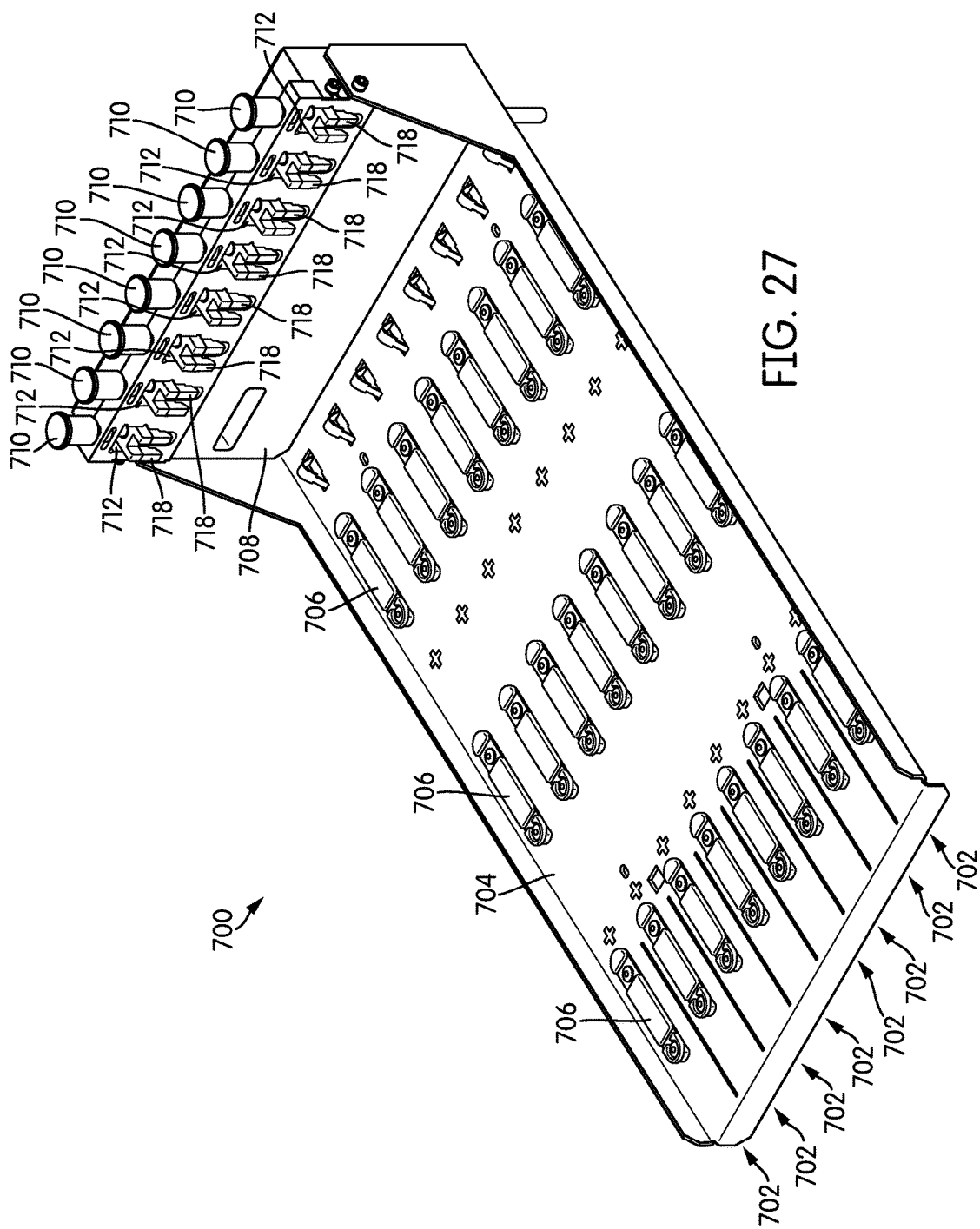
FIG. 27 illustrates a front perspective view of an output bay of a sample processing instrument, according to an embodiment.

In some embodiments, the automated instrument is configured to lock output racks within the automated instrument. FIG. 27 illustrates an output bay 700 of the automated processing instrument configured to lock output racks within the instrument according to an embodiment. Output bay 700 is configured to movably receive a plurality of output racks (e.g., output racks 104 or output racks 728 described below). Output bay 700 defines a plurality of lanes 702 for slidably receiving output racks. For example, output bay 700 can define eight lanes 702 for slidably receiving eight output racks as shown in FIG. 27. In other embodiments, output bay 700 defines more or less than eight lanes 702 for slidably receiving more or less than eight output racks. Each lane 702 can include one or more guides 706 extending from a panel 704 of output bay 700. In some embodiments, panel 704 is planar. Guides 706 are configured to be slidably received within a corresponding recess on an opposing surface of the output racks.

In some embodiments, output bay 700 also includes a panel 708 extending, for example, perpendicularly, from panel 704. In some embodiments, the surface of panel 708 facing lanes 702 is planar. In some embodiments, panel 708 stops the insertion of the output racks (e.g., output racks 104 or output racks 728 described below) within output bay 700 and, thus, defines the fully inserted position of output racks within output bay 700.

Output bay 700 can also include a plurality of locks for locking a corresponding output rack (e.g., output racks 104 or output racks 728 described below) within output bay 700 during sample processing. Each lock is configured to move between (1) a locked configuration that engages and secures a corresponding output rack (e.g., output racks 104 or output racks 728 described below) within the automated instrument and (2) an unlocked configuration that disengages and allows the corresponding output rack (e.g., output racks 104 or output racks 728 described below) to move within the automated instrument. For example, in some embodiments, each lock comprises a locking pin 710. In some embodiments, locking pins 710 are movably coupled to panel 708. For example, in some embodiments, locking pins 710 are slidably coupled to panel 708 such that locking pins 710 translate in a direction parallel to panel 708 and perpendicular to panel 704.

Figure 28:
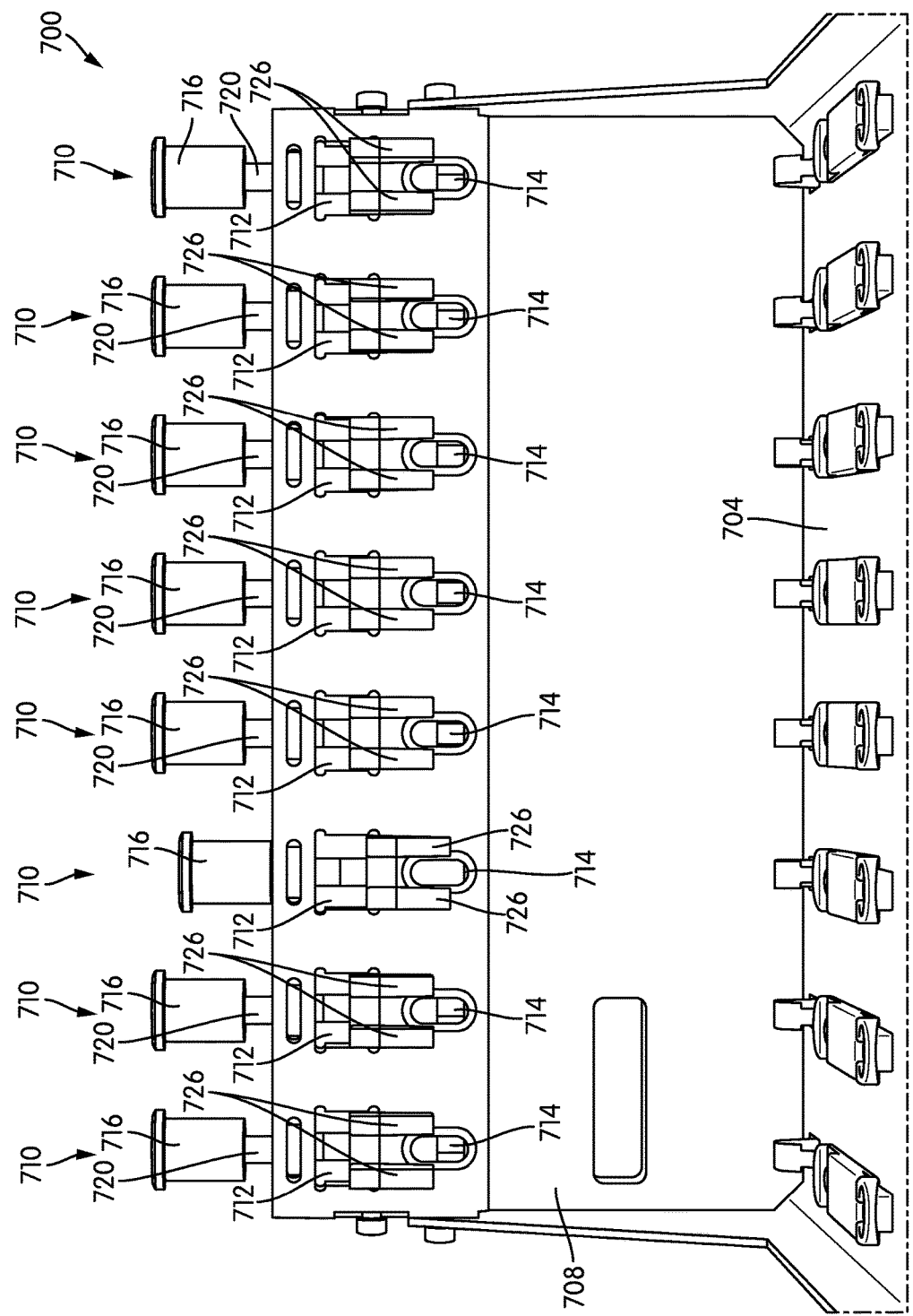
FIG. 28 illustrates a partial front view of the output bay of FIG. 27, according to an embodiment.
Figure 29:
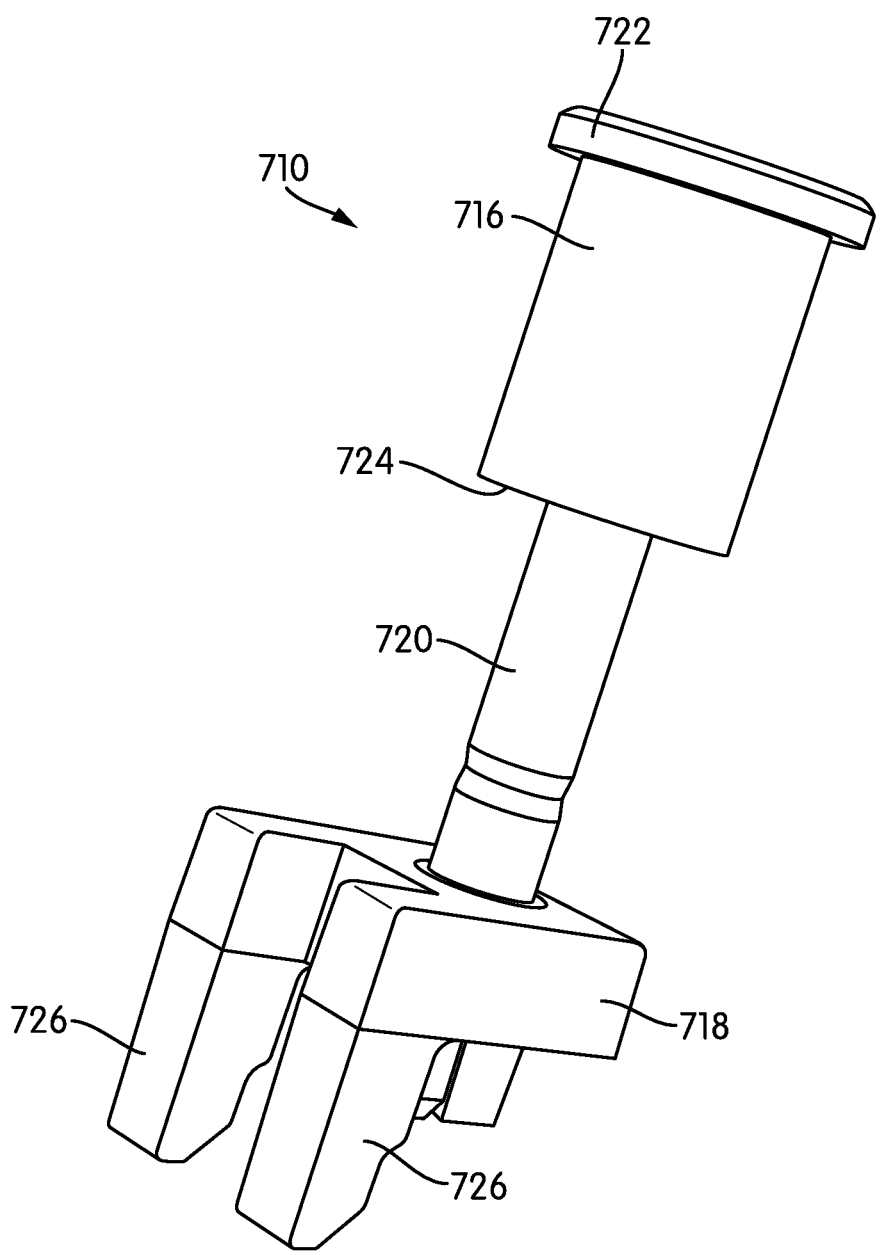
FIG. 29 illustrates a perspective view of a locking pin of an output bay of a sample processing instrument, according to an embodiment.

FIGS. 27-29 illustrate an embodiment of locking pin 710. Each locking pin 710 includes a first end portion 716, a second end portion 718, and an intermediate portion 720 extending between first end portion 716 and second end portion 718. As best seen in FIGS. 27 and 28, locking pin 710 is movably coupled to output bay 700 such that first end portion 716 extends beyond panel 708 in a direction away from panel 704. First end portion 716 can be cylindrical as shown in FIGS. 27-29. First end portion 716 can include a flange 722 extending from the main body portion of first end portion 716. And first end portion 716 can have a width greater than a width of intermediate portion 720, defining a shoulder 725 at the interface of first end portion 716 and intermediate portion 720. In some embodiments, intermediate portion 720 is elongated and cylindrical as shown in FIG. 29. And in some embodiments, second end portion 718 defines at least one prong. For example, as shown in FIG. 29, second end portion 718 defines two spaced apart prongs 726 that are offset from the axis of intermediate portion 720 (and first end portion 716).

In other embodiments (not shown), locking pin 710 can be configured similar to locking pin 610 described above. For example, locking pin 710 can have a single prong in some embodiments.

Referring to FIGS. 27 and 28, panel 708 of output bay 700 defines a plurality of openings 712 in some embodiments. The number of openings 712 corresponds to the number of locking pins 710 and lanes 702 in some embodiments. In some embodiments, each lane 702 has a corresponding locking pin 710. In other embodiments (not shown), one or more lanes 702 may not have a corresponding locking pin 710 or opening 712. Each locking pin 710 is coupled to panel 708 such that each locking pin 710 moves between a locked configuration (for example, in FIG. 28, the configuration of the fourth locking pin 710 from the left) and an unlocked configuration (for example, in FIG. 28, the configurations of all the locking pins 710 except for the fourth locking pin 710 from the left). In some embodiments, locking pins 710 are configured such that prongs 726 of each locking pin 710 extend beyond opening 712 defined in panel 708 in a direction toward lanes 702 as shown in FIGS. 27 and 28. In some embodiments, locking pins 710 are configured such that the second end portions 718 engage output racks 728 (or output racks 104) at the locked configuration, preventing output racks 728 (or output racks 104) from moving within output bay 700 of the automated instrument and, thus, securing the output racks 728 (or output racks 104) within the automated instrument. In some embodiments, locking pins 710 are configured such that the second end portions 718 disengage output racks 728 (or output racks 104) at the unlocked configuration, allowing output racks 728 (or output racks 104) to move within output bay 700 of the automated instrument.

Figure 30:
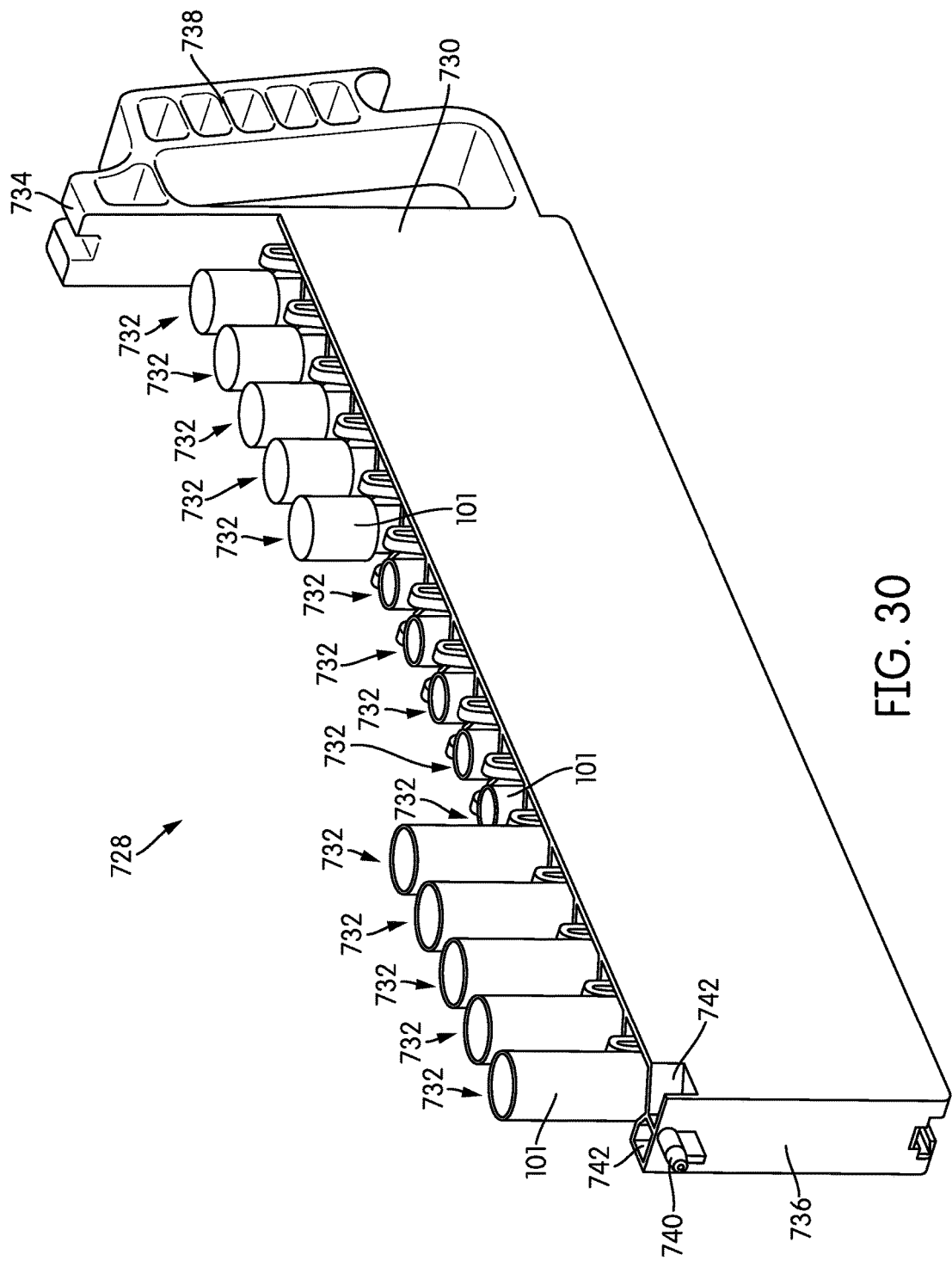
FIG. 30 illustrates a perspective view of an output rack, according to an embodiment.
Figure 31:
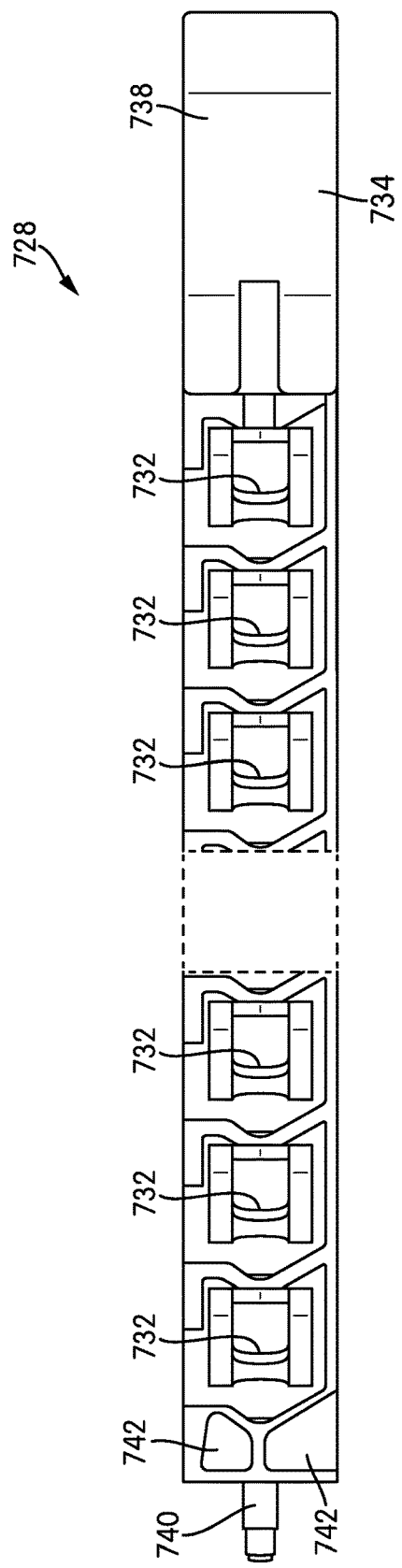
FIG. 31 illustrates a top view of an output rack, according to an embodiment.

FIGS. 30 and 31 illustrate an output rack 728 according to an embodiment. In some embodiments, output rack 728 is configured to hold a plurality of processing receptacles 101. For example, output rack 728 includes a main body 730 that defines a plurality of pockets 732 configured to receive a plurality of processing receptacles 101. At a first end portion 734, output rack 728 can include a handle 738 configured to allow a user to grasp and move output rack 728. For example, a user can grasp handle 738 and move output rack 728 along a lane 702 defined by output bay 700.

Output rack 728 defines at least one recess configured to receive at least one prong 726 of second end portion 718 of a corresponding locking pin 710 when the locking pin 710 is at the locked configuration. In some embodiments, the recess can be a recessed cavity (such as a recessed pocket) or an opening such as a through hole. For example, in some embodiments, output rack 728 defines a pair of recessed pockets 742 at a second end portion 736 of output rack 728. Pockets 742 are configured to receive the prongs 726 of second end portion 718 of locking pin 710 when locking pin 710 is at the locked configuration. In some embodiments, an upper surface of output rack 728 facing locking pin 710 defines pockets 742 as shown in FIGS. 30 and 31. Pockets 724 can be uniform in some embodiments, or pockets 724 can vary from each other as shown in FIGS. 30 and 31 in some embodiments. When prongs 726 of second end portion 718 of a corresponding locking pin 710 are received within pockets 742, the interface between prongs 726 and the wall of output rack 728 defining the distal edge of pockets 742 prevents output rack 728 from moving within output bay 700.

In some embodiments, output rack 728 includes a protrusion 740 that extends from a surface of rack 728 at second end portion 736 of rack 728. Protrusion 740 is configured to help ensure proper alignment of rack 728 by mating with a corresponding opening 714 defined by panel 708 of output bay 700.

Figure 32:
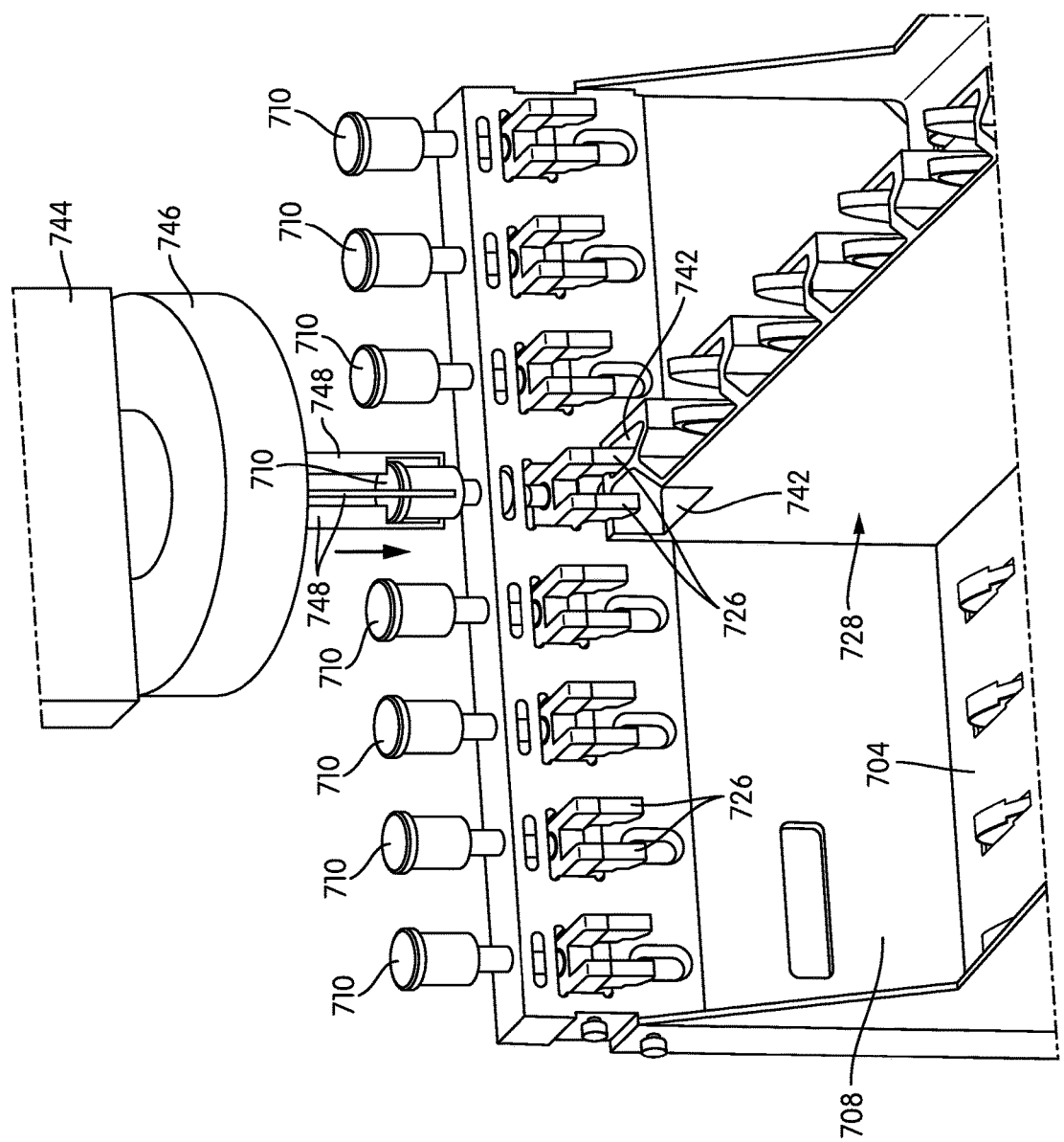
FIG. 32 illustrates a front perspective view of an output bay of a sample processing instrument with an output rack slidably received therein, according to an embodiment.
Figure 33:
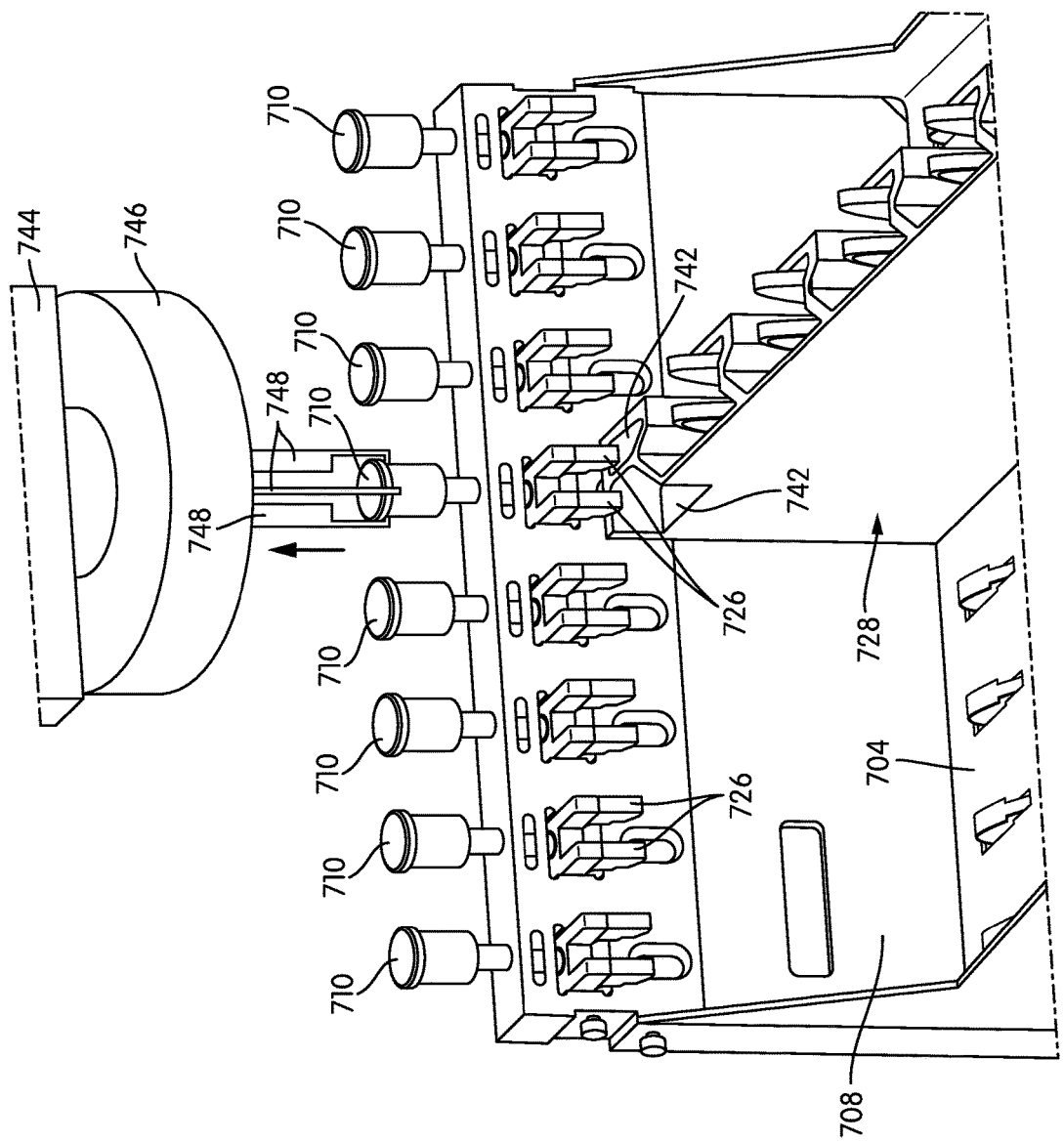
FIG. 33 illustrates another front perspective view of an output bay of a sample processing instrument with an output rack slidably received therein, according to an embodiment.

In use, the user aligns output rack 728 with a desired lane 702 and then inserts output rack 728 into the output bay 700 until second end portion 736 of output rack 728 abuts panel 708 of output bay 700 (as shown in FIGS. 32 and 33). At this point, locking pin 710 is at the unlocked configuration such that prongs 726 of locking pin 710 are above and disengaged with output rack 728. Next, in some embodiments, a robotic arm 744 moves locking pin 710 from the unlocked configuration to the locked configuration such that prongs 726 at end portion 718 of locking pin 710 extend within pockets 742 defined by output rack 728—locking pin 710 engages rack 728. At this point, locking pin 710 secures output rack 728 within output bay 700, preventing movement of rack 728 within output bay 700.

FIG. 32 illustrates this locking step according to an embodiment. As shown in FIG. 32, a robotic arm 744 having a gripper 746 engages end portion 716 of locking pin 710 and moves in the downward direction of the annotated arrow to move locking pin 710 to the locked configuration. In some embodiments, gripper 746 includes a plurality of prongs 748, for example, three prongs 748 as shown in FIG. 32. Each prong 748 defines a recess configured to receive a portion of end portion 716 of locking pin 710. As robotic arm 744 moves in the downward direction of the annotated arrow in FIG. 32, the upper surfaces defining the recesses in prongs 748 engage the terminal edge of end portion 716 of locking pin 710 so that, as robotic arm 744 moves toward panel 704 of output bay 700, the upper surfaces defining the recesses in prongs 748 push locking pin 710 downward to the locked configuration. In some embodiments, robotic arm 744 is also configured to move sample containing receptacles 102 and processing receptacles 101 from rack 624 to sample processing station 107 or the printer (see FIGS. 18 and 19) as described in the above embodiments. In some embodiments, robotic arm 744 is the same robotic arm described above with reference to FIGS. 25 and 26 (i.e., robotic arm 646). In other embodiments, robotic arm 744 is a separate robotic arm from robotic arm 646 described above with reference to FIGS. 25 and 26. In some embodiments, the recesses defined by each prong 748 are also configured to securely receive a portion (e.g., the cap) of sample containing receptacles 102 and processing receptacles 101.

Subsequently, in some embodiments, robotic arm 744 moves locking pin 710 from the locked configuration to the unlocked configuration such that prong 726 at end portion 718 of locking pin 710 are not received within pockets 742 defined by output rack 728—locking pin 710 disengages rack 728. At this point, output rack 728 can move within output bay 700.

FIG. 33 illustrates this unlocking step according to an embodiment. Robotic arm 744 having gripper 746 engages end portion 716 of locking pin 710 and moves in the upward direction of the annotated arrow to move locking pin 710 to the unlocked configuration. As robotic arm 744 moves in the upward direction of the annotated arrow in FIG. 33, the lower surfaces defining the recesses in prongs 748 engage the flange 722 of first end portion 716 of locking pin 710 so that, as robotic arm 744 moves away from panel 704 of output bay 700, the lower surfaces defining the recesses in prongs 748 pull locking pin 710 up to the unlocked configuration.

In some embodiments, robotic arm 744 is configured to perform any one of the above processing steps identified above that use a robotic arm, for example, any one of the sample processing steps for processing of a SurePath® sample or a ThinPrep® sample identified above that uses a robotic arm. For example, in some embodiments of processing a ThinPrep® sample, robotic arm 744 moves a locking pin 710 to the locked configuration to secure output rack 728 configured to hold a processing receptacle 101 within the automated processing instrument. Then robotic arm 744 having receptacle gripper 746 picks sample containing receptacle 211 from an input rack, for example, input rack 624, and places sample containing receptacle 211 in a corresponding container holster 206 on carousel 209 in processing station 107. Next, if necessary, robotic arm 744 having receptacle gripper 746 picks the corresponding processing receptacle 101 from an input rack, for example, input rack 624, and places processing receptacle 101 in the printer (see FIGS. 18 & 19) for printing a barcode (or other machine readable label) on processing receptacle 101. Then robotic arm 744 picks processing receptacle 101 from the printer (see FIGS. 18 & 19) and places processing receptacle 101 in processing receptacle holster 208 on carousel 209 in processing station 107. Robotic arm 744 with receptacle gripper 746 picks sample containing receptacle 211 at processing station 107 and places sample containing receptacle 211 in an input rack, for example, input rack 624. Robotic arm 744 with receptacle gripper 746 picks processing receptacle 101 and places processing receptacle 101 on output rack 728 in output bay 700. Then robotic arm 744 moves locking pin 710 to the unlocked configuration to disengage output rack 728, allowing output rack 728 to move within the automated processing instrument.

For example, in some embodiments of processing a SurePath® sample, robotic arm 744 moves a locking pin 710 to the locked configuration to secure output rack 728 configured to hold a processing receptacle 101 within the automated processing instrument. Robotic arm 744 having receptacle gripper 746 picks sample containing receptacle 210 from an input rack, for example, input rack 624, and places sample containing receptacle 210 in a corresponding container holster 207 on carousel 209 in processing station 107. Next, if necessary, robotic arm 744 having receptacle gripper 746 picks the corresponding processing receptacle 101 from an input rack, for example, input rack 624, and places processing receptacle 101 in the printer (see FIGS. 18 & 19) for printing a barcode (or other machine readable label) on processing receptacle 101. Then robotic arm 744 picks processing receptacle 101 from the printer (see FIGS. 18 & 19) and places processing receptacle 101 in processing receptacle holster 208 on carousel 209 in processing station 107. Robotic arm 744 with receptacle gripper 746 picks sample containing receptacle 210 from processing station 107 and places sample containing receptacle 210 on an input rack, for example, input rack 624. Robotic arm 744 picks processing receptacle 101 from processing station 107 and places processing receptacle 101 on output rack 728, incubator 105, or dedicated incubator 504 for incubation. And if processing receptacle 101 is positioned in dedicated incubator 504, robotic arm 744 moves processing receptacle 101 from incubator 504 to output rack 728 after incubation. Then robotic arm 744 moves locking pin 710 to the unlocked configuration to disengage output rack 728, allowing output rack 728 to move within the automated processing instrument (and allowing rack 728 to be removed from the automated processing instrument and inserted into a separate instrument, for example, an automated assay instrument).

Locking Consumable Drawers

In some embodiments, the automated instrument is configured to lock movable drawers within the automated instrument. For example, referencing FIG. 1, in some embodiments, the automated processing instrument is configured to lock at least one of drawer 109 (which is configured to hold solid waste bin 108 and, in some embodiments, liquid waste bin 502) and drawer 111 (which is configured to hold pipette tip trays 110 that store pipette tips and, in some embodiments, reagent containing receptacle 503 containing a reagent) within the automated instrument. The instrument is configured to movably receive drawer 109 and drawer 111. The automated instrument can include a plurality of locks for locking corresponding drawers within the automated instrument. Each lock is configured to move between (1) a locked configuration that engages and secures a corresponding drawer (e.g., drawer 111 or drawer 109)

within the automated instrument and (2) an unlocked configuration that disengages and allows the corresponding drawer (e.g., drawer 111 or drawer 109) to move within the automated instrument.

For example, in some embodiments, each lock comprises a locking pin such as the above described locking pins 610 or 710. In some embodiments, the locking pins are movably coupled to a panel defining the space in which the drawer moves. In some embodiments, the locking pins are configured such that at least a portion of the locking pin engages the corresponding drawer (e.g., drawer 111 or drawer 109) at the locked configuration, preventing the corresponding drawer (e.g., drawer 111 or drawer 109) from moving within the automated instrument and, thus, securing the corresponding drawer (e.g., drawer 111 or drawer 109) within the automated instrument. In some embodiments, the locking pin is configured such that the locking pin disengages the corresponding drawer (e.g., drawer 111 or drawer 109) at the unlocked configuration, allowing the corresponding drawer (e.g., drawer 111 or drawer 109) to move within the automated instrument.

In some embodiments, the corresponding drawer (e.g., drawer 111 or drawer 109) defines at least one recess configured to receive at least one prong of the drawer locking pin. In some embodiments, the recess can be a recessed cavity (such as a recessed pocket) or an opening such as a through hole. In some embodiments, the drawer locking pin used to lock the drawer has a single prong or two prongs like locking pin 610 and locking pin 710, respectively, as described above. In some embodiments, the corresponding drawer (e.g., drawer 111 or drawer 109) defines a pair of pockets like pockets 742 of output rack 728 described above that receive prongs of the drawer locking pin. In other embodiments, the corresponding drawer (e.g., drawer 111 or drawer 109) includes a tab that extends from a surface of the drawer and defines a through hole that is configured to receive at least one prong of the drawer locking pin, like tab 638 and hole 640 of input rack 624 described above.

In use, the user slides the drawer (e.g., drawer 111 or drawer 109) into the automated instrument until the drawer reaches its closed position. At this point, the locking pin is at an unlocked configuration such that the at least one prong of the drawer locking pin is disengaged with the drawer (e.g., drawer 111 or drawer 109). Next, in some embodiments, a robotic arm moves the drawer locking pin from the unlocked configuration to the locked configuration such that the at least one prong of the drawer locking pin extends within the recess defined by the drawer—the drawer locking pin engages the drawer (e.g., drawer 111 or drawer 109). At this point, the drawer locking pin secures the drawer (e.g., drawer 111 or drawer 109) within the automated instrument, preventing movement of the drawer (e.g., drawer 111 or drawer 109) within the automated instrument.

In some embodiments, a robotic arm having a gripper moves the drawer locking pin between the locked and unlocked configurations. In some embodiments, the robotic arm that moves the drawer locking pin is robotic arm 646 or robotic arm 744 described above that move locking pins 610 and locking pins 710, respectively. In some embodiments, the same robotic arm moves locking pin 610, locking pin 710, and the drawer locking pin. In other embodiments, the robotic arm that moves the drawer locking pin is a separate robotic arm from either robotic arm 646 or robotic arm 744 described above. In some embodiments, the robotic arm that moves the drawer locking pin is also configured to move sample containing receptacles 102 and processing receptacles 101 from an input rack, for example, input racks 103 and 624, to sample processing station 107 or the printer (see FIGS. 18 and 19), as described in the above embodiments. In some embodiments, the robotic arm that moves the drawer locking pin is also configured to move processing receptacles 101 from the sample processing station 107 to output racks 104 or 728, to incubator 105, or dedicated incubator 504.

In some embodiments, the robotic arm that moves the drawer locking pin is configured to perform any one of the processing steps identified above that use a robotic arm, for example, any one of the sample processing steps for processing of a SurePath® sample or a ThinPrep® sample identified above that uses a robotic arm.

Electronics Design

Figure 13:
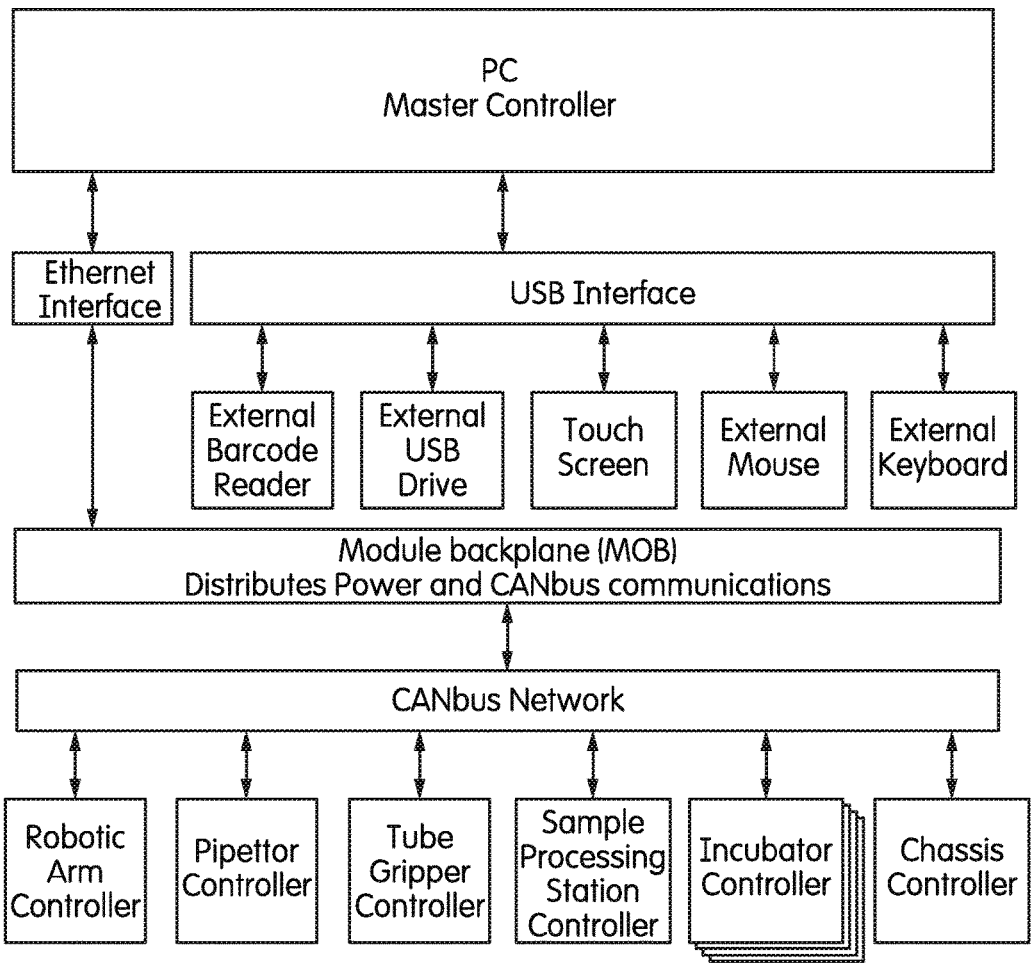
FIG. 13 illustrates an electronic controller architecture, according to an embodiment.

In one embodiment, the electronic design for the instrument includes a Controller Area Network (CANbus) that distributes power and communications between the master PC controller and the system modules. The CANbus and all System peripherals are interfaced to the master PC controller via Ethernet and USB interfaces, for example as depicted in FIG. 13.

In another embodiment, the electronic design for the instrument relies on power line communication (PLC), which permits communication signals to be transmitted over power lines in the instrument. See, e.g., POWER LINE COMMUNICATIONS: THEORY AND APPLICATIONS FOR NARROWBAND AND BROADBAND COMMUNICATIONS OVER POWER LINES (H. C. Ferreira et al. eds., John Wiley & Sons Ltd. 2010). PLC offers certain advantages over CANbus, such as permitting high data transfer rates and utilization of a variety of protocols, such as the CANbus protocol, TCP/IP, among others. Moreover, PLC reduces complexity in the system while offering increased reliability by reducing the number of wires/cables extending between instrument parts. PLC is especially advantageous in moving parts since the number of potential wire/cable pinch-points are reduced and less area is occupied by wires/cables and, if present, their associated conduits.

In one frequent embodiment, the PC will run a stripped down OS. Any time critical activities are handled at the module controller level, and each module has its own controller responsible for running its specific tasks. Commands are, for example, sent down to the modules via the CANbus network. Each module controller contains its own specific set of commands and parameters. Controllers are able to post module status to the master controller at any time.

Some embodiments are implemented via control and computing hardware components, user-created software, data input components, and data output components. Hardware components include, for example, the controller, such as a processor and computer, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.). In some embodiments, the controller comprises a single module that performs manage and process system-wide activities by delegating specific tasks to instrument sub-components or modules. In other embodiments, the controller comprises a plurality of modules that perform discrete sample processing and control steps.

Software comprises instructions stored on non-transitory computer-readable media which, when executed by the control and computing hardware, cause the control and computing hardware to perform one or more automated or semi-automated processes. In some embodiments, the software for processing a sample is stored in memory. In some embodiments, the software for processing a sample is stored in external memory in communication with the controller.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, and without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

While the invention has been described in connection with the above described embodiments, it is to be understood that the invention is not to be limited to the disclosed embodiments, but, on the contrary, is intended to cover various modifications and equivalent arrangements included within the spirit and scope of the appended claims.

Furthermore, those of the appended claims which do not include language in the "means for performing a specified function" format permitted under 35 U.S.C. § 112, 6, are not intended to be interpreted under 35 U.S.C. § 112, 6, as being limited to the structure, material, or acts described in the present specification and their equivalents.

What is claimed is:

1. An automated instrument for processing a sample, the instrument comprising:
    a movable first rack configured to hold a sample containing receptacle, the first rack defining a first recess;
    a movable second rack configured to hold a processing receptacle, the second rack defining a second recess;
    a first lock comprising a first locking pin configured to be received in the first recess, the first lock configured to move between a locked configuration and an unlocked configuration, wherein the first lock is configured to be engaged with the first rack in the locked configuration of the first lock to secure the first rack within the automated instrument, and wherein the first lock is disengaged from the first rack in the unlocked configuration of the first lock to allow movement of the first rack within the automated instrument;
    a second lock comprising a second locking pin configured to be received in the second recess, the second lock configured to move between a locked configuration and an unlocked configuration, wherein the second lock is configured to be engaged with the second rack in the locked configuration of the second lock to secure the second rack within the automated instrument, and wherein the second lock is configured to be disengaged from the second rack in the unlocked configuration of the second lock to allow movement of the second rack within the automated instrument;
    a robotic arm movable within the automated instrument; and
    a controller configured to control the robotic arm to:
    (i) engage and move the first lock to the locked configuration of the first lock,
    (ii) engage and move the first lock to the unlocked configuration of the first lock,
    (iii) engage and move the second lock to the locked configuration of the second lock,
    (iv) engage and move the second lock to the unlocked configuration of the second lock, and
    (v) pick-and-place the sample containing receptacle, the processing receptacle, or both within the automated instrument.

2. The automated instrument of claim 1, wherein:
    the first locking pin has at least one prong configured to be received within the first recess; and
    the second locking pin has at least one prong configured to be received within the second recess.

3. The automated instrument of claim 2, wherein the first recess comprises a through hole.

4. The automated instrument of claim 2, wherein the first rack comprises a tab extending from a surface of the first rack and defining the first recess.

5. The automated instrument of claim 4, further comprising:
    a first bay configured to movably receive the first rack and having a first panel defining a first opening configured to receive the tab, wherein the first locking pin is movably coupled to the first bay such that the at least one prong of the first locking pin is received within the first recess when the tab is received within the first opening and the first lock is in the locked configuration; and
    a second bay configured to movably receive the second rack, wherein the second locking pin is movably coupled to the second bay such that the at least one prong of the second locking pin is received within the second recess when the second lock is in the locked configuration.

6. The automated instrument of claim 2, wherein the first rack has a tapered surface that defines the first recess.

7. The automated instrument of claim 2, wherein the second recess is a pocket defined by a surface of the second rack facing the second lock.

8. The automated instrument of claim 7, wherein the second rack defines a third recess, the third recess being a pocket defined by the surface of the second rack facing the second lock, and wherein the at least one prong of the second locking pin comprises a first prong and a second prong configured to be received within the second recess and the third recess, respectively, when the second lock is in the locked configuration.

9. The automated instrument of claim 1, wherein the controller is configured to control the robotic arm to pick-and-place the sample containing receptacle within the automated instrument.

10. The automated instrument of claim 1, wherein the controller is configured to control the robotic arm to pick-and-place the processing receptacle within the automated instrument.

11. The automated instrument of claim 1, further comprising:
a movable third rack configured to hold a second sample containing receptacle, the third rack defining a third recess;
a third lock comprising a third locking pin configured to be received in the third recess, the third lock configured to move between a locked configuration and an unlocked configuration, wherein the third lock is configured to be engaged with the third rack in the locked configuration of the third lock to secure the third rack within the automated instrument, wherein the third lock is configured to be disengaged from the third rack in the unlocked configuration of the third lock to allow movement of the third rack within the automated instrument, and wherein the controller is configured to control the robotic arm to engage and move the third lock between the locked configuration and the unlocked configuration.

12. The automated instrument of claim 11, wherein the controller is configured to control the robotic arm to pick-and-place the second sample containing receptacle within the automated instrument.

13. The automated instrument of claim 1, further comprising:
a movable third rack configured to hold a second processing receptacle, the third rack defining a third recess;
a third lock comprising a third locking pin configured to be received in the third recess, the third lock configured to move between a locked configuration and an unlocked configuration, wherein the third lock is configured to be engaged with the third rack in the locked configuration of the third lock to secure the third rack within the automated instrument, wherein the third lock is configured to be disengaged from the third rack in the unlocked configuration of the third lock to allow movement of the third rack within the automated instrument, and wherein the controller is configured to control the robotic arm to engage and move the third lock between the locked configuration and the unlocked configuration.

14. The automated instrument of claim 13, wherein the controller is configured to control the robotic arm to pick-and-place the second processing receptacle within the automated instrument.

15. The automated instrument of claim 1, further comprising:
a movable holding structure configured to hold a sample processing device, the movable holding structure defining a third recess;
a third lock comprising a third locking pin configured to be received in the third recess, the third lock configured to move between a locked configuration and an unlocked configuration, wherein the third lock is configured to be engaged with the holding structure in the locked configuration to secure the holding structure within the automated instrument, wherein the third lock is configured to be disengaged from the holding structure in the unlocked configuration to allow movement of the holding structure within the automated instrument, and wherein the controller is configured to control the robotic arm to engage and move the third lock between the locked configuration and the unlocked configuration.

16. The automated instrument of claim 15, wherein the holding structure is a drawer.

17. The automated instrument of claim 15, wherein the sample processing device is a reagent containing receptacle.

18. The automated instrument of claim 15, wherein the sample processing device is a pipette tip.

19. The automated instrument of claim 17, wherein the controller is configured to control the robotic arm to pick-and-place the reagent containing receptacle within the automated instrument.

20. The automated instrument of claim 18, wherein the controller is configured to control the robotic arm to engage and move the pipette tip within the automated instrument.

* * * * *